(12) United States Patent
Halpern et al.

(10) Patent No.: US 12,232,858 B2
(45) Date of Patent: *Feb. 25, 2025

(54) $T_{1e}$-SENSITIVE INVERSION-RECOVERY IMAGING FOR EPROI

(71) Applicants: Howard J. Halpern, Chicago, IL (US); Boris Epel, Chicago, IL (US)

(72) Inventors: Howard J. Halpern, Chicago, IL (US); Boris Epel, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/127,538

(22) Filed: Mar. 28, 2023

(65) Prior Publication Data

US 2023/0240553 A1  Aug. 3, 2023

Related U.S. Application Data

(62) Division of application No. 15/213,768, filed on Jul. 19, 2016, now Pat. No. 11,612,336, which is a
(Continued)

(51) Int. Cl.
*A61B 5/055*      (2006.01)
*G01R 33/341*     (2006.01)
(Continued)

(52) U.S. Cl.
CPC ............ *A61B 5/055* (2013.01); *G01R 33/341* (2013.01); *G01R 33/3607* (2013.01);
(Continued)

(58) Field of Classification Search
CPC ....... A61B 5/055; G01R 33/341; G01R 33/60
See application file for complete search history.

(56) References Cited

U.S. PATENT DOCUMENTS 3,879,653 A    4/1975   Hyde et al.
4,280,096 A    7/1981   Karthe et al.
(Continued)

OTHER PUBLICATIONS

Gluth, et al., "Large-scale synthesis of a monophosphonated tetrathiatriarylmethyl spin probe for concurrent in vivo measurement of pO2, pH and inorganic phosphate by EPR", "RSC Advances", Jul. 27, 2021, pp. 25951-25954, vol. 11.
(Continued)

*Primary Examiner* — Jeffrey G Hoekstra
*Assistant Examiner* — Gabriel Victor Popescu
(74) *Attorney, Agent, or Firm* — Charles A. Lemaire; Lemaire Patent Law Firm, P.L.L.C.

(57) ABSTRACT

An apparatus and method for improved S/N measurements useful for electron paramagnetic resonance imaging in situ and in vivo, using high-isolation transmit/receive surface coils and temporally spaced pulses of RF energy (e.g., in some embodiments, a RF pi pulse) having an amplitude sufficient to rotate the magnetization by 180 degrees followed after varied delays, by a second RF pulse having an amplitude half that of the initial pulse to rotate the magnetization by, e.g., 90 degrees (a pi/2 pulse), to the plane orthogonal to the static field where it evolves for a short time. Then a third RF pi pulse sufficient to rotate the magnetization by, e.g., 180 degrees, forms an echo (in some embodiments, the second and third pulses are from the same signal as the first pulse but are phase shifted by 0, 90, 180, or 270 degrees to reduce signal artifact), to image human body.

21 Claims, 19 Drawing Sheets
(12 of 19 Drawing Sheet(s) Filed in Color)

Related U.S. Application Data division of application No. 13/032,637, filed on Feb. 22, 2011, now Pat. No. 9,392,957.

(60) Provisional application No. 61/445,037, filed on Feb. 21, 2011, provisional application No. 61/356,555, filed on Jun. 18, 2010, provisional application No. 61/306,917, filed on Feb. 22, 2010.

(51) Int. Cl.
  *G01R 33/36* (2006.01)
  *G01R 33/60* (2006.01)
  *G01V 3/10* (2006.01)

(52) U.S. Cl.
  CPC ......... *G01R 33/3621* (2013.01); *G01R 33/60* (2013.01); *G01V 3/104* (2013.01)

(56) References Cited

U.S. PATENT DOCUMENTS

| | | | |
|---|---|---|---|
| 4,714,886 | A | 12/1987 | Halpern |
| 4,812,763 | A | 3/1989 | Schmalbein |
| 4,984,573 | A | 1/1991 | Leunbach |
| 5,706,805 | A | 1/1998 | Swartz et al. |
| 5,828,216 | A | 10/1998 | Tschudin et al. |
| 5,865,746 | A | 2/1999 | Murugesan et al. |
| 6,150,817 | A | 11/2000 | Lurie et al. |
| 6,639,406 | B1 | 10/2003 | Boskamp et al. |
| 6,977,502 | B1 | 12/2005 | Hertz |
| 7,659,719 | B2 | 2/2010 | Vaughan et al. |
| 7,710,117 | B2 | 5/2010 | Vaughan et al. |
| 7,800,368 | B2 | 9/2010 | Vaughan et al. |
| 7,809,425 | B2 | 10/2010 | Hashimshony et al. |
| 7,990,140 | B2 | 8/2011 | Sugiura |
| 2005/0136002 | A1 | 6/2005 | Fossheim et al. |
| 2007/0207478 | A1 | 9/2007 | Paris |

OTHER PUBLICATIONS

Sundramoorthy, et al., "Orthogonal resonators for pulse in vivo electron paramagnetic imaging at 250 MHz", "Journal of Magnetic Resonance", Mar. 2014, pp. 45-51, vol. 240.
Adams, J.Y., et al., "Visualization of advanced human prostate cancer lesions in living mice by a targeted gene transfer vector and optical imaging.", "Nat Med", Jul. 22, 2002 , pp. 891-897 , vol. 8.
Adriany, et al., "A Geometrically Adjustable 16-Channel Transmit/Receive Transmission Line Array for Improved RF Efficiency and Parallel . . . ", "Magnetic Resonance in Medicine", Jan. 24, 2008, pp. 590-597, vol. 59.
Alam, et al., "Reporter genes: application to the study of mammalian gene transcription.", "Anal Biochem", Aug. 1, 1990, pp. 245-254 , vol. 188.
Beekman, F., et al., "The pinhole: gateway to ultra-high-resolution three-dimensional radionuclide imaging", "Eur J Nucl Med Mol Imaging", Feb. 2007, pp. 151-161, vol. 34, No. 2.
Blasberg, "In vivo molecular-genetic imaging: multi-modality nuclear and optical combinations", "Nucl Med Biol", Nov. 2003, pp. 879-888 , vol. 30.
Blasberg, et al., "Molecular-genetic imaging: current and future perspectives", "The Journal of Clinical Investigation", Jun. 2003, pp. 1620-1629, vol. 111, No. 11.
Bremer, et al., "Optical imaging of matrix metalloproteinase-2 activity in tumors: feasibility study in a mouse model", "Radialogy", Nov. 2001, pp. 523-529, vol. 221, No. 2.
Brizel, D. et al., "Tumor oxygenation predicts for the likelihood of distant metastases in human soft tissue sarcoma", "Cancer Res", Mar. 1, 1996, pp. 941-943, vol. 56.
Brizel, et al., "Tumor hypoxia adversely affects the prognosis of carcinoma of the head and neck.", "Int J Radiat Oncol Biol Phys", May 1, 1997, pp. 285-289, vol. 38.
Brizel, et al., "Oxygenation of head and neck cancer: changes during radiotherapy and impact on treatment outcome.", "Radiother Oncol", Nov. 1999 , pp. 113-117, vol. 53.
Burks, et al., "Optimization of labile esters for esterase-assisted accumulation of nitroxides into cells: a model for in vivo EPR imagi", "Bioconjug Chem", Oct. 2008, pp. 2068-2071, vol. 19, No. 10.
Carmeliet, P., et al., "Role of HIF-1alpha in hypoxia-mediated apoptosis, cell proliferation and tumour angiogenesis.", "Nature", Jul. 30, 1998, pp. 485-490, vol. 394.
Chalfie, et al., "Green fluorescent protein as a marker for gene expression", "Science", Feb. 11, 1994, pp. 802-805, vol. 263.
Dewhirst, et al., "Microvascular studies on the origins of perfusion-limited hypoxia", "British Journal of Cancer", Jul. 1996, pp. S247-S251, vol. 74.
Dothager, et al., "Molecular imaging of pulmonary disease in vivo", "Proceedings of the American Thoracic Society", Aug. 2009, pp. 403-410, vol. 6.
Eaton, Gareth R., et al., "Spin Lattice Relaxation—Part 1, Solids.", "Paper presented at Modern EPR Spectroscopy in Retie, Belgium.", Dec. 17, 2002, pp. 1-32.
Elas, et al., "Electron paramagnetic resonance oxygen images correlate spatially and quantitatively with Oxylite oxygen measurements", "Clin Cancer Res", Jul. 20, 2006, pp. 4209-4217, vol. 12.
Elas, M., et al., "Electron paramagnetic resonance oxygen image hypoxic fraction plus radiation dose strongly correlates with tumor cure in FSa fibrosarcomas.", "Int J Radiat Oncol Biol Phys", Jun. 1, 2008, pp. 542-549, vol. 71.
Epel, Boris J., et al. , "A Versatile High Speed 250-MHz Pulse Imager for Biomedical Applications", "Magn. Reson. Part B (Magn. Reson. Engineering)", Jul. 2008, pp. 163-176, vol. 33B.
Erilov, et al., "Echo-Detected Electron Paramagnetic Resonance Spectra of Spin-Labeled Lipids in Membrane Model Systems.", "J. Phys. Chem. B", 2004, pp. 4501-4507, vol. 108.
Evans, et al., "2-Nitroimidazole (EF5) binding predicts radiation resistance in individual 9L s.c. tumors", "Cancer Research", Jan. 1, 1996, pp. 405-411, vol. 56.
Fink, et al., "Identification of a tightly regulated hypoxia-response element in the promoter of human plasminogen activator inhibitor-", "Blood", Mar. 15, 2002, pp. 2077-2083, vol. 99, No. 6.
Fischbach, et al., "Cancer cell angiogenic capability is regulated by 3D culture and integrin engagement", Jan. 6, 2009, pp. 399-404, vol. 106, No. 2, Publisher: Proc Natl Acad Sci.
Gatenby, R.A. et al., "Oxygen distribution in squamous cell carcinoma metastases and its relationship to outcome of radiation therapy", "Int. J. Radiat. Oncol. Biol. Phys.", May 1988, pp. 831-838 , vol. 14.
Gillespie, et al., "Silencing of hypoxia inducible factor-1alpha by RNA interference attenuates human glioma cell growth in vivo", "Clin. Cancer Res.", Apr. 16, 2007, pp. 2441-2448.
Graeber, T.G. et al.;, "Hypoxia-mediated selection of cells with diminished apoptotic potential in solid tumours.", "Nature", Jan. 4, 1996, pp. 88-91, vol. 379.
Halpern, Howard J., "Stable soluble paramagnetic compounds", "In: L.J. Berliner, Ed., In Vivo EPR(ESR): Theory and Applications, vol. 18. Chapter 8.", 2003, Publisher: Kluwer Academic/Plenum Pub. Corp, New York.
Halpern, Howard J., "Cancer Research", "In: L.J. Berliner, Ed., In Vivo EPR(ESR): Theory and Applications, vol. 18. Chapter 17.", 2003, Publisher: Kluwer Academic/Plenum Pub. Corp, New York.
Halpern, Howard J., et al., "Imaging radio frequency electron-spin-resonance spectrometer with high resolution and sensitivity for in vivo measurement", "Rev. Sci. Instrum.", Jun. 1989, pp. 1040-1050, vol. 60, No. 6.
Halpern, Howard J., et al., "Rapid quantitation of parameters from inhomogeneously broadened EPR spectra", "Journal of Magnetic Resonance", May 1993, pp. 13-22, vol. A 103.
Halpern, et al., "Oxymetry deep in tissues with low-frequency electron paramagnetic resonance", "Proc. Natl. Acad. Sci.", Dec. 1994, pp. 13047-13051, vol. 91.

(56) References Cited

OTHER PUBLICATIONS

Halpern, Howard J., et al., "Low-Frequency EPR Spectrometers: MHz Range", "In: L.J. Berliner, Ed., In Vivo EPR(ESR): Theory and Applications, vol. 18. Chapter 6.", 2003, pp. 45-62, Publisher: Kluwer Academic/Plenum Pub. Corp, New York.
Haney, et al., "Reduction of image artifacts in mice by bladder flushing with a novel double-lumen urethral catheter", Jul. 2006, pp. 175-179, vol. 5, No. 3, Publisher: Mol Imaging.
Haney, C.R., et al., "Characterization of response to radiation mediated gene therapy by means of multimodality imaging.", "Magn Reson Med", May 15, 2009, pp. 348-356, vol. 62.
Harmer, et al., "Advanced Pulse EPR Methods for the Characterization of Metalloproteins", "In Berliner et al., Eds.: High Resolution EPR: Applications to Metalloenzymes and Metals in Medicine", 2009, pp. 13-61, Publisher: Springer, New York, NY.
Herschman, "Molecular imaging: looking at problems, seeing solutions.", "Science", Oct. 24, 2003, pp. 605-608, vol. 302.
Hockel, M. et al., "Association between tumor hypoxia and malignant progression in advanced cancer of the uterine cervix.", "Cancer Res", Oct. 1996, pp. 4509-4515, vol. 56.
Holt, et al., "Studies in enzyme cytochemistry. II. Synthesis of indigogenic substrates for esterases.", "Proc R Soc Lond B Biol Sci", Apr. 8, 1958, pp. 481-494, vol. 148.
Lauterbur, et al., "Theory and simulation of NMR spectroscopic imaging and field plotting by projection reconstruction involving an intrinsic frequency dimension.", "J. Magn. Reson.", Oct. 1, 1984, pp. 536-541, vol. 59.
Lewis, et al., "Evaluation of 64Cu-ATSM in vitro and in vivo in a hypoxic tumor model", "The Journal of Nuclear Medicine", Jan. 1999, pp. 177-183, vol. 40, No. 1.
Lorigan, et al., "Temperature-Dependent Pulsed Electron Paramagnetic Resonance Studies of the S2 State Multiline Signal of the Photosynthetic Oxygen-Evolving Complex", "Biochemistry", Oct. 1994, pp. 12072-12076, vol. 33.
Lorigan, et al., "Electron spin-lattice relaxation studies of different forms of the S2 state multiline EPR signal of the Photosystem II oxygen-evolving complex.", "Photosynthesis Research", Dec. 2000, pp. 189-198, vol. 66.
Louie, A.Y., et al., "In vivo visualization of gene expression using magnetic resonance imaging.", "Nat Biotechnol", Mar. 1, 2000, pp. 321-325, vol. 18.
Lungu, et al., "In vivo imaging and characterization of hypoxia-induced neovascularization and tumor invasion", "International Journal of Oncology", Jan. 2007, pp. 45-54, vol. 30.
Maltempo, "Differentiation of spectral and spatial components in EPR imaging using 2-D image reconstruction algorithms.", "J. Magn. Reson.", Aug. 1986, pp. 156-161, vol. 69.
Massoud, et al., "Molecular imaging in living subjects: seeing fundamental biological processes in a new light", "Genes and Development", Mar. 2003, pp. 545-580.
McCaffrey, et al., "Advancing molecular therapies through in vivo bioluminescent imaging", "Molecular Imaging", Apr. 2003, pp. 75-86, vol. 2, No. 2.
Mechtcheriakova, et al., "Vascular endothelial cell growth factor-induced tissue factor expression in endothelial cells is mediated by EGR-1", "Blood", Jun. 1999, pp. 3811-3823, vol. 93, No. 11.
Melo, et al., "Role of NADPH:cytochrome P450 reductase in the hypoxic accumulation and metabolism of BRU59-21, a technetium-99m-nitroimidazole for imaging tumor hypoxia.", "Biochem Pharmacol", Sep. 1, 2000, pp. 625-634, vol. 60.
Pourgholami, et al., "Inhibitors of vascular endothelial growth factor in cancer.", "Cardiovasc Hematol Agents Med Chem", Oct. 2008, pp. 343-347, vol. 6.
Rosen, G.M., et al., "Dendrimeric-containing nitronyl nitroxides as spin traps for nitric oxide: Synthesis, kinetic and stability studies.", "Macromolecules", Jan. 18, 2003, pp. 1021-1027, vol. 36.
Schabbauer, G., et al.;, "Nuclear factor of activated T cells and early growth response-1 cooperate to mediate tissue factor gene induction by vascular endothelial growth factor in endothelial cells.", "Thromb Haemost", Jun. 2007, pp. 988-997, vol. 97.
Schober, et al., "Multimodality molecular imaging—from target description to clinical studies.", "Eur J Nucl Med Mol Imaging", Feb. 2009, pp. 302-314, vol. 2.
Semenza, "Hypoxia-inducible factor 1: master regulator of O2 homeostasis.", "Curr Opin Genet Dev", Oct. 1998, pp. 588-594, vol. 8.
Shibata, et al., "Development of a hypoxia-responsive vector for tumor-specific gene therapy", "Gene Therapy", Mar. 2000, pp. 493-498, vol. 7.
Shibata, T., et al., "Hypoxia-inducible regulation of a prodrug-activating enzyme for tumor-specific gene therapy.", "Neoplasia", Jan.-Feb. 2002, pp. 40-48, vol. 4.
Stephen, et al., "Promise and progress for functional and molecular imaging of response to targeted therapies.", "Pharm Res", Jun. 2007, pp. 1172-1185, vol. 24.
Studholme, et al., "Automated 3-D registration of MR and CT images of the head", "Medical Image Analysis", Jun. 1996, pp. 163-175, vol. 1, No. 2.
Studholme, et al., "Automated three-dimensional registration of magnetic resonance and positron emission tomography brain images by multires", "Med. Phys.", Jan. 1997, vol. 24, No. 1.
Sun, et al., "Quantitative imaging of gene induction in living animals", "Gene Therapy", Oct. 2001, pp. 1572-1579, vol. 8.
Thurston, et al., "VEGF and Delta-Notch: interacting signalling pathways in tumour angiogenesis", "British Journal of Cancer", Sep. 30, 2008, pp. 1204-1209, vol. 99, No. 8.
Timke, et al., "Combination of vascular endothelial growth factor receptor/platelet-derived growth factor receptor inhibition markedly i", "Clinical Cancer Research", Apr. 1, 2008, pp. 2210-2219.
Vaughan, J.T., et al., "Whole-body imaging at 7T: preliminary results.", "Magn Reson Med", Jan. 2009, pp. 244-248, vol. 61.
Vaughan, J.T., et al., "Clinical Imaging at 7T with a 16 Channel Whole Body Coil and 32 Receive Channels.", "Proceedings 17th Scientific Meeting, International Society for Magnetic Resonance in Medicine", Apr. 2009, p. 392.
Weissleder, et al., "In vivo magnetic resonance imaging of transgene expression", "Nature Medicine", Mar. 2000, pp. 351-355, vol. 6, No. 3.
Weissleder, et al., "Shedding light onto live molecular targets", "Nature Medicine", Jan. 2003, pp. 123-128, vol. 9, No. 1.
Wells, et al., "Multi-modal volume registration by maximization of mutual information", "Medical Image Analysis", Mar. 1996, pp. 35-51, vol. 1, No. 1.
Wilson, et al., "Amplification of MMP-2 and MMP-9 production by prostate cancer cell lines via activation of protease-activated receptors.", "Prostate", Feb. 2, 2004, pp. 168-174, vol. 60.
Zhang, W., et al., "Rapid in vivo functional analysis of transgenes in mice using whole body imaging of luciferase expression.", Oct. 2001, pp. 423-434, vol. 10.

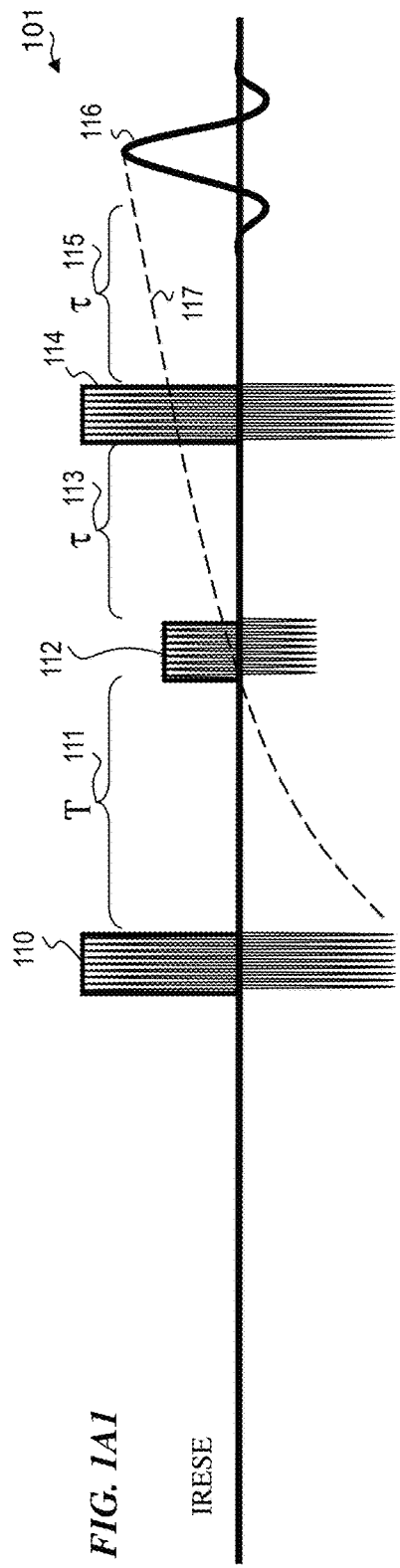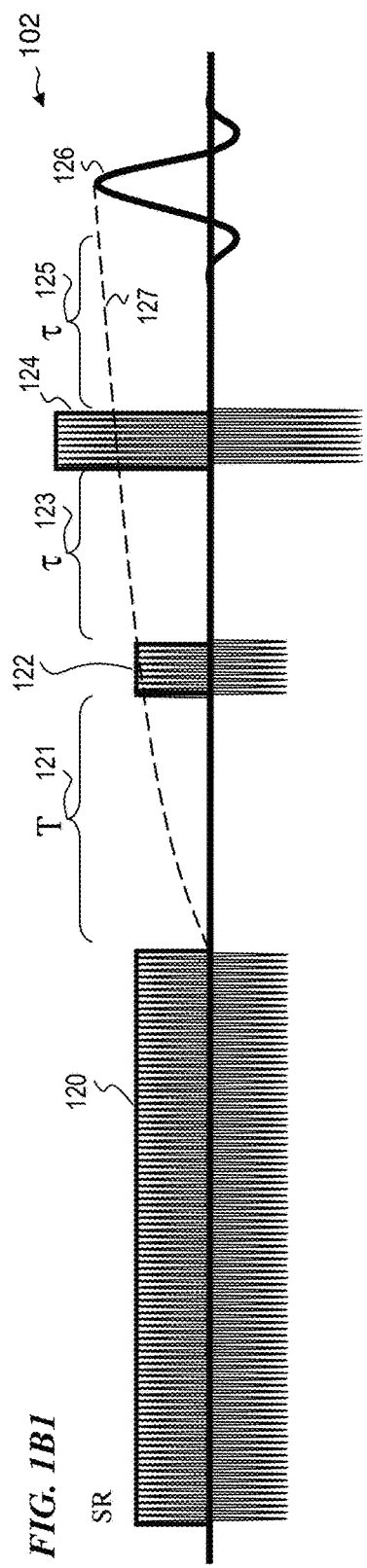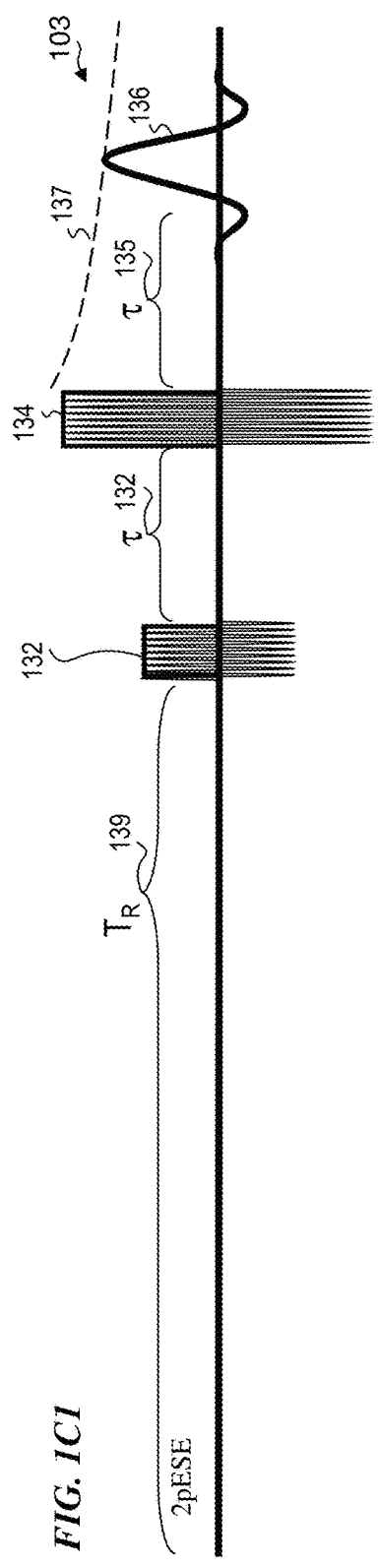

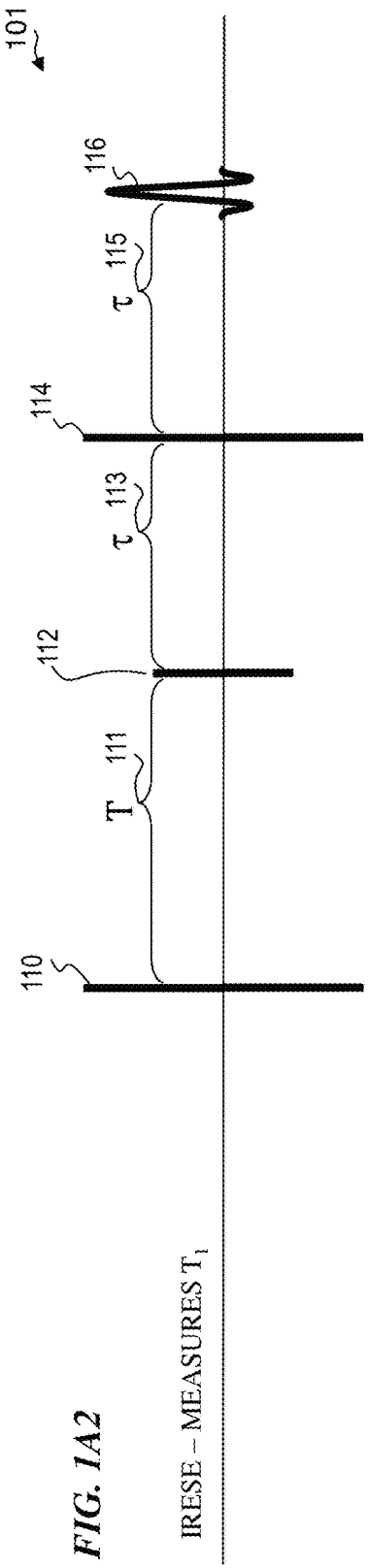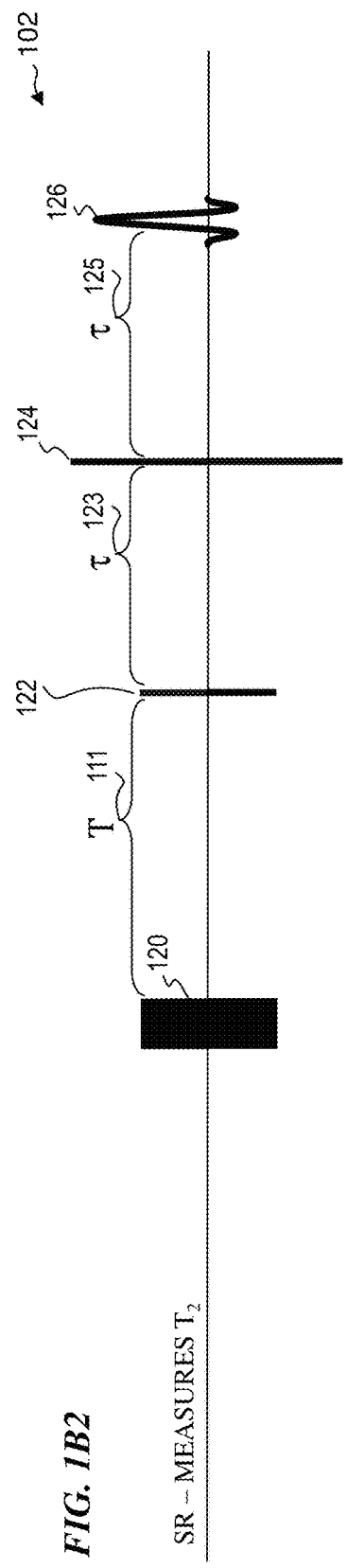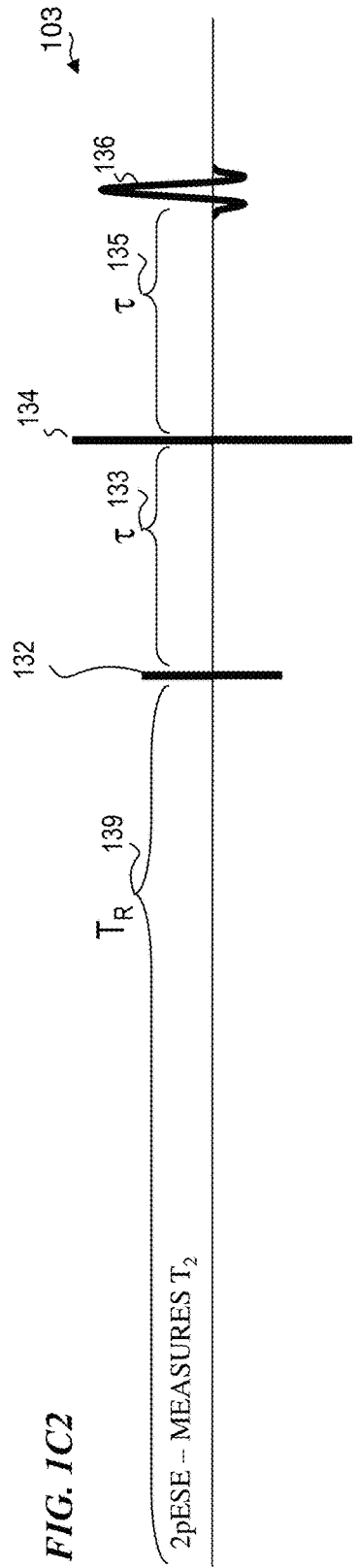
FIG. 1A2  IRESE – MEASURES $T_1$
FIG. 1B2  SR – MEASURES $T_2$
FIG. 1C2  2pESE – MEASURES $T_2$

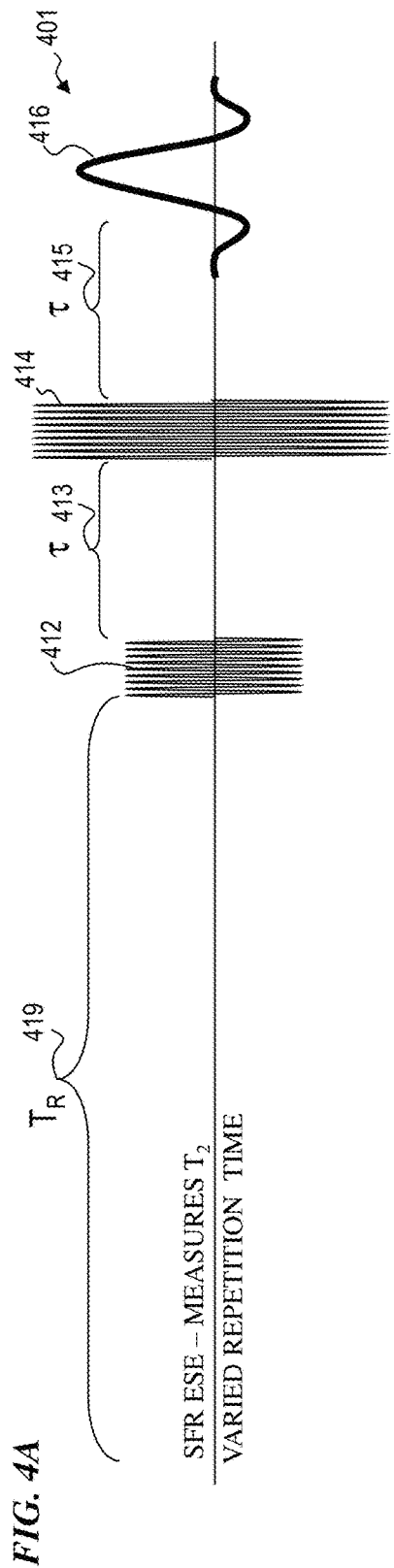
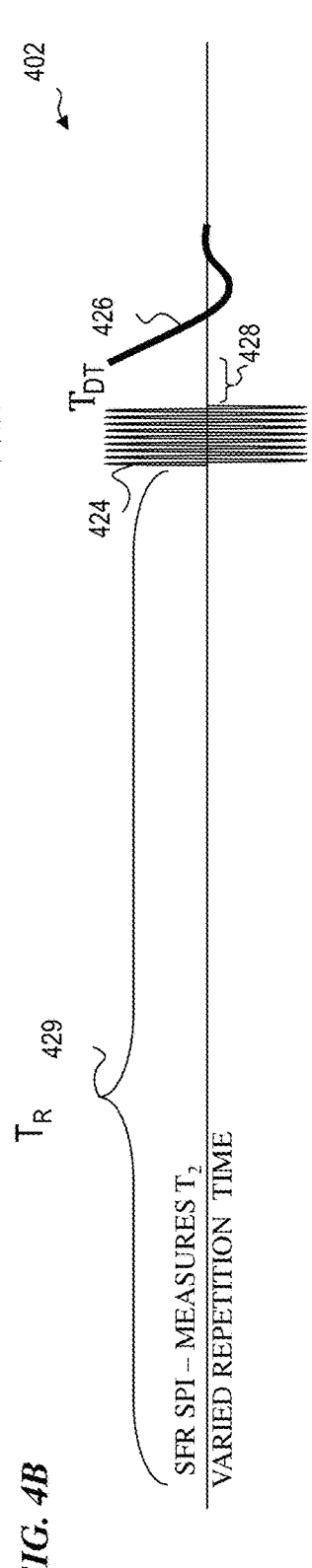
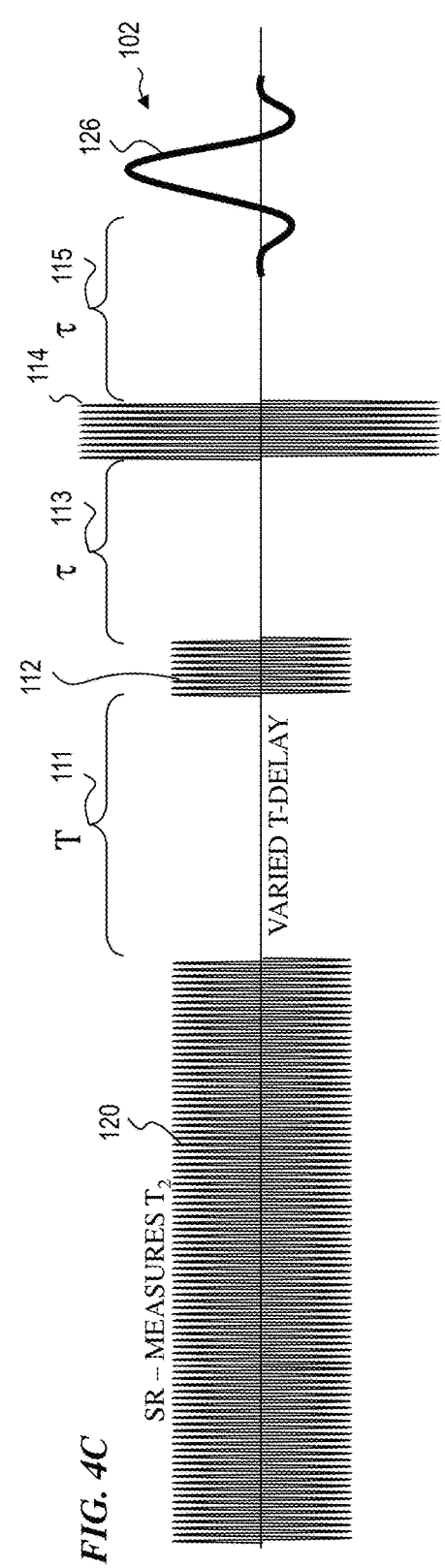

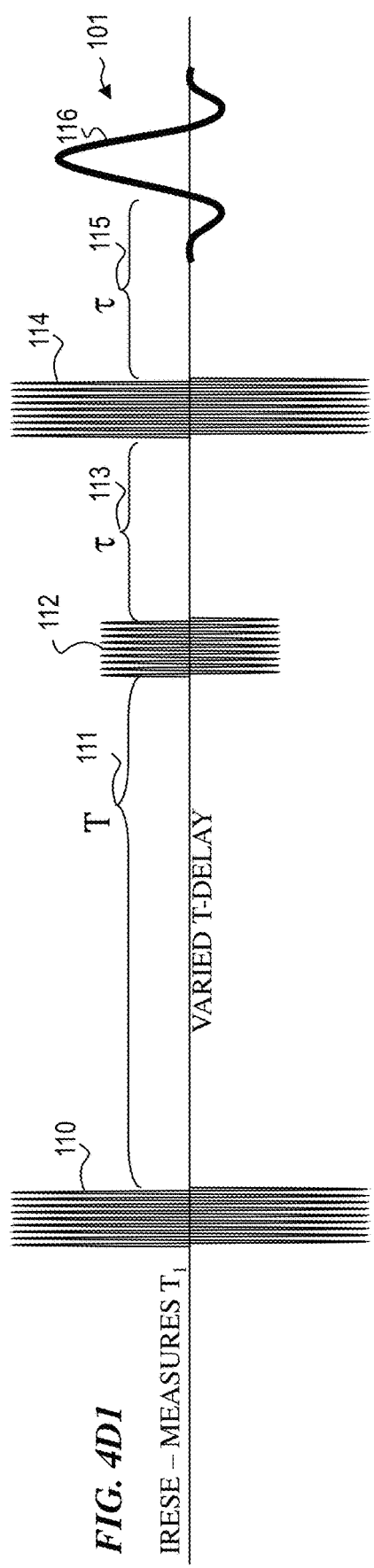
FIG. 4D1
IRESE – MEASURES $T_1$
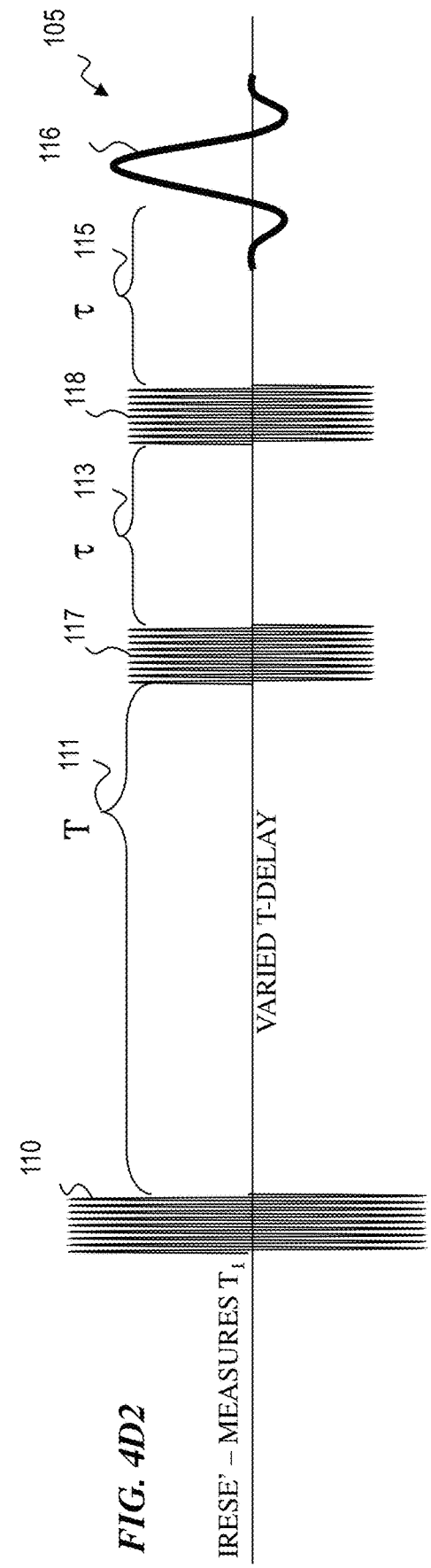
FIG. 4D2
IRESE' – MEASURES $T_1$

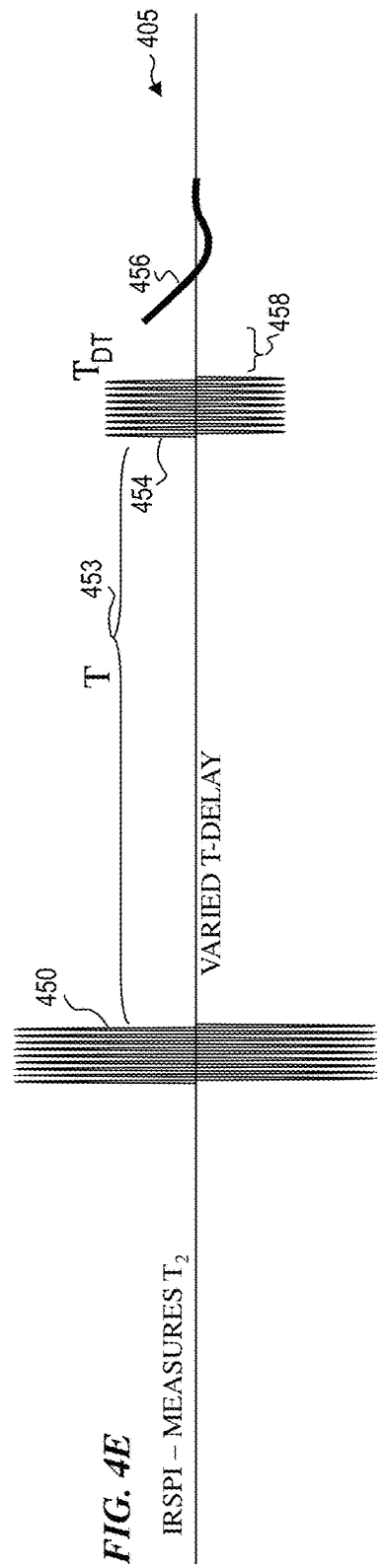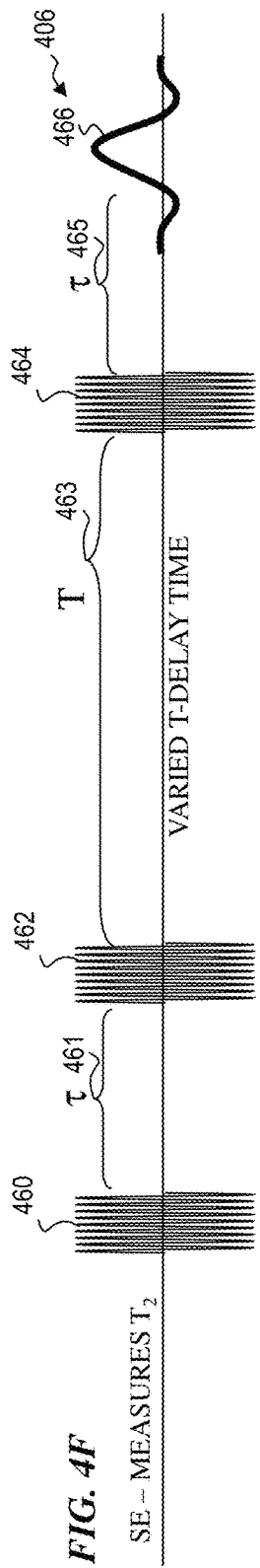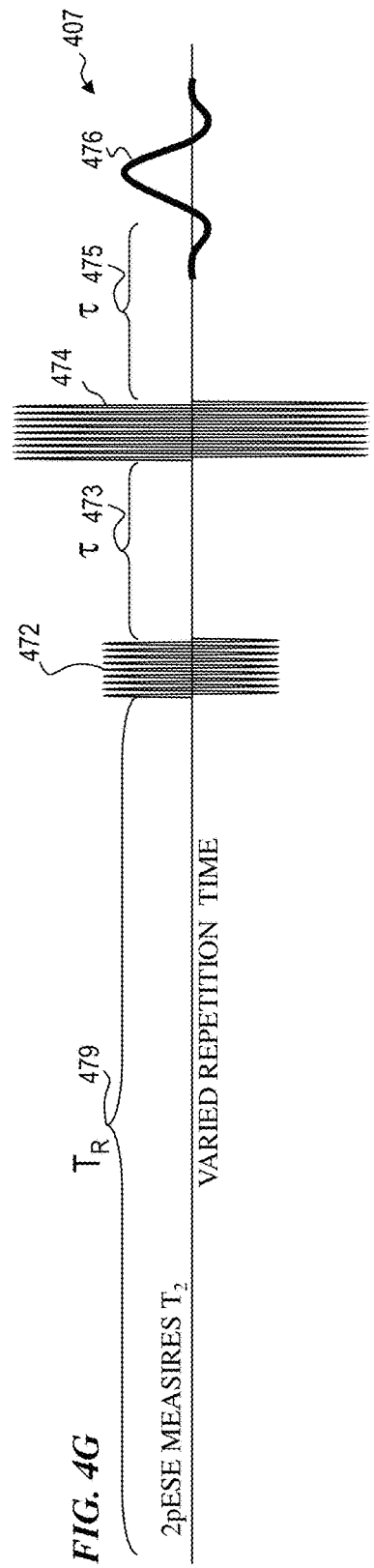
FIG. 4E IRSPI – MEASURES T₂
FIG. 4F SE – MEASURES T₂
FIG. 4G 2pESE MEASURES T₂

EPR OXYGEN IMAGE OF 2 PLANES OF A MOUSE LEG BEARING AN FSA FIBROSARCOMA. COLORBARS SHOW $pO_2$ IN MM/HG (TORR). NUMBERS ON PLANES ARE MM. RESOLUTION: 1 MM SPATIAL, 3 TORR $pO_2$. TUMOR IS *NOT* DISTINGUISHED IN THIS IMAGE BUT SEPARATELY DEFINED USING A REGISTERED $T_2$ MRI INDICATING LARGE CENTRAL OXYGEN GRADIENTS IN THE TUMOR.

$T_{1e}$-SENSITIVE INVERSION-RECOVERY IMAGING FOR EPROI

RELATED APPLICATIONS

This application is a divisional of U.S. patent application Ser. No. 15/213,768 titled "Method and apparatus for $T_{1e}$-sensitive inversion-recovery imaging for EPRI," filed Jul. 19, 2016 by Howard J. Halpern et al. (which issued as U.S. Pat. No. 11,612,336 on Mar. 28, 2023), which is a divisional of U.S. patent application Ser. No. 13/032,637 titled "$T_1$-sensitive inversion-recovery-imaging method and apparatus for EPRI," filed Feb. 22, 2011 by Howard J. Halpern et al. (which issued as U.S. Pat. No. 9,392,957 on Jul. 19, 2016), which claims priority to U.S. Provisional Patent Application 61/306,917 titled "High-isolation transmit/receive surface coils and method for EPRI" filed Feb. 22, 2010 by Howard J. Halpern, U.S. Provisional Patent Application 61/356,555 titled "$T_1$-sensitive inversion recovery imaging apparatus and method for EPRI" filed Jun. 18, 2010 by Howard J. Halpern et al., and U.S. Provisional Patent Application 61/445,037 titled "$T_1$-sensitive inversion recovery imaging method and apparatus for EPRI" filed Feb. 21, 2011 by Howard J. Halpern et al., which are all incorporated herein by reference in their entirety including their appendices.

This application is related to U.S. patent application Ser. No. 13/032,626 titled "High-isolation transmit/receive surface coils and method for EPRI" filed Feb. 22, 2011 by Howard J. Halpern (which issued as U.S. Pat. No. 8,664,955 on Mar. 4, 2014), which is incorporated herein by reference in its entirety.

STATEMENT REGARDING FEDERALLY SPONSORED RESEARCH OR DEVELOPMENT

This invention was made with government support under EB002034, R01 CA098575 awarded by The National Institutes of Health. The government has certain rights in the invention.

FIELD OF THE INVENTION

This invention relates to the field of medical imaging and modeling, and more specifically to a method and apparatus for improved signal-to-noise (S/N) measurements useful for electron paramagnetic resonance imaging (EPRI), in situ and in vivo, using a series of transmitted pulse sets of variously temporally spaced-apart and phase-shifted pulses of transmitted radio frequency (RF) energy that disturb the electron-spin alignment, and then receive the much-weaker resulting RF signal as the electron spins realign to the static magnetic field. The transmitted signal is used in a set of static magnetic-field coils (which generate the electron-spin-aligning constant and gradient magnetic fields) and high-isolation transmit/receive surface, volume, or surface-volume coils that are configured to reduce the reception of the transmitted RF pulses by the receive coils. The received signal is then quadrature decoded (to digitized I values and Q values) using a reference RF signal. In some embodiments, a triplet set of pulses (e.g., in some embodiments, each measurement uses a triplet pulse set of three RF pulses having a selected pulse-to-pulse-to-pulse temporal spacing, a selected set of pulse amplitudes, and various selected phase-shift amounts relative to a reference RF signal, for example:

(1) a first RF "pi" pulse (e.g., about 35 ns of RF (=about 9 cycles of a signal that is about 250 MHz that cause the electron spins to rotate by 180 degrees (pi radians) relative to their orientation in the reference RF signal) of a given "full magnitude" followed, after a first predetermined time delay by (2) a second pulse of about 9 cycles of substantially the same frequency but having half the magnitude (one-quarter the power) and a shifted phase (by one of four different amounts: about 0 degrees, about 90 degrees, about 180 degrees, or about 270 degrees), relative to the cycles of the first pulse (in some embodiments, the cycles of the second pulse are obtained from the same reference RF signal source as those of the first pulse but are phase shifted by the selected amount for that set of three pulses), (the second pulse causes the directions of the electron spins to rotate 90 degrees (pi/2 radians)) and then followed, after a second predetermined time delay, by (3) a third pulse of about nine (9) cycles of substantially the same frequency but having a full magnitude (the same magnitude as the first pulse) and another shifted phase (by one of four different amounts: about 0 degrees, about 90 degrees, about 180 degrees, or about 270 degrees), relative to the cycles of the first pulse (in some embodiments, the approximately nine cycles of the third pulse are also obtained from the same signal source as those of the first pulse but are phase shifted by the selected amount and have the same full magnitude). The second pulse causes the directions of the electron spins to rotate 180 degrees (pi radians), which causes a spin echo of the $T_1$ relaxation signal. The $T_1$ spin echo is temporally separated from the third excitation pulse enough to allow better sensing (better signal-to-noise ratio (SNR)). In some embodiments, a plurality of series of pulses are used, wherein each series has sixteen (16) triplet sets of pulses, wherein each triplet set uses one of four different phase-shift amounts for the second pulse and one of four different phase-shift amounts for the third pulse, and each series uses one of a plurality of predetermined first time delays and one of a plurality of predetermined second time delays. By using pulses that sense the $T_1$ signal rather than the $T_2$ signal, the present invention provides, in some embodiments, improved micro-environmental images that are representative of particular internal structures in the human body and spatially resolved images of tissue/cell protein signals responding to conditions (such as hypoxia) that show the temporal sequence of certain biological processes, and, in some embodiments, that distinguish malignant tissue from healthy tissue.

BACKGROUND OF THE INVENTION

Cells activate protein signaling in response to crucial environmental conditions. Among the best studied is the cellular response to chronically low levels of oxygen, hypoxia. Cells respond to hypoxia by increasing hypoxia inducible factor 1α (HIF1α), a signaling peptide which is the master regulator of hypoxic response. HIF1α promotes genes and their protein products, orchestrating cell, tissue, and organism hypoxic response such as new vessel formation and increase in red cell volume.

U.S. Pat. No. 6,977,502 to David Hertz issued Dec. 20, 2005 titled "Configurable matrix receiver for MRI" is incorporated herein by reference. Hertz describes a configurable matrix receiver having a plurality of antennas that detect one or more signals. The antennas are coupled to a configurable matrix comprising a plurality of amplifiers, one or more switches that selectively couple the amplifiers in series fashion, and one or more analog-to-digital converters (ADCs) that convert the output signals generated by the amplifiers to digital form. For example, a matrix that includes a first amplifier having a first input and a first output, and a second amplifier having a second input and a second output, a switch to couple the first output of the first amplifier to the second input of the second amplifier, a first ADC coupled to the first output of the first amplifier, and a second ADC coupled to the second output of the second amplifier. In one embodiment, the signals detected by the antennas include magnetic resonance (MR) signals.

United States Patent Application Publication 2008/0084210 by Vaughan et al. published Apr. 10, 2008 titled "Multi-Current Elements for Magnetic Resonance Radio Frequency Coils" is incorporated herein by reference. Vaughan et al. disclose a current unit having two or more current paths allows control of magnitude, phase, time, frequency and position of each of element in a radio frequency coil. For each current element, the current can be adjusted as to a phase angle, frequency and magnitude. Multiple current paths of a current unit can be used for targeting multiple spatial domains or strategic combinations of the fields generated/detected by combination of elements for targeting a single domain in magnitude, phase, time, space and frequency.

United States Patent Application Publication 2008/0129298 by Vaughan et al. published Jun. 5, 2008 titled "High field magnetic resonance" is incorporated herein by reference. Vaughan et al. disclose, among other things, multi-channel magnetic resonance using a TEM coil.

An article co-authored by one inventor of the present invention is titled "Imaging radio frequency electron-spin-resonance spectrometer with high resolution and sensitivity for in vivo measurements" by Howard Halpern et al., Rev. Sci. Instrum. 60(6), June 1989, {40. Halpern, 1989 #89} was attached as Appendix B to U.S. Provisional Patent Application 61/306,917 titled "High-isolation transmit/receive surface coils and method for EPRI" filed Feb. 22, 2010 by Howard J. Halpern, which is incorporated herein by reference. Halpern et al. describe a radio frequency (RF) electron-spin-resonance spectrometer with high molar sensitivity and resolution. 250-MHz RF is chosen to obtain good penetration in animal tissue and large aqueous samples.

Another article co-authored by inventors of the present invention is titled "A Versatile High Speed 250-MHz Pulse Imager for Biomedical Applications" by Boris Epel, Sundramoorthy, S. V., Mailer, C. & Halpern, H. J. at the Center for EPR Imaging In Vivo Physiology, Department of Radiation and Cellular Oncology, University of Chicago, Chicago, IL 60637 (Concepts Magn. Reson. Part B (Magn. Reson. Engineering) 33B: 163-176, 2008) {46. Epel, 2008 #2200} was attached as Appendix A to U.S. Provisional Patent Application 61/306,917 titled "High-isolation transmit/receive surface coils and method for EPRI" filed Feb. 22, 2010 by Howard J. Halpern, which is also incorporated herein by reference. Epel et al. describe a versatile 250-MHz pulse electron paramagnetic resonance (EPR) instrument for imaging of small animals. Flexible design of the imager hardware and software makes it possible to use virtually any pulse EPR imaging modality. A fast pulse generation and data acquisition system based on general purpose PCI boards performs measurements with minimal additional delays. Careful design of receiver protection circuitry allowed those authors to achieve very high sensitivity of the instrument. In this article, they demonstrate the ability of the instrument to obtain three-dimensional (3D) images using the electron-spin echo (ESE) and single-point imaging (SPI) methods. In a phantom that contains a 1 mM solution of narrow line (16 µT, peak-to-peak) paramagnetic spin probe, their device achieved an acquisition time of 32 s per image with a fast 3D ESE imaging protocol. Using an 18-min 3D phase relaxation ($T_{2e}$) ESE imaging protocol in a homogeneous sample, a spatial resolution of 1.4 mm and a standard deviation of $T_{2e}$ of 8.5% were achieved. When applied to in vivo imaging this precision of $T_{2e}$ determination would be equivalent to 2 Torr resolution of oxygen partial pressure in animal tissues.

U.S. Pat. No. 4,812,763 to Schmalbein issued Mar. 14, 1989 titled "Electron spin resonance spectrometer", and is incorporated herein by reference. Schmalbein describes an electron spin resonance spectrometer that includes a resonator containing a sample and arranged in a magnetic field of constant strength and high homogeneity. A microwave bridge can be supplied with microwave energy in the form of an intermittent signal. Measuring signals emitted by the resonator are supplied to a detector and a signal evaluation stage. A line provided between a microwave source and the microwave bridge is subdivided into parallel pulse-shaping channels, one of them containing a phase shifter, an attenuator and a switch for the signal passing through the pulse-shaping channels. In order to be able to set, if possible, an unlimited plurality of pulse sequences for experiments of all kinds, the pulse-shaping channels are supplied in equal proportions from the line by means of a divider. All pulse-shaping channels are provided with a phase shifter and an attenuator. The pulse-shaping channels are re-united by means of a combiner arranged before the input of a common microwave power amplifier.

U.S. Pat. No. 6,639,406 to Boskamp, et al. issued Oct. 28, 2003 titled "Method and apparatus for decoupling quadrature phased array coils", and is incorporated herein by reference. Boskamp, et al. describe a method and apparatus for combining the respective readout signals for a loop and butterfly coil pair of a quadrature phased array used for magnetic resonance imaging. The technique used to combine the signals introduces a 180-degree phase shift, or multiple thereof, to the loop coil signal, thereby allowing the loop coil signal to be decoupled from other loop coil signals by a low-input-impedance preamplifier in series with the signal. This patent describes a surface coil that is applied to one surface of the body part being examined.

U.S. Pat. No. 7,659,719 to Vaughan, et al. issued Feb. 9, 2010 titled "Cavity resonator for magnetic resonance systems", and is incorporated herein by reference. Vaughan, et al. describe a magnetic resonance apparatus that includes one or more of the following features: (a) a coil having at least two sections, (b) the at least two sections having a resonant circuit, (c) the at least two sections being reactively coupled or decoupled, (d) the at least two sections being separable, (e) the coil having openings allowing a subject to see or hear and to be accessed through the coil, (f) a cushioned head restraint, and (g) a subject input/output device providing visual data to the subject, the input/output device being selected from the group consisting of mirrors, prisms, video monitors, LCD devices, and optical motion trackers. This patent describes a volume head coil that surrounds a human head.

U.S. Pat. No. 5,706,805 Swartz, et al. issued Jan. 13, 1998 titled "Apparatus and methodology for determining oxygen tension in biological systems", and is incorporated herein by reference. Swartz, et al. describe apparatus and methods for measuring oxygen tensions in biological systems utilizing physiologically acceptable paramagnetic material, such as India ink or carbon black, and electron paramagnetic resonance (EPR) oximetry. India ink is introduced to the biological system and exposed to a magnetic field and an electromagnetic field in the 1-2 GHz range. The EPR spectrum is then measured at the biological system to determine oxygen concentration. The EPR spectrum is determined by an EPR spectrometer that adjusts the resonator to a single resonator frequency to compensate for movements of the biological system, such as a human or animal. The biological system can also include other in vivo tissues, cells, and cell cultures to directly measure $pO_2$ non-destructively. The paramagnetic material can be used non-invasively or invasively depending on the goals of the $pO_2$ measurement. A detecting inductive element, as part of the EPR spectrometer resonator, is adapted relative to the measurement particularities.

U.S. Pat. No. 5,865,746 to Murugesan, et al. issued Feb. 2, 1999 titled "In vivo imaging and oxymetry by pulsed radiofrequency paramagnetic resonance", and is incorporated herein by reference. Murugesan et al. describe a system for performing pulsed RF FT EPR spectroscopy and imaging includes an ultra-fast excitation subsystem and an ultra-fast data acquisition subsystem. Additionally, method for measuring and imaging in vivo oxygen and free radicals or for performing RF FT EPR spectroscopy utilizes short RF excitations pulses and ultra-fast sampling, digitizing, and summing steps.

U.S. Pat. No. 4,280,096 to Karthe, et al. issued Jul. 21, 1981 titled "Spectrometer for measuring spatial distributions of paramagnetic centers in solid bodies", and is incorporated herein by reference. Karthe, et al. describe a spectrometer in which gradient coils are provided in order to create an inhomogeneous magnetic field for use in analyzing individual regions within the sample under examination. The gradient coils and the modulating coils are operated by discrete pulses, rather than continuously. A keying unit coordinates the interaction of the various components of the spectrometer in order to monitor resonance of the sample under examination while such pulses occur.

U.S. Pat. No. 5,828,216 to Tschudin, et al. issued Oct. 27, 1998 titled "Gated RF preamplifier for use in pulsed radiofrequency electron paramagnetic resonance and MRI", and is incorporated herein by reference. Tschudin et al. describe a gated RF preamplifier used in system for performing pulsed RF FT EPR spectroscopy and imaging or MRI. The RF preamplifier does not overload during a transmit cycle so that recovery is very fast to provide for ultra-fast data acquisition in an ultra-fast excitation subsystem. The preamplifier includes multiple low-gain amplification stages with high-speed RF gates inserted between stages that are switched off to prevent each stage from overloading during the transmit cycle.

U.S. Pat. No. 4,714,886 to one of the present inventors, Howard Halpern, issued Dec. 22, 1987 titled "Magnetic resonance analysis of substances in samples that include dissipative material", and is incorporated herein by reference. U.S. Pat. No. 4,714,886 describes magnetic resonance images of the distribution of a substance within a sample that are obtained by splaying a pair of magnetic field generating coils relative to each other to generate a magnetic field gradient along an axis of the sample. In other aspects, electron spin resonance data is derived from animal tissue, or images are derived from a sample that includes dissipative material, using a radio frequency signal of sufficiently low frequency.

There is a need for an improved apparatus and method of electron-spin-resonance spectrometry and/or imaging to non-invasively provide images and/or other signal measurements representative of particular internal structures and processes in the human body, and to be able to distinguish malignant tissue from healthy tissue.

SUMMARY OF THE INVENTION

The present invention provides a method and apparatus for improved signal-to-noise (S/N) measurements useful for electron paramagnetic resonance imaging (EPRI), in situ and in vivo, using high-isolation transmit/receive surface coils and a series of pulse sets of variously temporally spaced-apart and phase-shifted pulses of RF energy. In some embodiments, a plurality of measurements are taken and recorded, wherein each measurement is based on establishing a static (DC) magnetic field on an animal tissue (e.g., a magnetic field having a substantially fixed direction and a gradient field strength in a section of volume of tissue of a living human), then transmitting a set of RF pulses that includes a first pulse, a first delay, a second pulse, a second delay and a third pulse, and then receiving, processing, and storing the resultant RF signals from the tissue sample. By varying the strength of the DC magnetic field (e.g., by generating the magnetic-field gradient that increases the field strength in some areas of the tissue being measured and/or decreases the field strength in other areas of the tissue being measured) and varying the direction of the gradient relative to the tissue being measured (e.g., by electromagnetically changing the direction of the gradient, or by physically moving the patient relative to the gradient), varying the durations of the first and second delays, and varying the amounts of phase shifts of the second and third pulses relative to the phase of the first pulse, and storing that data along with data based on the RF signal received from the sample, an image (e.g., two-dimensional (2D) sections in various orientations, or a three-dimensional (3D) image of a volume) of the section or volume of tissue can be derived by computer calculations and displayed. For example, in some embodiments, each measurement uses a pulse set of three RF pulses having a selected temporal spacing, selected amplitudes, and various phase-shift amounts, for example: a first RF pulse (e.g., in some embodiments, a pulse of about 35-ns duration, which equals about 9 cycles of about 250 MHz cycles) followed after a first variable delay by a second pulse (e.g., of about 9 cycles of substantially the same frequency but having half the amplitude and a shifted phase relative to the cycles of the first pulse; in some embodiments, the cycles of the second pulse are obtained from the same signal source as those of the first pulse but are either not phase shifted (which is equivalent to phase shifted by 0 degrees), phase shifted by 90 degrees, phase shifted by 180 degrees, or phase shifted by 270 degrees, then followed, after a second variable delay, by a third pulse of about 9 cycles of substantially the same frequency but having the same amplitude as the first pulse and a variously shifted phase relative to the cycles of the first pulse. In some embodiments, the first pulse has a magnitude that flips the electron-spin directions (the direction of magnetization) by 180 degrees and is thus called a "pi pulse"; the second pulse has a magnitude that flips the electron-spin directions (the direction of magnetization) by 90 degrees and is thus called a "pi-over-two pulse" (or "pi/2 pulse"); and the third pulse has a magnitude that again flips the electron-spin directions (the direction of magnetization) by 180 degrees and is thus called a "pi pulse". In some embodiments, these triplet sets of excitation RF pulses are configured to result in signals that represent the $T_1$ relaxation of electron spin (in contrast to the $T_2$ relaxation of electron spin) in order to be sensitive to the oxygen content in the tissue being imaged. In some such embodiments, the four possible phase-shift amounts of the second pulse and the four possible phase-shift amounts of the third pulse provide sixteen combinations of phase shift amounts for each set of the first delay (between the first and second pulses) and second delay (between the second and third pulses). In some embodiments, this provides improved SNR in micro-environmental images that are representative of particular internal structures in the human body and spatially resolved images of tissue/cell protein signals responding to conditions (such as hypoxia) that show the temporal sequence of certain biological processes, and, in some embodiments, that distinguish malignant tissue from healthy tissue.

In some embodiments, the durations of the three pulses in a triplet set are kept constant and the frequency of the carrier in each pulse are kept constant in order to maintain the same spectral content (i.e., the Fourier transform of the pulses yields the same spectrum of frequencies and relative strengths for those frequencies) for every pulse, while the total strength of some of the pulses is varied to obtain different amounts of rotation of the electron spins and/or magnetic moment of the reporter molecules.

In some embodiments, the present invention further includes medical procedures, animal models, and biological agents (such as viral "Trojan Horse" constructs or other vectors) that facilitate the obtaining of images that distinguish different types of tissues or healthy tissues from malignant or infected tissues, that show various spatially and temporally resolved signaling, regulation, promotion and responses of, for example, signaling peptides, protein products.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A1 shows a schematic representation of an inversion-recovery pulse sequence 101 useful for measuring $T_1$, according to some embodiments of the present invention.

FIG. 1B1 shows a schematic representation of a conventional saturation-recovery-with-echo-detection pulse sequence 102 useful for measuring $T_1$.

FIG. 1C1 shows a schematic representation of a 2pESE pulse sequence 103 useful for measuring $T_2$, according to some embodiments of the present invention.

FIG. 1A2 shows another schematic representation of inversion-recovery pulse sequence 101 useful for measuring $T_1$, according to some embodiments of the present invention.

FIG. 1B2 shows another schematic representation of conventional saturation-recovery-with-echo-detection pulse sequence 102 useful for measuring $T_1$.

FIG. 1C2 shows another schematic representation of 2pESE pulse sequence 103 useful for measuring $T_2$, according to some embodiments of the present invention.

FIG. 2 is a graph 201 of spectroscopic measurements of the effective spin-packet linewidth versus spin-probe concentration.

FIG. 4A shows an SFR ESE pulse sequence, wherein the repetition rate is varied.

FIG. 4B shows an SFR SPI pulse sequence, wherein the repetition rate is varied.

FIG. 4C shows a saturation-recovery-with-echo-detection (SR) pulse sequence, wherein the delay time T is varied.

FIG. 4D1 shows an IRESE pulse sequence using a pi/2-pi echo-detecting pulse pair, wherein the delay time T is varied.

FIG. 4D2 shows an IRESE pulse sequence with a pi/2-pi/2 echo-detecting pulse pair, wherein the delay time T is varied.

FIG. 4E shows an IRSPI pulse sequence, wherein the delay time T is varied.

FIG. 4F shows an SE pulse sequence, wherein the delay time T is varied.

FIG. 4G shows a two-pulse electron-spin echo (2pESE) sequence measuring $T_1$ by varying repetition time.

DESCRIPTION OF PREFERRED EMBODIMENTS

Figure 1D:
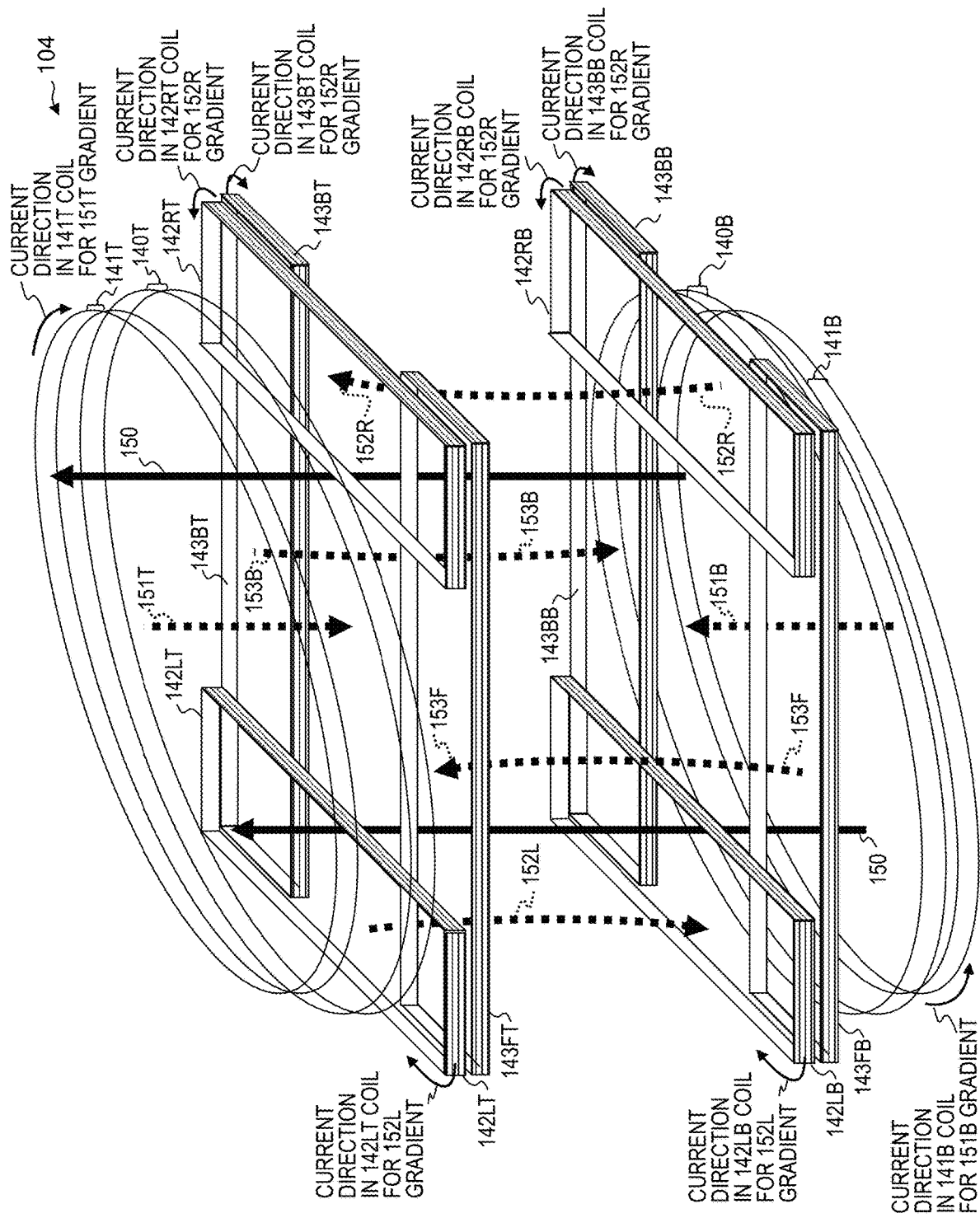
FIG. 1D is a perspective schematic representation of a gradient-field set 104 of electromagnet coils useful for measuring $T_1$, according to some embodiments of the present invention.

Although the following detailed description contains many specifics for the purpose of illustration, a person of ordinary skill in the art will appreciate that many variations and alterations to the following details are within the scope of the invention. Accordingly, the following preferred embodiments of the invention are set forth without any loss of generality to, and without imposing limitations upon, the claimed invention. Further, in the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

Section #1: $T_1$ Imaging

Virtually all pulse-EPR imaging in animal specimens has used sequences sensitive to transverse relaxation times of the electron spin probe, $T_2$. {110. Matsumoto, 2006}, {46. Epel, 2008 #2200}. $T_2$ is a measure of phase coherence that takes place as a result of quantum-mechanical spin flips caused by multiple interactions with the environment. As has been demonstrated in nuclear-magnetic-resonance imaging and spectroscopy, and water-proton MRI, $T_2$ relaxation is sensitive not only to the loss of energy by the spin system to the environment (spin lattice) but multiple other relaxation processes that can affect the phase coherence of the magnetization spins as well as the loss of energy. Among these relaxation processes are interactions, in animal tissue, with oxygen, a di-radical with two unpaired electrons in its outermost orbital. This both dephases the spins of the reporter spin system but results in loss of energy from the reporter spin system.

One of the major confounding and blurring effects of using $T_2$ imaging for oxygen measurement is the confounding spin dephasing by one molecule of the reporter system by another reporter molecule. These cannot be distinguished in a $T_2$ measurement of oxygen dephasing of the reporter spin system.

$T_2$ measurements are also known as transverse-spin-relaxation time (or sometimes spin-spin relaxation time) measurements. $T_1$ measurements are also known as longitudinal-spin-relaxation-time measurements. In principle, $T_1$ only measures the loss of energy by the reporter spin system to the environment, also known as the lattice, and thus $T_1$ is also called the spin-lattice relaxation time (SLR time), while $T_2$ is also called spin-spin relaxation time. This requires that the mechanism(s) that can relax the longitudinal spins are much more restricted than those that relax the transverse spin component. $T_1$-spin relaxation is thereby a more specific process. An example, in principle, is that when energy is transferred from one reporter spin molecule to another, the reporter spin system loses no energy. There is no relaxation. Thus, the $T_1$ measurement should be far less sensitive to self interaction than the $T_2$ measurement.

The present invention has obtained the first $T_1$-based tissue-oxygen image using $T_1$-sensitive inversion recovery using spin-echo detection of the spin recovery. This gives longer relaxation times, which will provide an even more direct sensitivity to $pO_2$.

Two modalities for determination of $T_1$ are commonly used in pulse EPR: saturation and inversion recovery. In the first case, presented in the FIG. 1B1, the EPR transition is saturated with a long (t>>$T_1$) RF pulse and recovery of EPR signal is detected as a function of separation between this pulse and detection sequence (two pulse echo in this case). For inversion recovery (FIG. 1A1), a π-pulse (pi pulse) is used to invert the magnetization. We have implemented the inversion-recovery method since it has a twice larger effect and does not require additional hardware. In some embodiments, for projection generation, which acts as a "read out" of the $T_1$ information, the present invention uses the electron-spin echo (ESE)-detection sequence.

In an EPR system, the magnetic moment will generally align with the $H_0$ static magnetic field (conventionally and as used herein the direction of $H_0$ is designated as the z direction), but will precess at an angular frequency ω that is proportional to $H_0$, and there exists a particular angular frequency $\omega_R$ that is resonant for a particular magnitude of $H_0$. If an alternating magnetic field $H_1$ cos(ωt) (designated $H_1$ for simplicity, conventionally and as used herein the direction of $H_1$ is designated as the x direction) is applied orthogonal to the $H_0$ static magnetic field, where ω is at the resonant angular frequency $\omega_R$, a magnetic moment that was parallel to the $H_0$ static magnetic field will precess in the y-z plane; that is, the magnetic moment will precess but always remain perpendicular to the $H_1$ (x direction) alternating field, and thus will periodically be pointed in a direction opposite $H_0$. If a wave train (a radio-frequency (RF) pulse) were applied at a magnitude A and for a pulse duration $t_w$, the magnetic moment will precess through an angle $\theta = AH_1 t_w$. If an RF pulse of a selected magnitude A and pulse duration $t_w$ is applied such that θ=π (i.e., θ=180 degrees), the pulse will invert the magnetic moment and such a pulse is called a π pulse (also called a 180-degree pulse). Further, if an RF pulse of a different selected magnitude A' and pulse duration $t_w$ is applied such that θ=π/2 (i.e., θ=90 degrees), the pulse will turn the magnetic moment from the z direction to the y direction and such a pulse is called a π/2 pulse (also called a 90-degree pulse). Note that either or both the magnitude A and pulse duration $t_w$ may be varied to achieve a given desired rotation of the magnetic moment. (See Charles P. Slichter "Principles of Magnetic Resonance, Third Enlarged and Updated Edition", Springer Berlin-Heidleberg, 1996, pp 20-24.) Other pulses of selected magnitudes A and pulse durations $t_w$ may be used to achieve other amounts of rotation of the magnetic moment, such as a 2π/3 pulse (also called a 120-degree pulse).

FIG. 1A1 shows a schematic representation of an inversion-recovery pulse sequence 101 that includes a first π pulse (also called a pi pulse, inversion pulse or 180-degree pulse) 110, a first time delay "T" 111 after first π pulse (pi pulse) 110, then a second π/2 pulse (pi/2 pulse or 90-degree pulse) 112, a second time delay "τ" 113 after second π/2 pulse (pi/2 pulse) 112; then a third π pulse (pi pulse or 180-degree pulse) 114, a third time delay "τ" 115 after third π pulse (pi pulse) 114; then a readout-stage measurement 116 of the resulting spin echo. This pulse sequence is referred to herein as an inversion recovery sequence with electron-spin echo detection, or IRESE. The dashed line 127 shows signal amplitude (arbitrary units; not to scale) of the spin echo as a function of time. In both cases (FIG. 1A1 and FIG. 1B1), the detection sequence consists of two ESE pulses: a π/2 pulse (pi/2 pulse or 90-degree pulse) and a π pulse (pi pulse or 180-degree pulse). Note that the durations of the pulses as shown in FIG. 1A1, FIG. 1B1, and FIG. 1C1 are not to scale with the times between pulses or times between pulse sequences. In some embodiments, the pulse durations are chosen as 35 ns (nanoseconds) each (substantially square pulses of about 9 cycles of a 250 MHz carrier wave), while the time τ 113 between the π/2 pulse 112 and the π pulse 114 is chosen as τ=630 ns, and T 111 is varied for a given set of signal acquisitions at eight values, denoted as variable delay or VD in the IRESE section of Table 1 below, logarithmically spaced between 0.5 μs (500 ns) and 16 μs (16,000 ns). Further, the magnitudes of the readout signals 116, 126, and 136 are not to scale with the magnitude of the excitation pulses 110, 112, 114, 120, 122, 124, 132, or 134.

Pulse 112 and pulse 114 are also referred to as "readout pulses". In some other embodiments, rather than using a π/2 pulse (90-degree pulse) and a π pulse (180-degree pulse) as the readout pulses, two pulses, each being a 2π/3 pulse (120-degree pulse), are used instead as the readout pulses for an inversion-recovery measurement of $T_1$. The original spin echo measurements of Erwin Hahn, which were generated by two π/2 pulses, could also be used for the readout of the magnetization after an initial inversion pulse FIG. 1B1 shows a schematic representation of a saturation-recovery-with-echo-detection (SR) pulse sequence 102 that includes a first saturation pulse 120, a first time delay "T" 111 after first saturation pulse 120, then a second π/2 pulse (pi/2 pulse or 90-degree pulse) 122, a second time delay "τ" 123 after the second pulse 122; then a third π pulse (pi pulse or 180-degree pulse) 124, a third time delay "τ" 125 after the third pulse 124; then a readout-stage measurement 126 of the resulting spin echo. The dashed line 127 shows relative signal amplitude (arbitrary units; not to scale) of the spin echo as a function of time.

FIG. 1C1 shows a schematic representation of a 2pESE pulse sequence 103 useful for measuring $T_2$, wherein pulse sequence 103 includes a first π/2 pulse 132, a first time delay "τ" 133 after the first pulse 132; then a second π pulse 134, a second time delay "τ" 135 after the second pulse 134; then a readout-stage measurement 136 of the resulting spin echo. The delay time $T_R$ 139 is the time between the end of one signal-acquisition phase (e.g., of signal 136) and the start of the next first pulse 132. The dashed line 127 shows signal amplitude (arbitrary units; not to scale) of the spin echo as a function of time.

Figure 2:
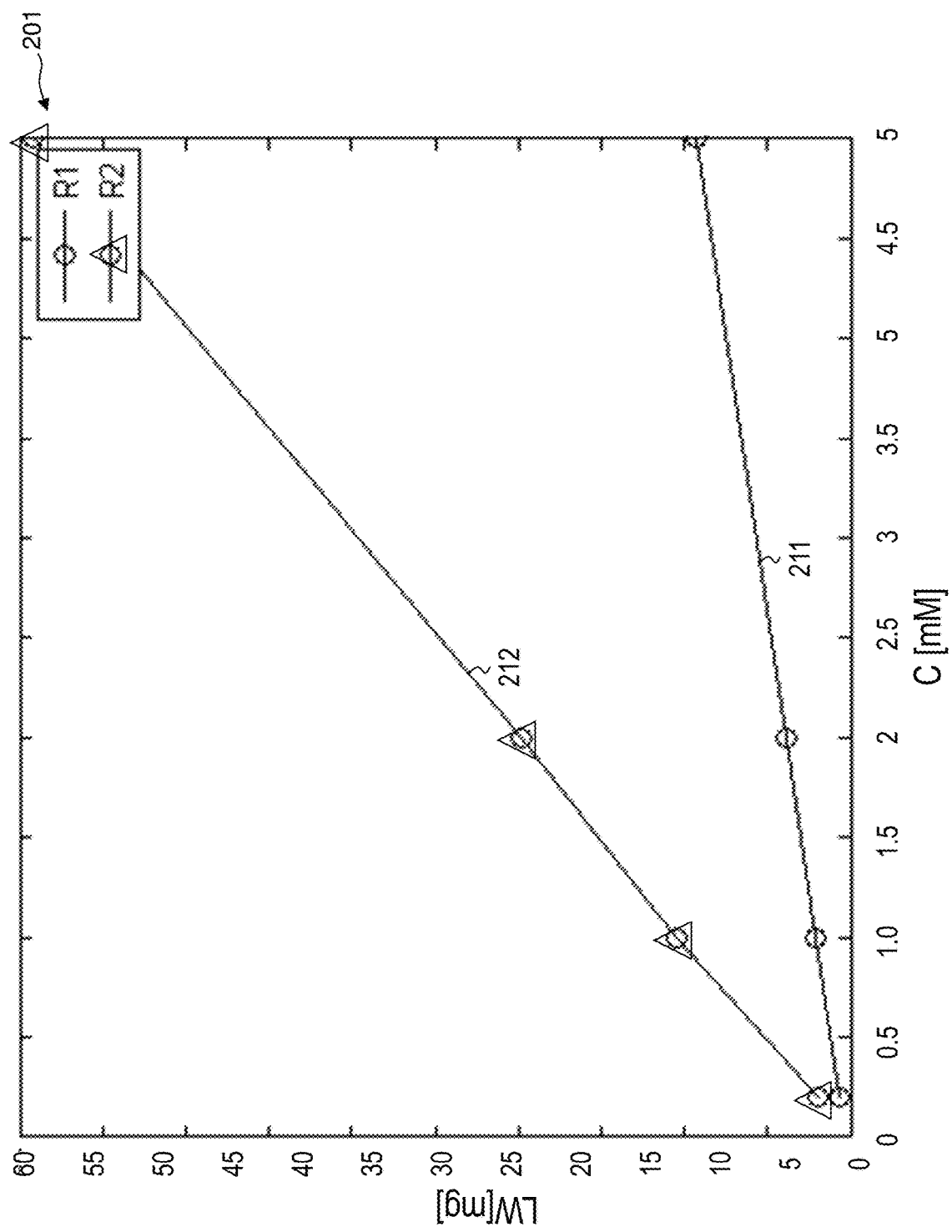

FIG. 1A2 shows another schematic representation of inversion-recovery pulse sequence 101 useful for measuring $T_1$, according to some embodiments of the present invention. Note that the durations of the pulses as shown in FIG. 1A2, FIG. 1B2, and FIG. 1C2 are more to scale with the times between pulses or times between pulse sequences. In some embodiments, as described above, the pulse durations are chosen as 35 ns (nanoseconds) each (substantially square pulses of about 9 cycles of a 250 MHz carrier wave), while the time τ 113 between the π/2 pulse 112 and the π pulse 114 is chosen as τ=630 ns, and T 111 is varied for a given set of signal acquisitions at eight values, denoted as VD in the IRESE section of Table 1 below, logarithmically spaced between 0.5 μs (500 ns) and 16 μs (16000 ns). Further, the magnitudes of the readout signals 116, 126, and 136 are not to scale with the magnitude of the excitation pulses 110, 112, 114, 120, 122, 124, 132, or 134.

FIG. 1B2 shows another schematic representation of conventional saturation-recovery-with-echo-detection pulse sequence 102 useful for measuring $T_2$, where the durations of the pulses and the times between pulses are more to scale than in FIG. 1B1.

FIG. 1C2 shows another schematic representation of 2pESE pulse sequence 103 useful for measuring $T_1$, according to some embodiments of the present invention, where the durations of the pulses and the times between pulses are more to scale than in FIG. 1C1.

FIG. 1D is a perspective schematic representation of a gradient-field set 104 of electromagnet coils useful for measuring $T_1$, according to some embodiments of the present invention. In some embodiments, the planes of all of the rectangular coils (coil 142LT (the left-hand top coil in FIG. 1D), coil 142RT (the right-hand top coil in FIG. 1D), coil 142LB (the left-hand bottom coil in FIG. 1D), coil 142RB (the right-hand bottom coil in FIG. 1D), coil 143FT (the front top coil in FIG. 1D), coil 143BT (the back top coil in FIG. 1D), coil 143FB (the front bottom coil in FIG. 1D), coil 143BB (the back bottom coil in FIG. 1D), are parallel to one another and these planes in turn are parallel to the planes of the round coils. This is to make the main direction of the magnetic fields of each given strength in the region of interest parallel. In some embodiments, the planes of the pairs of similarly oriented square coils, for example, above the horizontal plane, are offset a little bit so that these rectangular coil pairs can be moved closer to each other without bumping each other. In some embodiments, the distances between members of each pair are reduced to make the gradient (the amount of change in magnetic field strength) more uniform.

In some embodiments, the currents in each coplanar pair move in opposite senses. For example, in the embodiment shown in FIG. 1D, the current in coil 141T is clockwise such that the differential field 151T is downward (subtracting from the main field 150 on the top side), while the current in coil 141B is counterclockwise such that the differential field 151B is up (adding to the main field 150 on the back side). By changing the magnitude of the currents in coils 141T and 141B the amount of gradient can be varied. Similarly, in the embodiment shown, the current in coils 142LT and 142LB are clockwise such that the differential field 152L is downward (subtracting from the main field 150 on the left-hand side), while the current in coils 142RT and 142RB are counterclockwise such that the differential field 152R is upward (adding to the main field 150 on the right-hand side); and the current in coils 143FT and 143FB are counterclockwise such that the differential field 153F is upward (adding to the main field 150 on the front side), while the current in coils 143BT and 143BB are clockwise such that the differential field 153B is downward (subtracting from the main field 150 on the back side). By changing the directions and the relative and absolute amounts of current in the three sets of coils, the gradient-field direction and magnitude can be changed in plus and/or minus X, Y and/or Z directions.

In some embodiments of the gradient-field coils, there are left and right coplanar pairs (142LB and 142RB) that face the corresponding coils (142LT and 142RT) above the horizontal midplane, and front and back coplanar pairs (143FB and 143BB) of coils below the horizontal midplane that face the corresponding coils (143FT and 143BT) above the horizontal midplane. In some embodiments (not shown here), for each pair of the gradient-field coils (142LB and 142RB), (142LT and 142RT), (143FB and 143BB) (143FT and 143BT) there are an outside set of two pairs and an inside set of two pairs, one set closer—the other set farther apart. The coils that face each other across the horizontal have their currents in the same direction. FIG. 2 presents a graph 201, where plot 211 shows $1/T_1$, the longitudinal relaxation rate of the magnetization described in terms of magnetic-field linewidth units to which it is proportional versus spin-probe concentration as measured using an inversion-recovery pulse sequence 101, and plot 212 shows $1/T_2$, the transverse relaxation rate of the magnetization described in terms of a magnetic field linewidth to which it is proportional versus spin-probe concentration as measured using a spin echo pulse sequence decay 103.

FIG. 2 presents a graph 201 of spectroscopic measurements of a the effective spin-packet linewidth versus spin-probe concentration of deoxygenated samples of spin probe (OX063 radical methyl-tris[8-carboxy-2,2,6,6-tetrakis[2-hydroxyethyl]benzo[1,2-d:4,5-d']bis[1,3]dithiol-4-yl]-trisodium salt, molecular weight=1,427 from GE Healthcare, Little Chalfont, Buckinghamshire, United Kingdom). In some embodiments, the solvent for the spin probe is saline. All measurements are made at the same oxygen partial pressure, 0 torr. Plot 211 shows the $T_1$ spin-packet linewidth versus spin-probe concentration as measured using an inversion-recovery (IRESE) pulse sequence 101 (see FIG. 1A1) according to the present invention, while plot 212 shows the $T_2$ spin-packet linewidth versus spin-probe concentration as measured using a saturation-recovery-with-echo-detection pulse sequence 102 (see FIG. 1B1). Note that at low spin-probe concentrations, the $T_1$ and $T_2$ measurements give approximately the same linewidth. However, as concentration of spin probe rises, the additional confounding width of the $T_1$ measurements is reduced, and is only about one-fifth (⅕) that of the $T_2$ measurements. This is a remarkable reduction in the sensitivity of linewidth (or relaxation time) to the confounding variation of the concentration of spin probe. That is, the linewidth increase (i.e., error and/or uncertainty due to spin-probe concentration increase) is about five times worse at high spin-probe concentrations if measuring $T_2$ using saturation-recovery-with-echo-detection pulse (SR) sequence 102 than if measuring $T_1$ using an inversion-recovery pulse (IRESE) sequence 101.

Figure 3A:
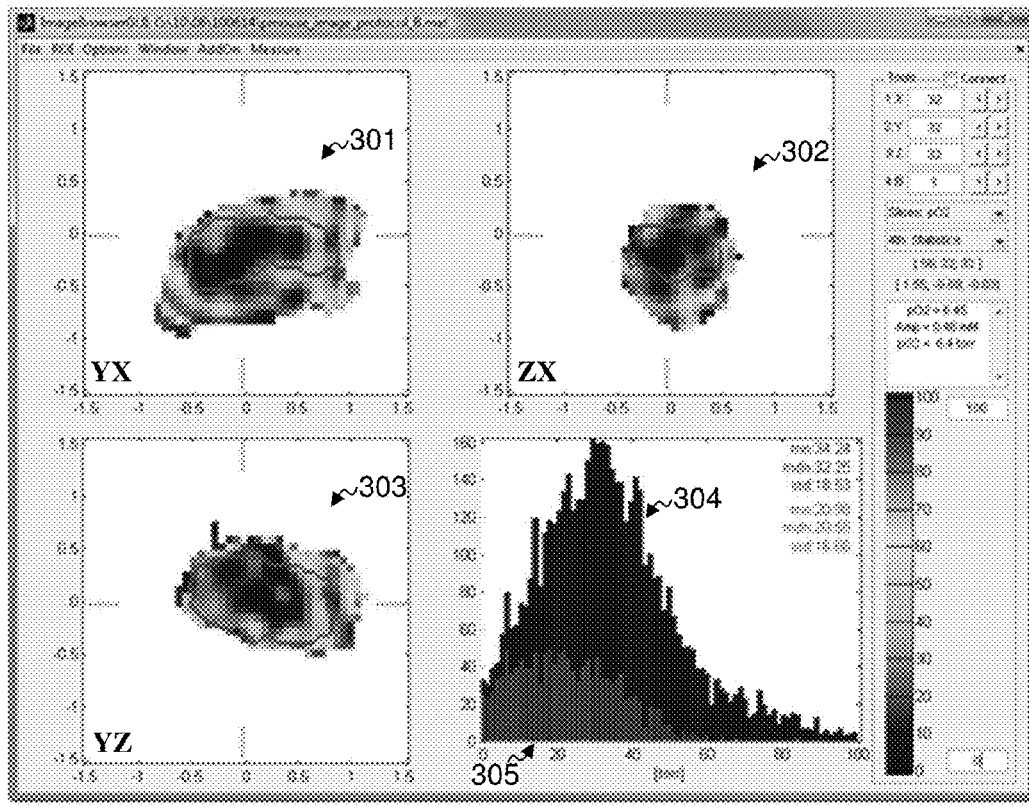
FIG. 3A and FIG. 3B present $1/T_2$ and $1/T_1$ images, respectively, obtained from a mouse tumor, presented on the same drawing sheet for comparison.
Figure 3B:
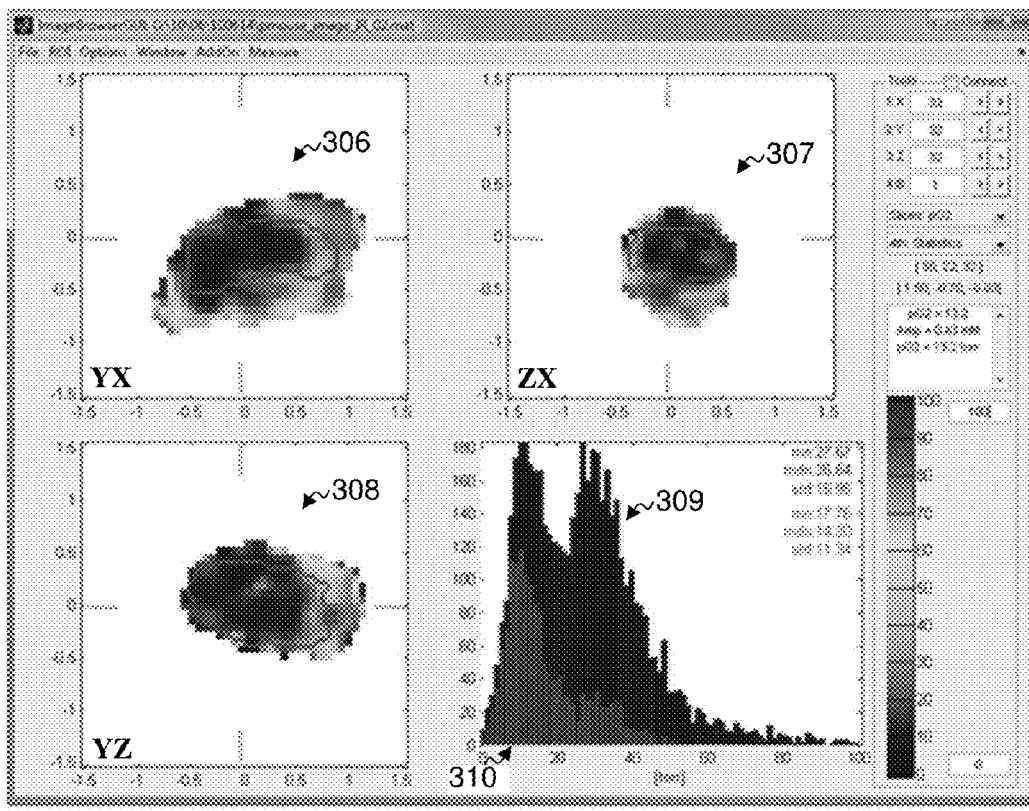
Figure 3C:
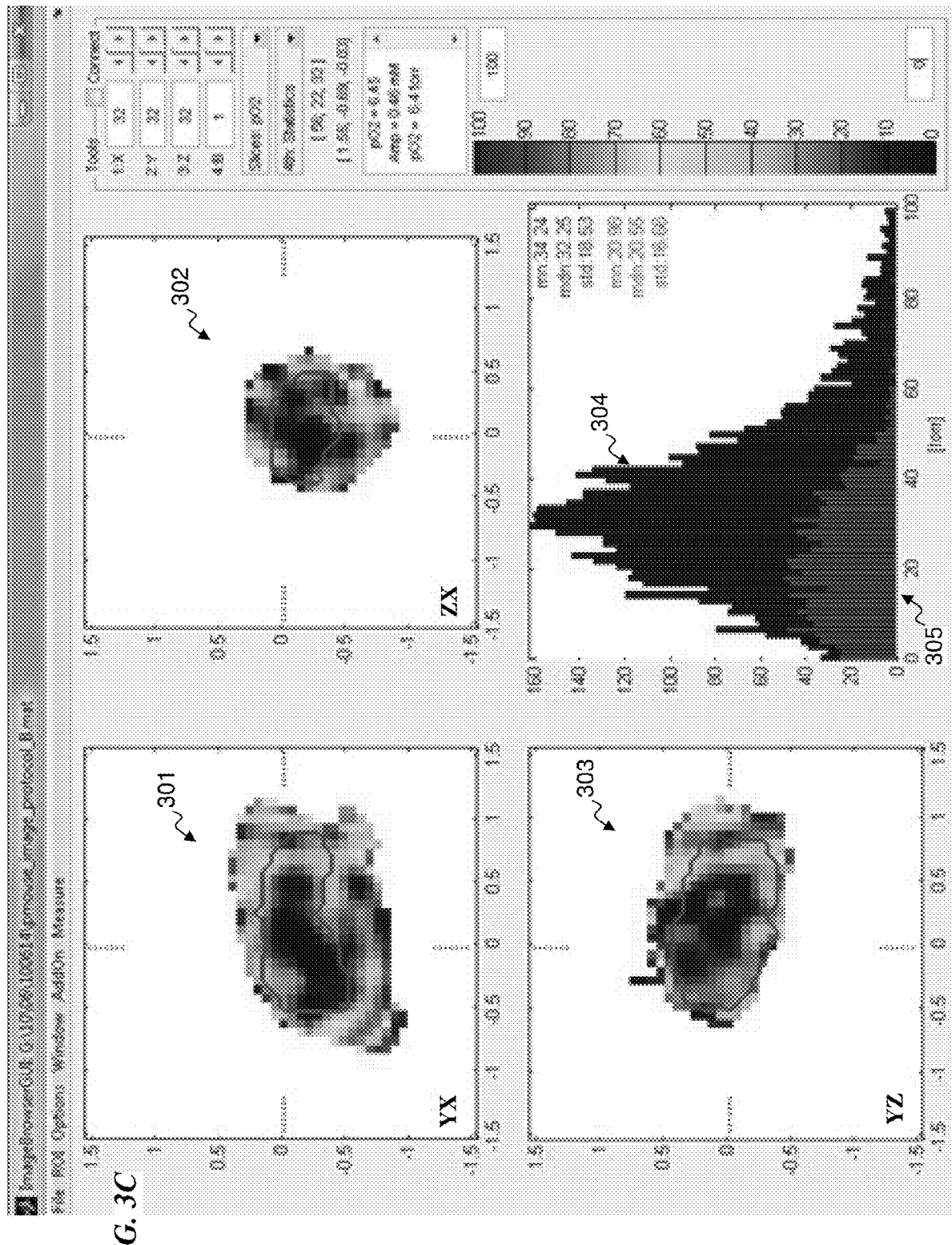
FIG. 3C is an enlarged view of the screenshot of the $1/T_2$ images of FIG. 3A.

FIG. 3A and FIG. 3B present $T_2$ and $T_1$ images obtained from the same tumor, presented on the same drawing sheet for comparison. FIG. 3C is an enlarged view of the screenshot of FIG. 3A, and FIG. 3D is an enlarged view of the screenshot of FIG. 3B.

FIG. 3A and FIG. 3C each show, at different magnifications, the same orthogonal $T_2$ EPR image planes 301, 302 and 303 (labeled YX, ZY and YZ respectively) from an C57/B mouse leg bearing a syngeneic B16 melanoma. The red contour line in each view is that of the tumor from obtained from a spatially registered MRI (a conventional nuclear magnetic resonance image). Spin-packet linewidth derived $pO_2$ from the whole leg are histogrammed in blue plot 304 and those only from the tumor are in red plot 305.

Figure 3D:
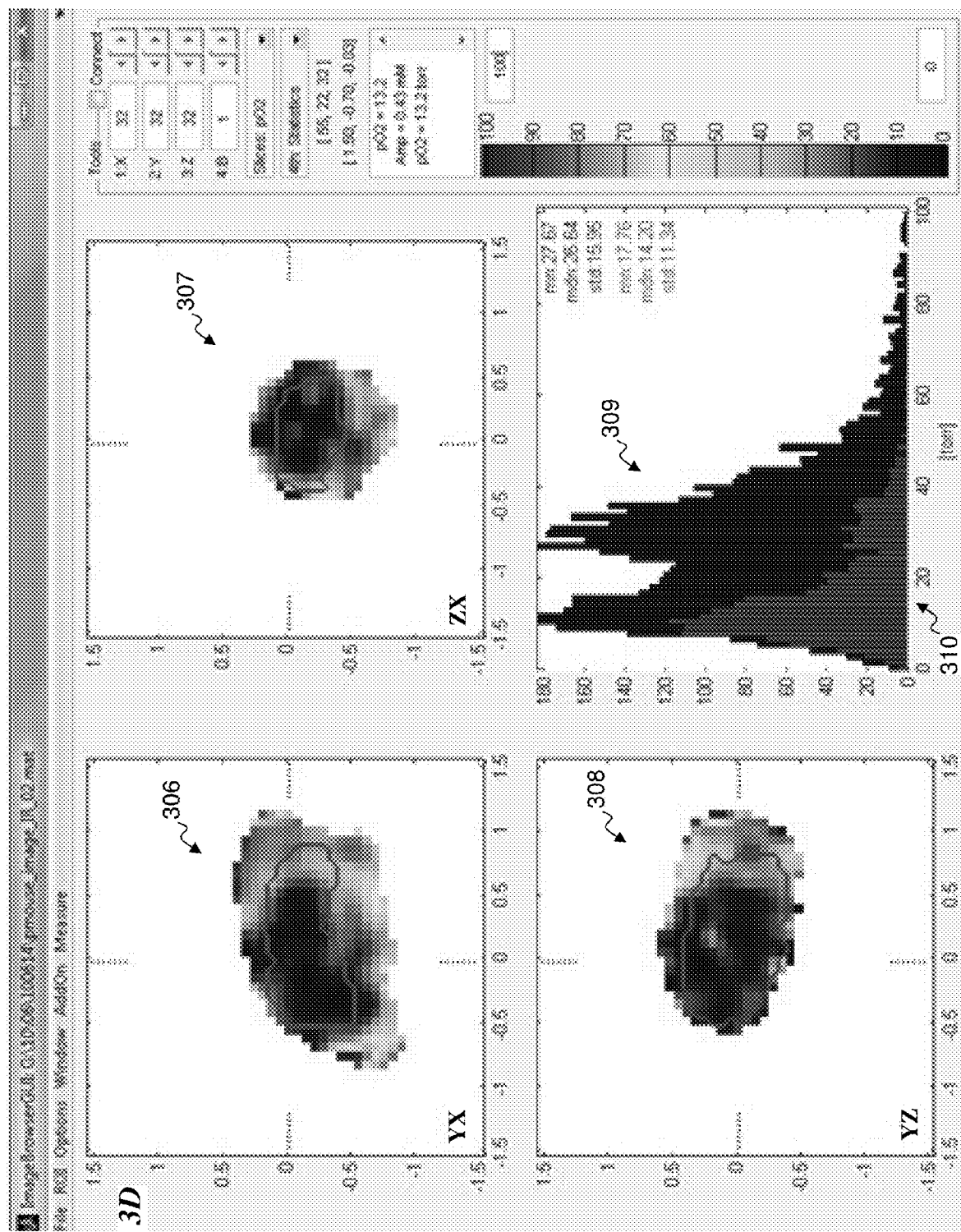
FIG. 3D is an enlarged view of the screenshot of the $1/T_1$ images of FIG. 3B.

FIG. 3B and FIG. 3D each show, at different magnifications, the same orthogonal $T_1$ EPR image planes 306, 307 and 308 (labeled YX, ZY and YZ respectively) from the same C57/B mouse leg bearing the syngeneic B16 melanoma. The red contour line in each view is that of the tumor from a conventional nuclear MRI. Spin-packet linewidth derived $pO_2$ from the whole leg are histogrammed in blue plot 309 and those only from the tumor are in red plot 310.

From the histograms 304, 305 of the $pO_2$ values derived from the $T_2$ images and the histograms 304, 305 of the $pO_2$ values derived from the $T_1$ images one can see a clear separation of the hypoxic tumor $pO_{25}$ in the $T_1$ image which is blurred in the $T_2$ image. This is due to the reduced confounding effect of spin probe concentration on the images.

Section #2: Further $T_1$ Imaging Techniques— a. Significance—Oxygen, HIF1α, VEGF and cancer biology: Regions of low $pO_2$-hypoxia—are characteristic of solid tumors and have long been known to increase resistance of malignant cells to radiation {1. Hall, 2000 #1012; 2. Gatenby, 1988 #21; 3. Brizel, 1996 #695; 4. Brizel, 1999 #1121; 5. Brizel, 1996 #1124; 6. Brizel, 1997 #1123; 7. Hockel, 1996 #1111} and can be exploited for cancer therapy. 18. Shibata, 2002 #1657.1 Hypoxia selects for a mutagenic, carcinogenetic, and aggressive malignant phenotype. 19. Graeber, 1996 #942.1 Oxygen status is so important in tissue homeostasis that the absence of oxygen, hypoxia, is the causative element in an entire regulatory peptide signaling cascade. Hypoxia inducible factor 1α, HIF1α, is the master regulator of the response of the cell response to hypoxia, initiating the signal cascade. {10. Semenza, 1998 #1693.} The cascade generates compensatory responses to hypoxia at the cellular level, an intracrine response e.g., apoptosis, {11. Carmeliet, 1998 #1132}, local vascular response through increased production of Vascular Endothelial Growth Factor (VEGF), a paracrine response {124. Carmeliet, 2000 #1131; 10. Semenza, 1998 #1693}, and a general organism response, e.g., erythrocyte production through the increase in production of erythropoietin, an endocrine response {10. Semenza, 1998 #1693.}

The anti-cancer success of anti-VEGF therapy {128. Sandler, 2007 #2192} as well as in vitro work, e.g., {126. Li, 2007 #2214; 125. Forsythe, 1996 #2109} argues that in vivo, in situ, the signal peptide response to hypoxic environment is different in normal and malignant cells and tissues. The present invention, for the first time, uses electron paramagnetic resonance (EPR) imaging (EPRI) to demonstrate this non-invasively in animals with possible extension to humans. Most tests of cell signaling in vivo model subjected the whole animal to an environmental change and then imaged the local response ex vivo. {127. Picchio, 2008 #2103.} There is virtually no literature dealing with the heterogeneity in normal tissue and solid tumors. Although in vitro work has established HIF1α signaling, this has profound implications for therapeutic strategy. For example, it may explain failure of oxygen manipulation to enhance tumor therapy with radiation. {129. Suit, 1984 #1584}

A major goal of the Center for EPR Imaging In Vivo Physiology at the University of Chicago is obtaining uniquely high-resolution quantitative images of tissue and tumor $pO_2$. The present invention provides an entirely new means of molecular imaging of the peptide signal response to hypoxia, using EPR, registered with $pO_2$ images. This technique can be extended to a vast array of peptide-signaling processes. An example of this is the imaging of VEGF, a HIF1α cascade signal response to create new vessels. Combined, co-localized images of $pO_2$ and peptide-signaling response will produce a quantified, localized relationship between the extent of hypoxia and the cell/tissue signal response to hypoxia in vivo, in situ, which we hypothesize is different in malignant and normal tissue. We anticipate the eventual extension of EPR imaging technology to humans. $pO_2$ stimulus images registered with peptide signal response will show individual variations in local stimulus-response to guide individual therapy. The cell signaling technology described here will impact the study of human health and disease.

FIG. 8 is an EPR oxygen image of two planes of a mouse leg bearing an FSa fibrosarcoma. Colorbars show $pO_2$ in mm/hg (torr). Numbers on planes are mm. Resolution: 1 mm spatial, 3 torr $pO_2$. Tumor is not distinguished in this image but separately defined using a registered $T_2$ MRI indicating large central oxygen gradients in the tumor.

Molecular imaging shows heterogeneity of tumor/tissue condition and signal response: Although cell signaling discoveries have provided unique insight into modes by which cells communicate with cells in their environment, {14. Alberts, 2008 #2096} these studies of isolated cells in artificial homogeneous environments contrast with the enormous heterogeneity of a living animal as shown in FIG. 4 and {15. Fischbach, 2009 #2089}. The interaction of anatomy and signaling molecules through vascular bed structure, target organ distance, size and location can affect signaling. Organ- or tissue-dependent modulation of the signaling can provide another layer of control that needs to be understood to fully comprehend the physiology of signaling. A crucial reason to image cell signaling is this variation with position of cellular environments, shown in FIG. 1. Registering images of a quantified environment characteristic like $pO_2$ with images of the peptide response allows the development of models stimulus and response in a native environment.

Reporter protein (RP)/molecular beacon (MB) imaging technologies: The reporter gene LacZ has been a major tool used to dissect transcription induction using optical and fluorescence molecular beacon (MB) detection. {16. Alam, 1990 #1662.} The original such technology, LacZ, the bacterial gene encoding β-galactosidase (reporter) turns the indole linked sugar X-Gal blue, an optical MB. {Holt, 1958 #1663.} By coupling the β-galactosidase gene to a gene of interest, gene expression is directly seen taking place in blue cells. Many other such technologies have followed. {16. Alam, 1990 #1662; 18. Chalfie, 1994 #1664; 19. Weissleder, 2003 #1694; 20. McCaffrey, 2003 #1692; 21. Blasberg, 2003 #1681; 22. Massoud, 2003 #1687; 23. Herschman, 2003 #1684}, producing chromophore or fluorescent MBs in cells producing transcriptionally coupled gene products that can be detected and imaged in vivo. The work proposed in this grant uses this basic technique, modified to turn on an EPR MB in response to hypoxia simultaneously imaged in vivo, obviating the problems with radionuclide, optical or MRI techniques.

Molecular Imaging Techniques Other than EPR Do Not Easily Allow Imaging of Animal Environment Condition and Cell Signal Response: Optical images and radionuclide imaging dominate molecular imaging. {24. Dothager, 2009 #2227.} Optical techniques (e.g., www.xenogen.com/prodimagl.html) use reporter genes that can be engineered into transgenic mice {25. Zhang, 2001 #1695} or into implanted tumor cells in mice {26. Adams, 2002 #1680} are surface weighted because of the rapid non-resonant absorption of optical frequency light by tissue. This makes it difficult to quantify image signal intensity, linewidths or relaxation times of depth greater than a few mm. {27. Kirkpatrick, 2004 #1691.} Other than in artificial systems such as window chamber {28. Dewhirst, 1996 #1775}, quantified relationship between stimulus such as micro-environmental oxygen and peptide signal response is difficult.

Detection of radiotracer with positron emission tomography (PET) avoids problems with depth sensitivity {29. Schober, 2009 #2099; 30. Sun, 2001 #1374; 31. Blasberg, 2003 #1665} and is extremely flexible. The advantage of radiotracer reporters is that it can be immediately translated to human studies. However, the major problems with PET imaging is its limited resolution in space (~2 mm) and in time and distinguishing signal from the environmental stimulus reporter from the peptide signal response reporter. For radionuclide studies, hypoxia is defined as the reductive retention of nitro-imidazole {33. Raleigh, 1992 #765; 34. Evans, 1996 #931} or ATSM copper chelates. {35. Lewis, 1999 #1371.} Hypoxic signaling via HIF1α might be imaged as is proposed in this grant with vectors containing hypoxia responsive elements (HREs) that bind HIF1α promoting production of, e.g., a thymidine kinase RP that would cause hypoxic cells to retain radioactive thymidine (the molecular beacon (MB)). This has severe limitations:

Firstly, it is difficult to distinguish the signal from the compound signaling hypoxia from the thymidine retained through phosphorylation, signaling hypoxic response. EPR allows spectrally distinct hypoxia images and the peptide signal response images.

Secondly, the EPROI is quantitative while the reductive retention image is qualitative. Radionuclide images depend heavily on access of the radionuclide to the location where oxygen is measured, and other aspects of local tissue reductive capability, i.e., P450 reductase, xanthine oxidase, etc. activity. {36. Melo, 2000 #2229.} For EPROI, as long as some spin probe reaches the location, the oxygen measurement depends only weakly on the signal amplitude. Rather it depends on the signal relaxation time or line width.

Molecular imaging with MRI creates contrast with the RP requiring an extremely large molecular signal {37. Louie, 2000 #1395; 38. Weissleder, 2000 #1673} because the technology introduces contrast in a very high signal background. Unlike MRI, the EPR technology activates a "beacon in the dark". In addition, MRI images provide poor $pO_2$ sensitivity.

EPR oxygen images use very low magnetic fields and are specific and sensitive to $pO_2$: EPR images are obtained at excitation RF frequencies of very-high-field (6-7 T) whole-body MRIs {39. Vaughan, 2009 #2230} but because the magnetic moment of the electron is 658 times that of the water proton, magnetic fields are 1/658 that of MRI. EPRI uses a low field with inexpensive magnet systems of about 90 Gauss=9 milliTesla (mT) at 250 MHz frequency. {40. Halpern, 1989 #89; 41. Halpern, 1991 #899.} This is a low-cost technology not requiring superconducting magnets, although standard-field MRI is, in some embodiments, used to identify tumor. EPR spectral linewidths of certain carbon-centered spin probes, trityls, are specific and sensitive to local $pO_2$. {42. Halpern, 2003 #1798.} The narrow (μT) spectral linewidths, or, equivalently, the inverse transverse relaxation times (1/(5 μs)) of these spin probes are directly proportional to the local oxygen concentration. They give a direct quantitative readout of tissue micro-environmental $pO_2$. Using spectroscopic EPR imaging {43. Lauterbur, 1984 #177; 44. Maltempo, 1986 #181; 45. Halpern, 1994 #93; 46. Epel, 2008 #2200}, spatial images of quantitative tissue $pO_2$ may be obtained from tumor and normal tissues of living animals.

Registered images of cell signaling will show local tissue response to $pO_2$ stimulus. In some embodiments, the present invention obtains simultaneous registered images of cell signals responding to low $pO_2$ using nitrogen-centered molecular beacons activated by hypoxia-signaling-coupled reporter proteins. These cell-signal images would be spectrally distinct from the trityl-based $pO_2$ images and are, in some embodiments, obtained simultaneously with them. At 9 mT, carbon centered and the central manifold of $^{14}N$ have sufficiently different absorption frequencies (~8.4 MHz) that they are, effectively, two-color images. The readout frequencies are low enough to avoid poisonous non-resonant absorption to allow oxygen quantification deep in living tissue. {45. Halpern, 1994 #93.} A different embodiment with simultaneous imaging of $pO_2$, HIF1α signaling and the vascular endothelial growth factor (VEGF) response to HIF1α would use carbon-centered oxygen-sensitive trityl radicals and $^{14}N$ and $^{15}N$ molecular beacons, effectively providing three-color images automatically registered with each other.

The present invention, for the first time, provides automatic co-localization of micro-environment stimulus and cell signal response in native animal tissue and tumor environment, allowing their comparison. Distinct responses of normal and tumor tissue will provide insight into therapies that can exploit these differences, targeting malignant tumors and sparing normal tissues. We believe this to be paradigm-shifting work, sharpening the in vivo understanding of signaling process. The present invention will allow monitoring subject-to-subject and tumor-to-tumor variation, allowing a more individualized therapy. This will open a major avenue to the improvement of the therapeutic ratio for cancer therapy.

Section #3: $T_{1e}$ Imaging Using Filtered Backprojection and Single Point Imaging Methodologies Spin-lattice relaxation ($T_{1e}$) of a spin probe can be sensitive to various environmental parameters including local oxygen $pO_2$. We have developed three dimensional pulse imaging of $T_{1e}$ in vivo using fast repetition time saturation, inversion recovery and, stimulated echo sequences. $T_{1e}$ images generated by sequences that have electron spin echo readout are reconstructed with filtered backprojection protocols while those using free induction decay readout are reconstructed with the single point imaging protocols. We compared $T_{1e}$ and $T_{2e}$ imaging of narrow line trityl spin probe in vitro to find their performances very similar. However, for in vivo oxymetry $T_{1e}$ imaging is found to be more promising due to weaker dependence of $T_{1e}$ on environmental factors other than oxygen.

Introduction: Transverse relaxation or $T_{2e}$ based EPR continuous wave and pulsed imaging techniques have proved to be very promising methodologies for oxygen imaging using injected paramagnetic molecule as the probe of the spatial distribution of oxygen in animals {101. Halpern 1989 #89}; {102. Kuppusamy 1994}; {103. Elas 2003}; {104. Mailer 2006}; {105. Epel 2010}; {106. Subramanian 2002}. In many cases the same relaxation mechanisms that affect $T_{2e}$ of a spin probe, act on spin-lattice relaxation, $T_{1e}$, making $T_{1e}$ sensitive to the environment {107. Slichter, 1996}. For example, spin exchange interaction with molecular oxygen results in linear $R_{2e}=1/T_{2e}$ and $R_{1e}=1/T_{1e}$ dependence on pO$_2$ with nearly identical proportionality coefficients {108. Ardenkjaer-Larsen, 1998}. On the other hand, not all relaxation mechanisms affect $T_{2e}$ and $T_{1e}$ in the same way. For example, the inter-molecule electron spin dipole interactions will not affect spin-lattice relaxation while enhancing the phase relaxation. This makes $T_{1e}$ imaging a very attractive imaging modality, separate from $T_{2e}$ imaging. However, no systematic attempts to image in vivo $T_{1e}$ using pulsed methods in vivo have been undertaken.

Given the widely used $T_{2e}$ pulsed EPR oxygen imaging techniques, it is natural to use similar techniques to read out $T_{1e}$ based image information. Although very different in imaging principles and observed relaxation kinetics both electron spin echo (ESE) imaging oxymetry and single point imaging (SPI) oxymetry can precisely measure $T_{2e}$. ESE imaging uses filtered backprojection (FBP) for image reconstruction from a number of static gradient projections recorded with fixed gradient amplitude, $|\vec{G}|$, and different gradient orientations. The projections are obtained by the Fourier transformation of time domain signals. In order to preserve correct phase information dead-time free time domain signals are required which can be achieved by generation of echoes {104. Mailer, 2006}. In our earlier work we used two pulse $\pi/2$-$\tau$-$\pi$-$\tau$-echo ESE (2pESE for brevity) {104. Mailer, 2006}; {109. Epel, 2008 #2200}. To measure $T_{2e}$ multiple separate images with different $\tau$ delay values were acquired and the exponential decay times of signal in each individual voxel in those images measured.

SPI methodology is based on different principles {106. Subramanian, 2002}; {110. Matsumoto, 2006}. The dead time free acquisition is achieved by recording the single point on free induction decay, FID, at a known time, $t_{SPI}$, as a function of stepped static gradient amplitudes sampled on a cubic grid. This signal forms a 3D "pseudo-echo", the FT of which generates a spatial image. The spatial information is encoded into the phase of FID. In the simplest form of SPI, the phase relaxation times are extracted from multiple images obtained at different $t_{SPI}$. The fit of individual voxels to exponential decay gives the FID dephasing time $T_{2e}^*$ directly related to $T_{2e}$ as $1/T_{2e}^*=1/T_{2e}^{hf}+1/T_{2e}$, where $T_{2e}^{hf}$ is the oxygen independent phase relaxation due to hyperfine interaction with trityl nuclei. More advance imaging schemes were developed to improve the precision and reduce artifacts of SPI technique {110. Matsumoto, 2006}; {111. Devasahayam, 2007}.

For selection of a pulse method for $T_{1e}$ imaging number of pulse sequence parameters should be taken into account. One of them is the pulse sequence bandwidth. Since the whole projection is acquired at once, the bandwidth of the pulse sequence has to be broad enough to cover the equivalent bandwidth of the EPR line broadened by any applied gradient. A bandwidth of about 5-10 MHz is typically sufficient for low frequency in vivo imaging of 3 cm specimens such as portions of mouse anatomy {109. Epel, 2008 #2200}. Another requirement is a dead time free acquisition, which can be achieved by utilizing the same principles implemented in the ESE FBP $T_{2e}$ imaging protocols.

We have selected three conventional ways to determine $T_{1e}$, two of which can be combined with two readout imaging methodologies:
Saturation by fast repetition (SFR ESE and SFR SPI);
Inversion recovery (IRESE and IRSPI);
Stimulated echo (SE, ESE only).

In the SFR experiment (FIGS. 1A and 1B) the amplitude of the ESE or FID is measured as a function of repetition time, $T_R$, of the respective sequence. A short repetition time (less than $T_{1e}$) saturates the spins so the echo amplitude reduces as $\exp(-T_R/T_{1e})$. Varying the repetition rate monitors the spin system saturation to get $T_{1e}$. The second type of $T_{1e}$ sequence, inversion recover, inverts the spin polarization using a broadband $\pi$ pulse and the recovery is measured using as a function of the delay T after the inversion pulse. The echo detected inversion recovery sequence with ESE detection, IRESE (FIG. 1A1) has been used for $T_{1e}$ sensitive imaging {112. Eaton, 1987}. The delay $\tau$ was kept fixed during experiment. The bandwidth of this sequence is approximately equal to the bandwidth of the 2 pulse ESE detection sequence. The inversion recovery sequence for SPI, referred to as IRSPI, utilizes FID detection (FIG. 1D) and the bandwidth of this sequence is approximately equal to the bandwidth of the inversion pulse. An alternative approach involves saturation recovery experiment. Here, the inversion pulse is replaced by long, $t_p \gg T_{1e}$, saturation pulse. The bandwidth of this pulse is insufficient for the purposes of imaging. Because additional facilities such as modulation of the magnetic field or pulse frequency during this pulse may be required to increase its bandwidth, we excluded this sequence from our evaluation. The third sequence, SE (FIG. 1E), is the three-pulse 'stimulated' echo sequence {113. Schweiger, 2001}. In this sequence the $\pi$ pulse of the 2 pulse ESE experiment is split into two $\pi/2$ pulses separated by a waiting time T. After the first two $\pi/2$ pulses the magnetization is stored along the z-axis (longitudinal axis) where it remains during the time T. This waiting time is varied allowing the magnetization to decay with $T_{1e}$. The third $\pi/2$ pulse rotates the z-component back into the transverse xy-plane where it gives rise to a stimulated echo at fixed time $\tau$ after the third pulse. This sequence is known to have nearly double bandwidth as compared to 2 pulse ESE (and thus IRESE) sequence with the same length of the RF pulses {114. Kevan, 1990} and, therefore, is very promising for reducing applied power in living subject.

We present a study of these different methods for imaging of $T_{1e}$ using our 250 MHz pulse spectrometer. We also compare the precision of $T_{1e}$ imaging with that of $T_{2e}$ imaging for determination of the O$_2$ concentration in the phantoms.

Materials and Methods:
Spin Probe: The spin probe used for the EPR imaging was a OX063 radical methyl-tris[8-carboxy-2,2,6,6-tetrakis[2- hydroxyethyl]benzo[1,2-d:4,5-d']bis[1,3]dithiol-4-yl]-trisodium salt, molecular weight=1,427 from GE Healthcare (Little Chalfont, Buckinghamshire, UK). The 1 mM solution of spin probe in saline was contained in a flat-bottomed borosilicate glass cylinder of 9.5 mm inner diameter and 45 mm length. The 0% $O_2$ sample was deoxygenated using a multiple-cycles freeze-pump-thaw technique and flame sealed. The 9.3% $O_2$ sample was produced by bubbling of the solution with corresponding nitrogen-oxygen gas mixture and then was sealed with epoxy. Samples were placed into the resonator horizontally along the resonator's axis of symmetry and centered in the axial plane of the resonator. Because samples were half-full this produced a meniscus at the liquid-air contact surface.

Pulse Imager and Pulse Sequences: In this work we used the versatile pulse 250 MHz imager described in details elsewhere {109. Epel, 2008 #2200}. To utilize the full power of our 2 kW RF amplifier {115. Quine, 2006} (Tomco Technologies, Norwood SA, Australia) the transmit-receive switch of the imager was redesigned using high power components and utilizing a new protection scheme {116. Sundramoorthy, 2009.} A pulse amplitude modulation switch was added to produce π/2- and π-pulses of equal duration (hence equal bandwidth) {117. Quine, 2010}. The imager control software SpecMan4EPR version 1.1.6 {118. Epel, 2005} was used.

To facilitate the image comparison, the measurement time was kept 10 minutes for all images. Since pulse sequences are intended to image samples with heterogeneous relaxation times, we used the same sequences for phantoms and animal imaging. Standard deviation of relaxation times in a homogeneous phantom was used as an estimation of relaxation time errors. Two outer layers of images were excluded from standard deviation calculations to avoid partial volume averaging artifacts. Tables 1 and 2 present parameters of $T_{1e}$ and $T_{2e}$ sequences. The repetition time for ESE sequences, $T_R$, was adjusted to keep the delay between the last pulse in a sequence to the first pulse, $T^{LF}_R$, of the next sequence constant. This method of repetition time definition is found to be more efficient as compared to conventional method where repetition time in the experiment is kept constant, independently of sequence length. The optimal repetition time was determined by decreasing $T_R$ from $5T_{1e}$ until sequence still provided correct values for $T_{1e}$ or $T_{2e}$. To accelerate acquisition of the IRESE/IRSPI images, the image corresponding to the last delay T was substituted with an image obtained without inversion pulse and delay T. This halved the acquisition time of the last delay image.

For all ESE sequences the same 3D FBP protocol {104. Mailer, 2006}; {119. Eaton 1991} was applied: 208 projections corresponding to the 18×18 (eighteen-by-eighteen) equal solid angle gradient spacing {120. Ahn 2007(1)} were acquired; gradient strength was $|\vec{G}|=15$ mT/m; object field of view was 4.24 cm.

A baseline (acquisition at a far off-resonant field) acquired every fourth trace (53 traces in all). To reduce FBP reconstruction artifacts the acquired set of projections was four-fold linearly interpolated {121. Ahn 2007(2)} and filtered with a 3D Ram-Lak filter with a cutoff at 0.5 times the Nyquist frequency. In the images we kept only those voxels with a signal amplitude greater than 15% of the maximum amplitude at the shortest delay. Further data acquisition and processing methods are discussed in detail elsewhere {109. Epel, 2008 #2200}.

The SPI protocol involved acquisition of 5547 FIDs at delay $t_{SPI}=1000$ ns with gradients corresponding to $23^3$ matrix in which only the gradients inside the sphere with the diameter of 23 gradients were taken. The maximum gradient of 15 mT/m was used. A baseline was acquired every 20th trace to suppress imager related artifacts. The 3D 'pseudo-echo' matrix was apodized with hamming window and Fourier transformed to produce final image. All data processing was performed using in-house MATLAB (The Mathworks, Inc., and Natick, MA, USA) software.

Non-imaging versus imaging conditions: Acquisition of spatial information requires a considerable time. Therefore, imaging protocols have to balance between precision of spatial and relaxation-time measurements. For example, the relaxation times are estimated from five to eight points on the decay curve. Moreover, the time of in vivo imaging can be limited by the animal physiology. These restrictions do not apply for non imaging measurements on phantoms, which can have large number of delays and can take much longer time. The parameters of sequences for these measurements are selected so that they have no influence on measured relaxation times.

Animal Imaging: $T_{1e}$ and $T_{2e}$ images were sequentially taken on the same animal with no delay in between. All animal experiments were done according to the USPHS "Policy on Humane Care and Use of Laboratory Animals", and the protocols were approved by the University of Chicago Institutional Animal Care and Use Committee. The University of Chicago Animal Resources Center is an Association for Assessment and Accreditation of Laboratory Animal Care-approved animal care facility.

Results: To demonstrate applicability of $T_{1e}$ imaging for oxymetry we present the imaging results on two phantoms with different concentration of $O_2$: 0% (Table 3, FIG. 2) and 9.3% (Table 4), respectively. This range of oxygen concentrations is important hypoxia studies on animals {103. Elas 2003}; {122. Elas 2008}; {123. Matsumoto 2008}. The relaxation times determined under non-imaging conditions (no applied gradients, $T_R=15T_{1e}$) are given in the footnotes of the tables. The results of $T_{2e}$ measurements using 2pESE are given in the tables for comparison. The standard deviation of relaxation times in homogeneous phantom was used for estimation of errors. Between all $T_{1e}$ imaging methods IRESE sequence demonstrated the smallest standard deviation. SE showed slightly worse performance, while SFR had very large standard deviations on 0% $O_2$ phantom and was unable to produce $T_{1e}$ image of 9.3% $O_2$ phantom. 2pESE performance superseded the performance of all $T_{1e}$ methods, however on 0% $O_2$ phantom the performance of IRESE came very close to the performance of 2pESE. Similarly to ESE, IRSPI sequence demonstrated much better performance than SFR SPI. Here we should note that the comparison of absolute precisions of ESE and SPI methodologies is outside of the scope of this work due to the lack of expertise in SPI.

For demonstration of the $T_{1e}$ imaging on a live animal we selected the IRESE (FIG. 3A) methodology, which showed the best performance on phantoms, and compared the $T_{1e}$ image with $T_{2e}$ image (FIG. 3B) obtained using 2pESE on the same animal. The outlines and general patterns of the images are very similar. The average relaxation times in $T_{2e}$ image are shorter, consistent with the typical ratios of $T_{1e}$ and $T_{2e}$ in trityls. Nevertheless the breadth of relaxation time histograms is approximately the same.

Discussion: The data presented in the Results subsection demonstrate the feasibility of $T_{1e}$ imaging of live animals. IRESE images show comparable with $T_{2e}$ images quality both in vitro and in vivo. The major factor that affects precision of $T_{1e}/T_{2e}$ imaging is an image signal to noise ratio (SNR). Assuming that for all methodologies the imager noise characteristics are equal, the image SNR will be governed by an amplitude of a signal and number of acquisitions. Inversion recovery has the highest change in a signal amplitude due to relaxation, double of that for other sequences, since the evolution of signal from negative to positive is monitored. On the other hand the duration of inversion recovery sequences is longer than $T_{2e}$ sequences, which reduces the number of sequence repetitions per unit time and hence SNR. The amplitude of signal for SFR is proportional to $\exp(-T_R^{MIN}/T_{1e})$, where $T_R^{MIN}$ is the minimum $T_R$ in an experiment. In our instrument minimum $T_R$ is governed by the duty cycle of the power amplifier, insufficient to generate SFR sequences with short enough $T_R$. This makes SFR imaging not feasible for our instrument. The performance of SE method is worse than IRESE due to twice lower echo signal {114. Kevan, 1990}. However certain advantages can be derived from considerably smaller power requirements of this sequence. SE image was taken using only 8% of RF power required for other methods excluding SFR SPI (see Table 2). Considering all these factors and nearly equal $T_{1e}$ and $T_{2e}$, inversion recovery methods, IRESE and IRSPI, should have comparable performance to 2pESE and standard SPI images, which was demonstrated in the experiment.

The reduction in RF power requirements for SE sequence may make it attractive for large subject imaging. The power required for RF pulses with identical $B_1$ is growing proportional to the resonator volume. Large resonators may require more power than available sources can deliver. The lower average power deposition may also favor this sequence for human applications.

$T_{1e}$ experiments can not deliver correct concentration map of the sample. Being acquired at non-zero τ, the $T_{1e}$ amplitude image will always carry an effect of $T_{2e}$. To obtain true amplitude, the $T_{2e}$ measurement has to be performed and amplitude extrapolated to time 0. Thus it might be of interest to combine inversion recovery $T_{1e}$ and $T_{2e}$ imaging into one experiment. Another advantage of such a joint experiment would be an economy on delays since there will be no need to measure IRESE or IRSPI with long delay T—the result of such measurement is equal to experiment with no inversion pulse (2pESE or FID SPI).

Conclusions: $T_{1e}$ imaging is feasible and comparable in precision with $T_{2e}$ imaging. Therefore, it can be considered as an alternative method for oxymetry and other applications. Different applications and instruments may benefit from different $T_{1e}$ methods, with inversion recovery imaging exhibiting the best relaxation time precision while SE imaging having the least power requirements.

FIGS. 4A-4F show various pulse sequences for determination of $T_{1e}$: FIG. 4A shows an SFR ESE (saturation by fast repetition ESE) pulse sequence, wherein the repetition rate is varied, FIG. 4B shows an SFR SPI (saturation by fast repetition SPI) pulse sequence, wherein the repetition rate is varied, FIG. 4C shows an SR (saturation recovery) pulse sequence, wherein the delay time T is varied, FIG. 4D1 shows an IRESE (inversion recovery with ESE detection) pulse sequence, wherein the delay time T is varied, FIG. 4E shows an IRSPI (inversion recovery with SPI detection) pulse sequence, wherein the delay time T is varied, and FIG. 4F shows an SE (stimulated echo) pulse sequence, wherein the delay time T is varied.

Figure 5A:
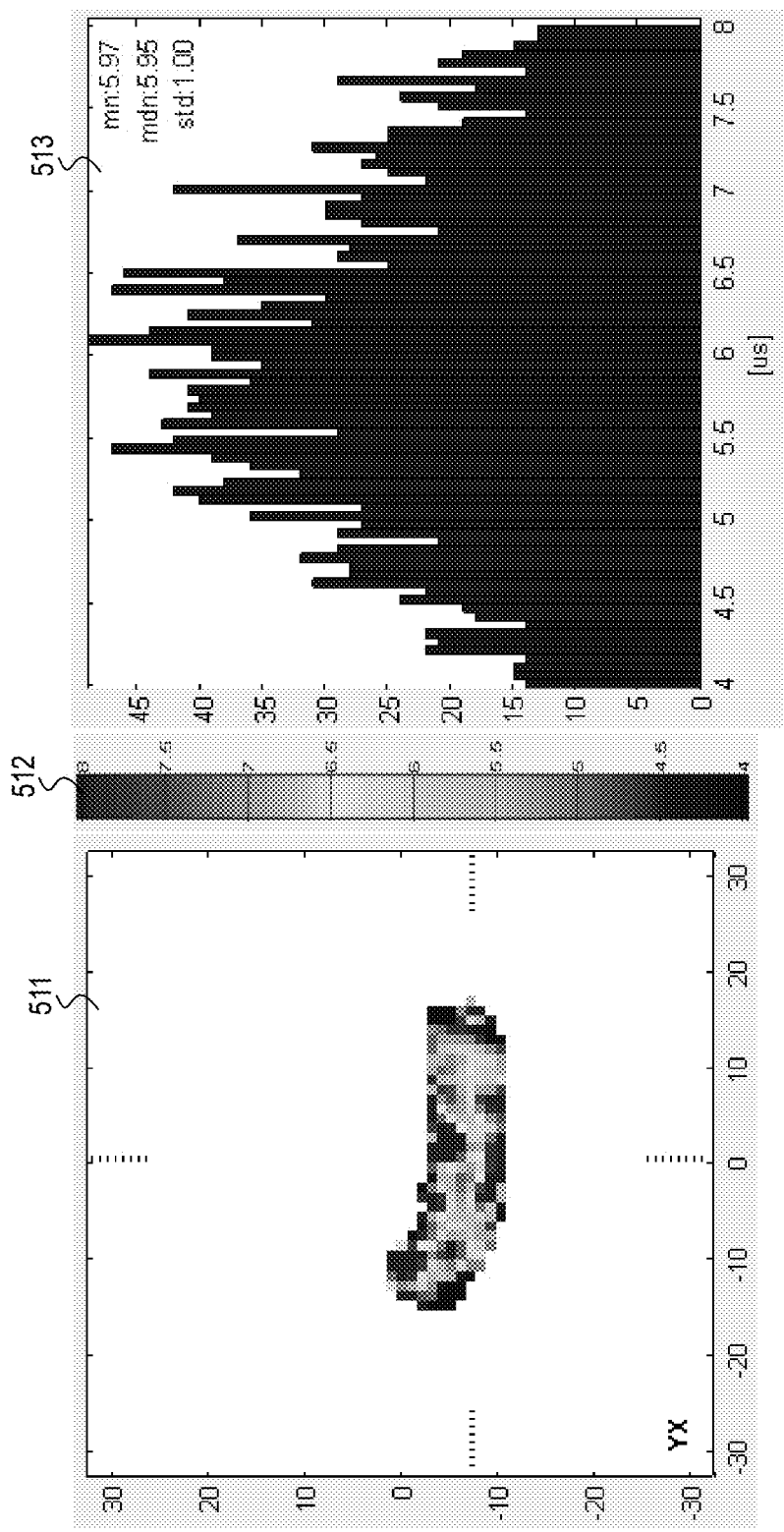
FIG. 5A shows a selected slice $T_{1e}$ image and histogram obtained using SFR ESE.
Figure 5B:
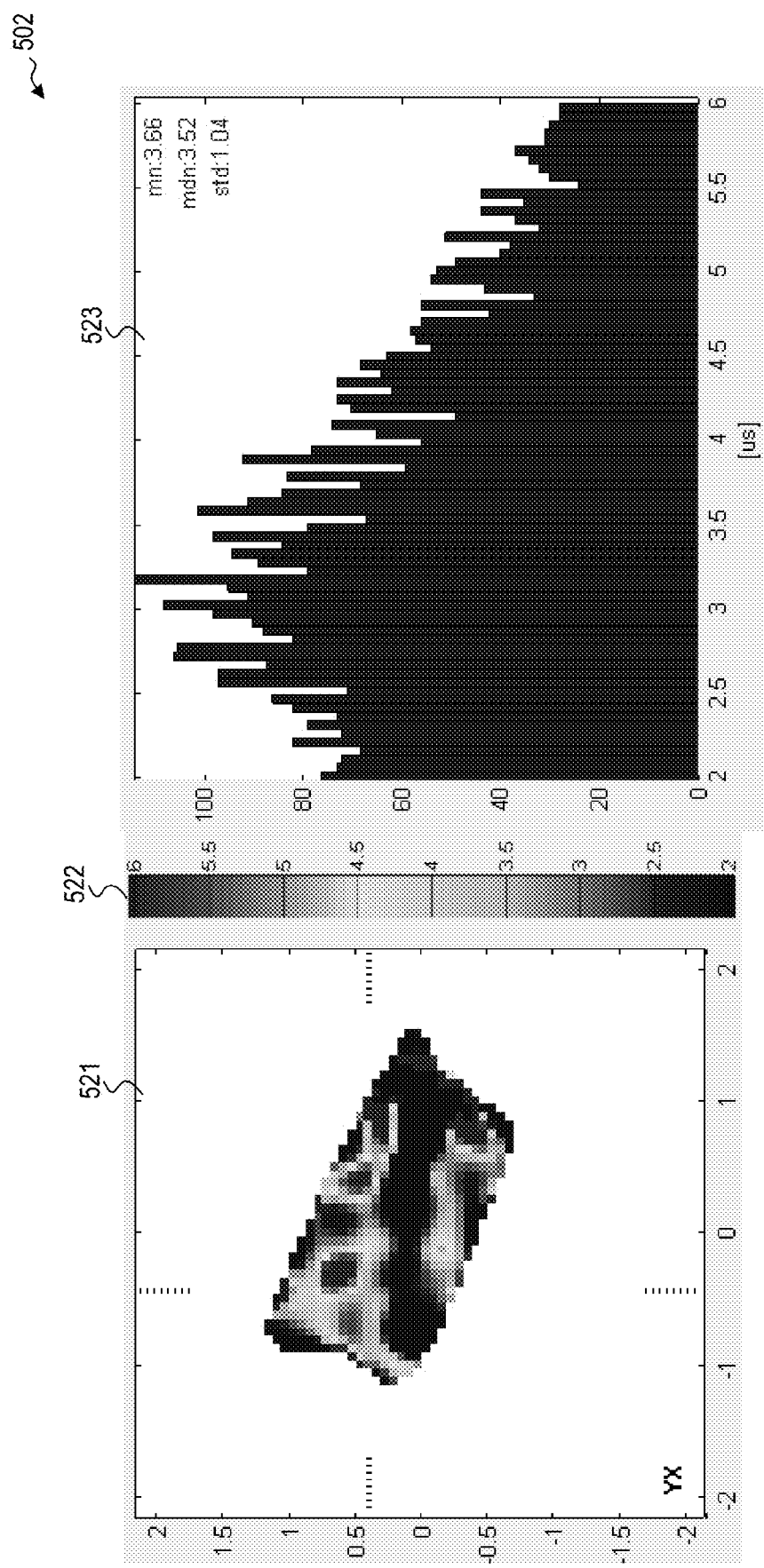
FIG. 5B shows a selected slice $T_{1e}$ image and histogram obtained using SFR SPI.
Figure 5C:
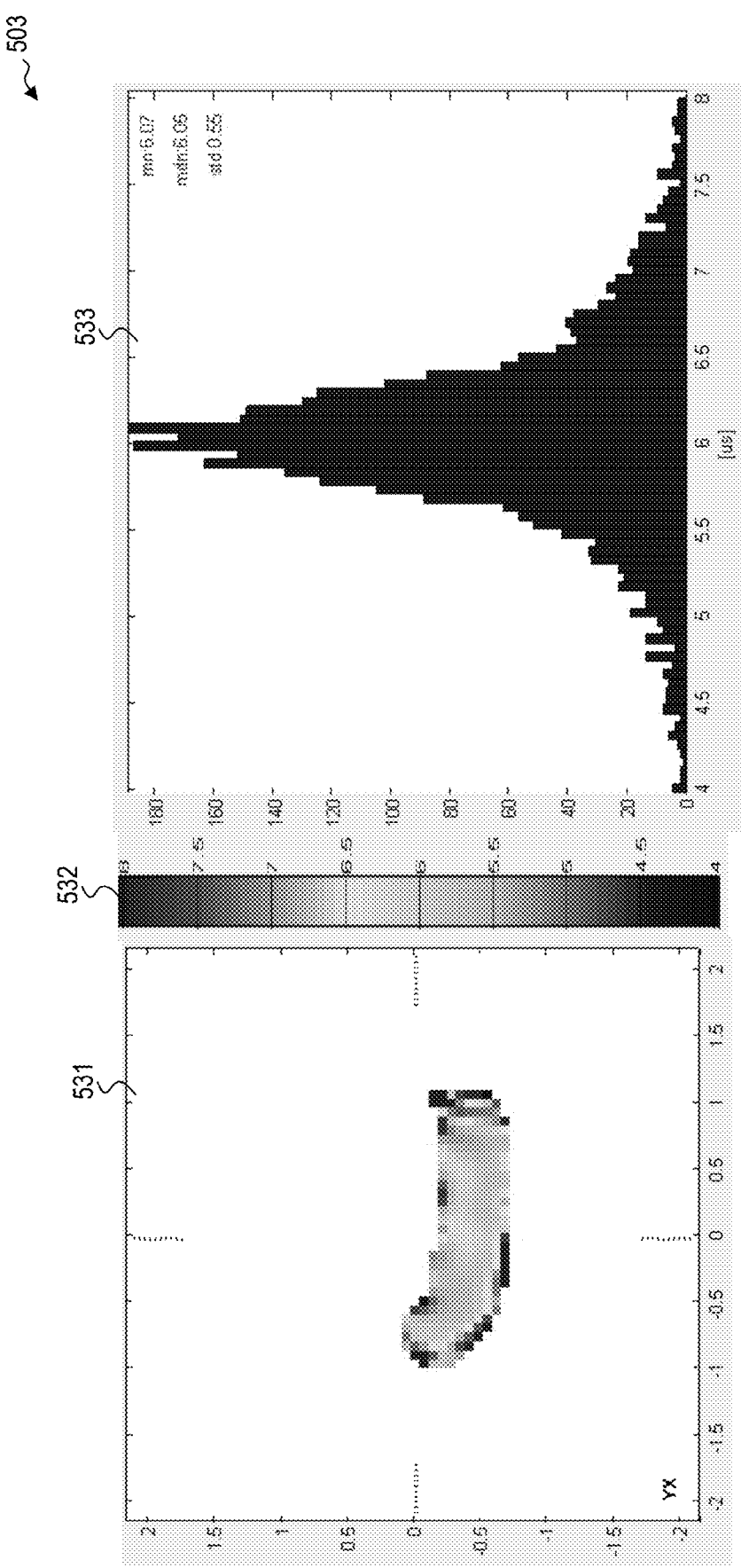
FIG. 5C shows a selected slice $T_{1e}$ image and histogram obtained using IRESE.
Figure 5D:
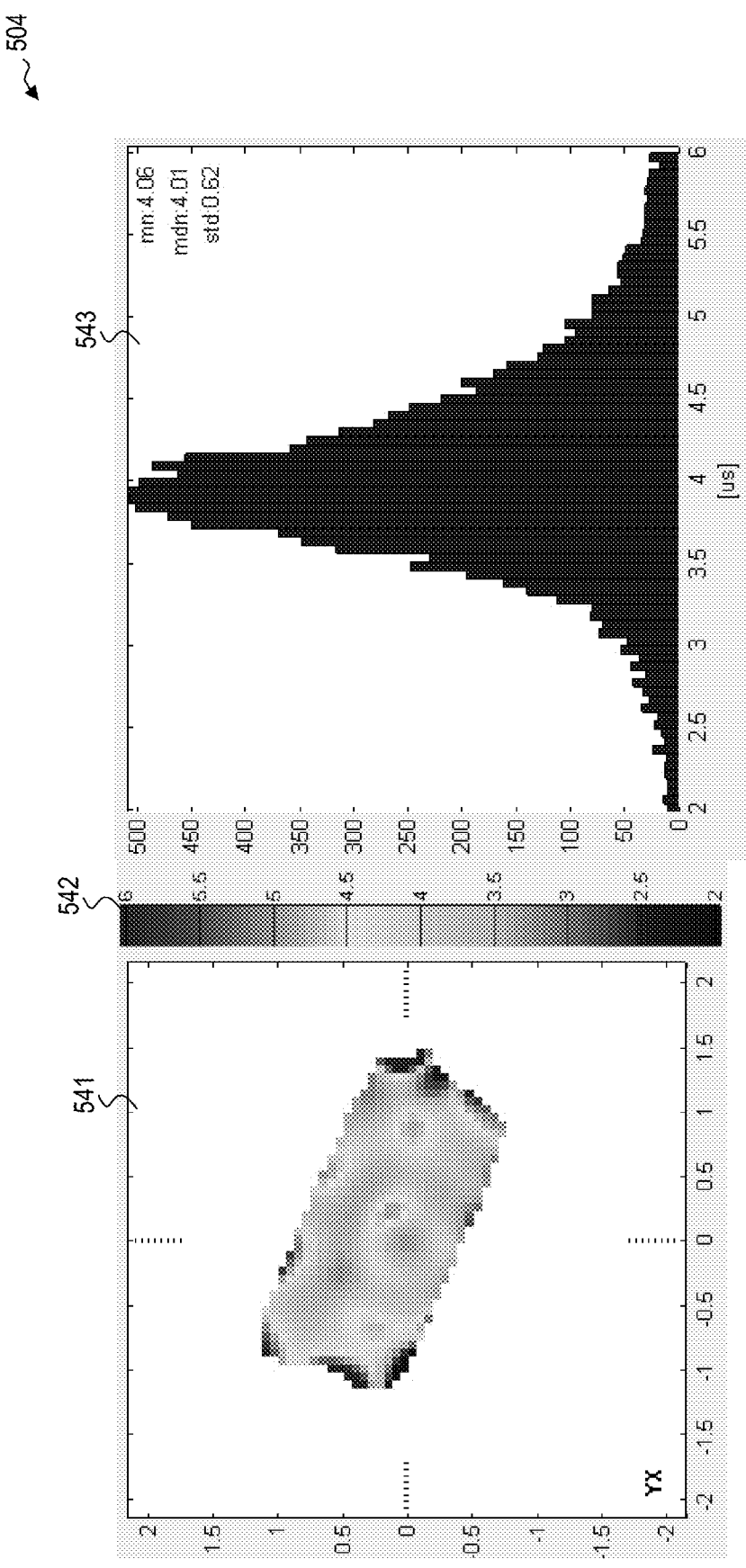
FIG. 5D shows a selected slice $T_{1e}$ image and histogram obtained using IRSPI.
Figure 5E:
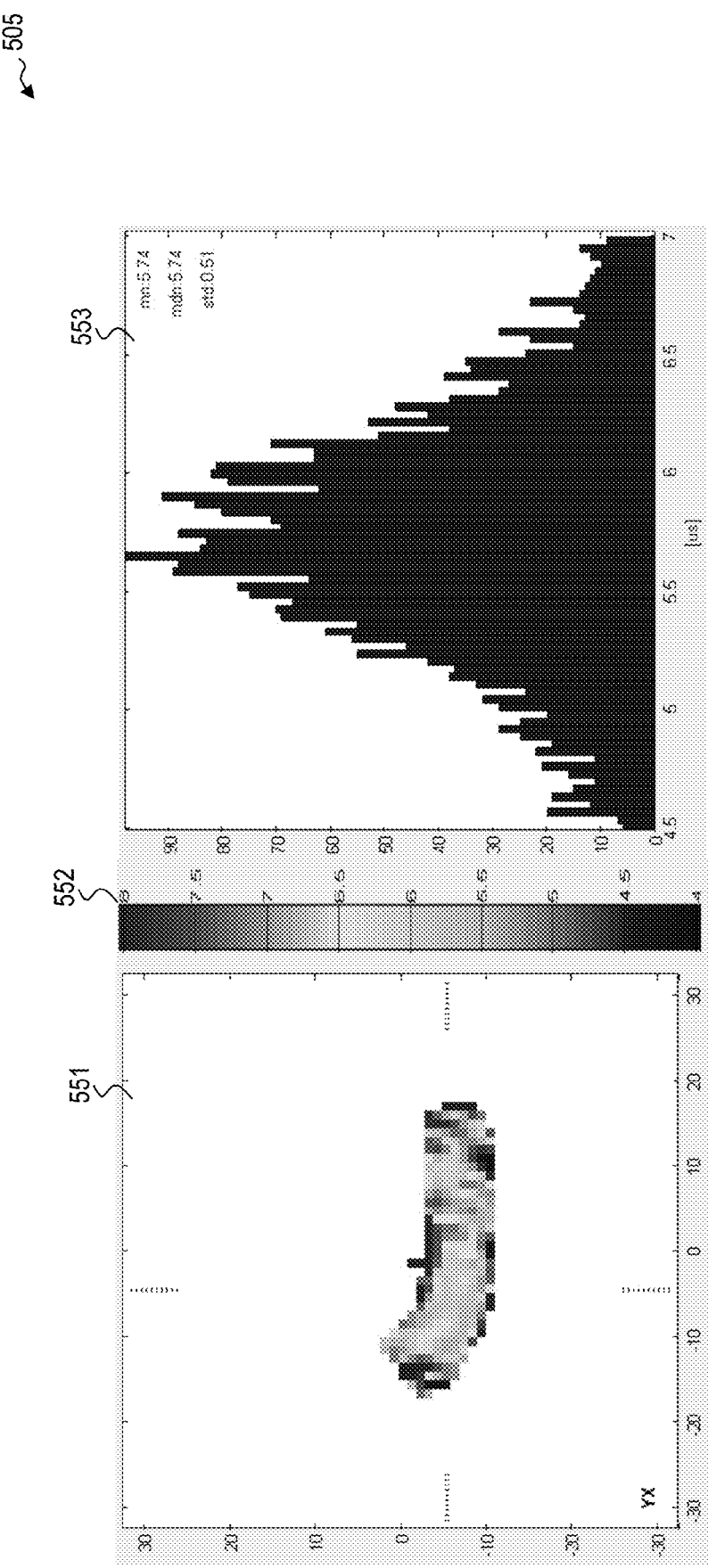
FIG. 5E shows a selected slice $T_{1e}$ image and histogram obtained using SE.
Figure 5F:
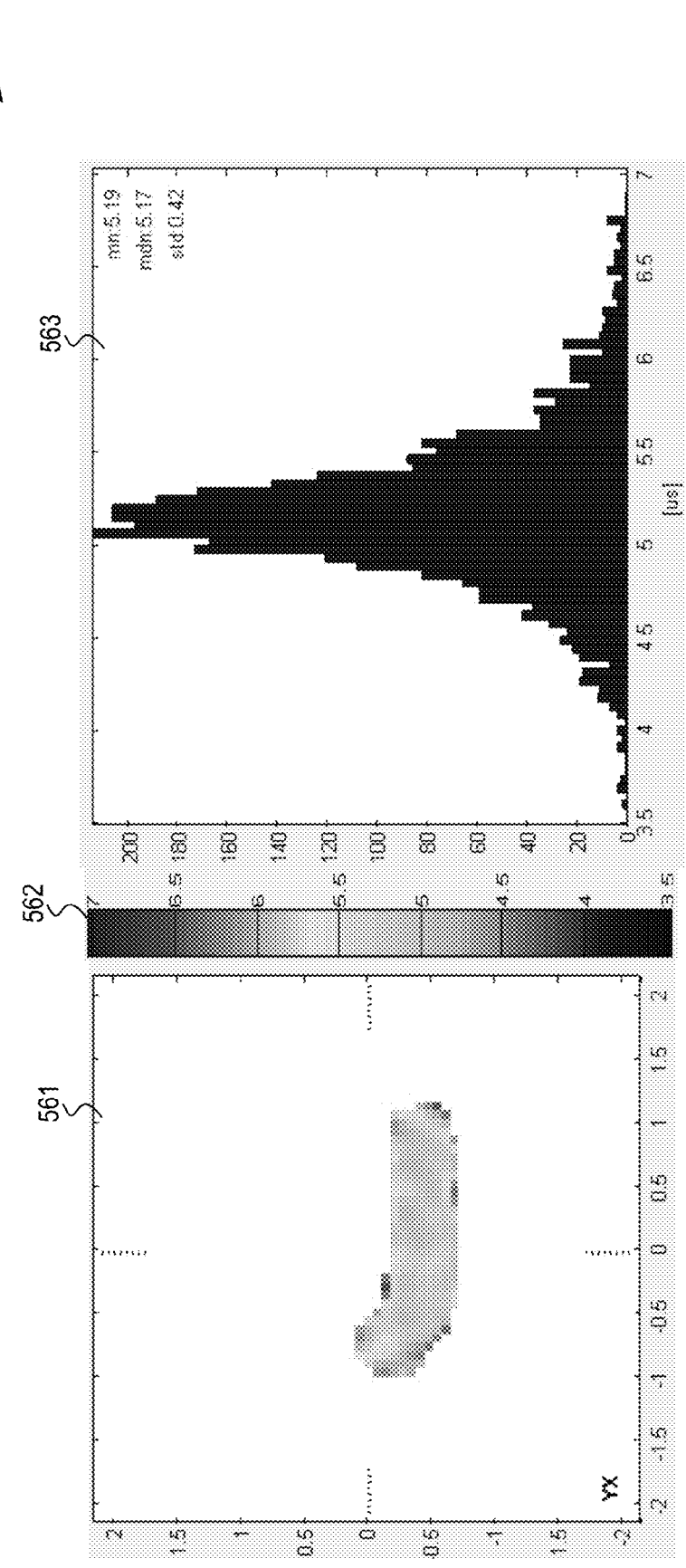
FIG. 5F shows a selected slice $T_{2e}$ image and histogram obtained using 2pESE.

Regarding FIG. 5A, FIG. 5B, FIG. 5C, FIG. 5D, FIG. 5E, FIG. 5F: the selected slices and histograms of T1e images are obtained using for FIG. 5A—SFR ESE; for FIG. 5B—SFR SPI; for FIG. 5C—IRESE; for FIG. 5D—IRSPI; for FIG. 5E—SE; and for FIG. 5F—2pESE. FIG. 5F shows the slice and histogram of $T_{2e}$ 2 pESE image. Experiments A for FIG. 5A, C for FIG. 5C, E for FIGS. 5E, and F for FIG. 5F are performed on 1 mM sample 0% $O_2$, experiments B for FIGS. 5B and D for FIG. 5D are performed on 3 mM 0% $O_2$ sample of triarylmethyl radical OX063.

Figure 6A:
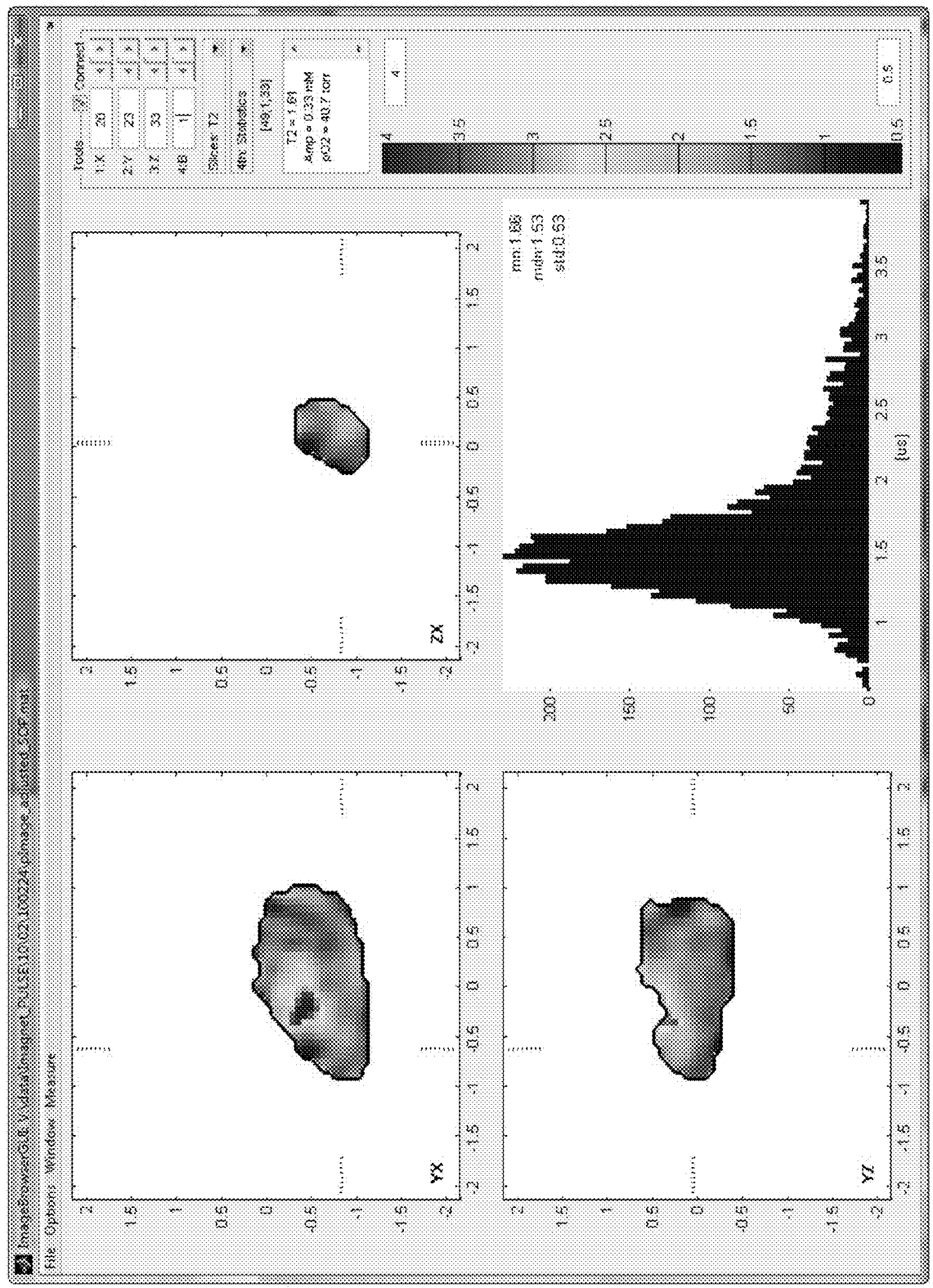
FIG. 6A is a $T_{2e}$ image obtained using a 2pESE sequence.
Figure 6B:
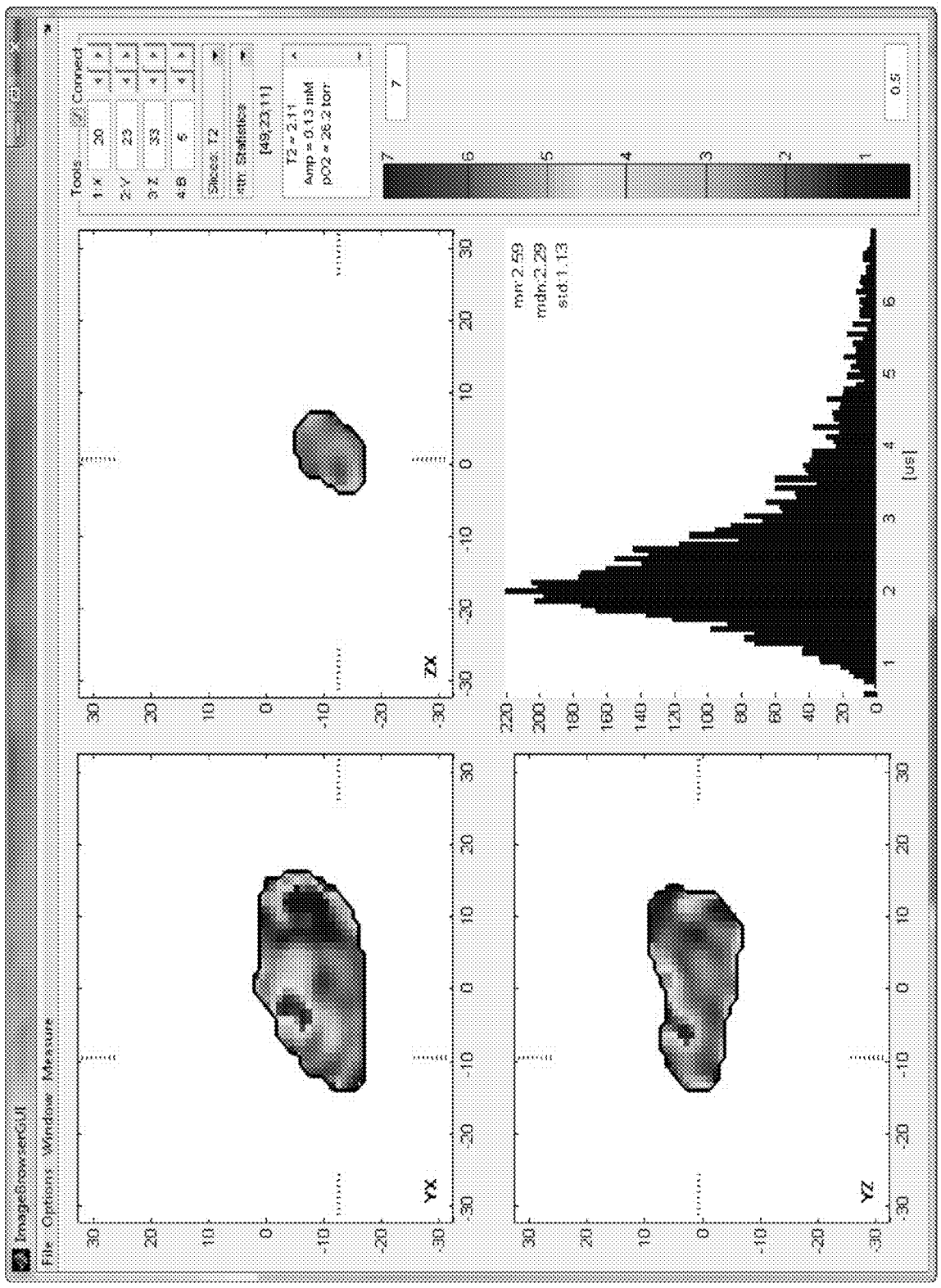
FIG. 6B is a $T_{1e}$ image obtained using an IRESE sequence.
Figure 7:
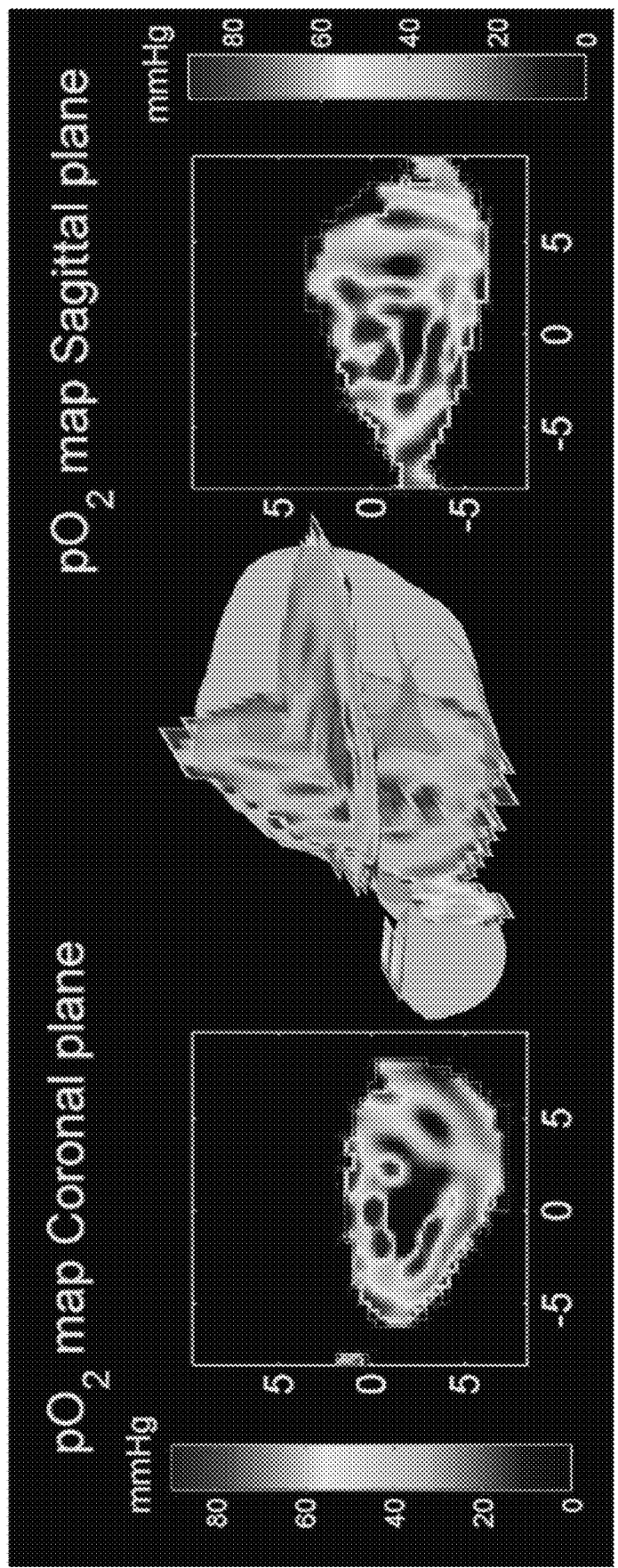
FIG. 7 is an EPR oxygen image of two planes of a mouse leg bearing an FSa fibrosarcoma.

FIG. 6A and FIG. 6B show $T_{2e}$ and $T_{1e}$ images obtained using 2pESE and IRESE pulse sequences, respectively. Tables

TABLE 1

Pulse sequences.

| Protocol | | | | Description | | | |
|---|---|---|---|---|---|---|---|
| | π/2-τ-π-τ-echo; 35 ns π/2 and π RF pulses; τ = 630 ns; 16-step phase cycling, 16640 echoes, including phase cycling; 8 images with different repetition times logarithmically spaced between 10 μs and 25 μs; imaging time 10 minutes. | | | | | | |
| SFR ESE | N | First pulse | First delay | Second pulse | Second delay | Detection channel Re | Detection channel Im |
| | 1 | 0.5X | 630 ns | X | 630 ns | A | B |
| | 2 | 0.5X | 630 ns | −X | 630 ns | A | B |
| | 3 | 0.5X | 630 ns | Y | 630 ns | −A | −B |
| | 4 | 0.5X | 630 ns | −Y | 630 ns | −A | −B |
| | 5 | −0.5X | 630 ns | X | 630 ns | −A | −B |
| | 6 | −0.5X | 630 ns | −X | 630 ns | −A | −B |
| | 7 | −0.5X | 630 ns | Y | 630 ns | A | B |
| | 8 | −0.5X | 630 ns | −Y | 630 ns | A | B |
| | 9 | 0.5Y | 630 ns | X | 630 ns | B | −A |
| | 10 | 0.5Y | 630 ns | −X | 630 ns | B | −A |
| | 11 | 0.5Y | 630 ns | Y | 630 ns | −B | A |
| | 12 | 0.5Y | 630 ns | −Y | 630 ns | −B | A |
| | 13 | −0.5Y | 630 ns | X | 630 ns | −B | A |
| | 14 | −0.5Y | 630 ns | −X | 630 ns | −B | A |
| | 15 | −0.5Y | 630 ns | Y | 630 ns | B | −A |
| | 16 | −0.5Y | 630 ns | −Y | 630 ns | B | −A |

π-T-π/2-τ-π-τ-echo; 35 ns π/2 and π RF pulses; τ = 630 ns; 16-step phase cycling applied only for detection sequence, 7520 acquisitions per T, including phase cycling; 8 T's denoted as VD in the table below logarithmically spaced between 0.5 μs and 16 μs; $T_R^{LF}$ = 25 μs; imaging time 10 minutes.

TABLE 1-continued

Pulse sequences.

Protocol | | | | | | | | | Description

| IRESE | N | First pulse | First delay | Second pulse | Second delay | Third pulse | Third delay | Detection channel Re | Detection channel Im |
|---|---|---|---|---|---|---|---|---|---|
| | 1 | X | VD | 0.5X | 630 ns | X | 630 ns | A | B |
| | 2 | X | VD | 0.5X | 630 ns | −X | 630 ns | A | B |
| | 3 | X | VD | 0.5X | 630 ns | Y | 630 ns | −A | −B |
| | 4 | X | VD | 0.5X | 630 ns | −Y | 630 ns | −A | −B |
| | 5 | X | VD | −0.5X | 630 ns | X | 630 ns | −A | −B |
| | 6 | X | VD | −0.5X | 630 ns | −X | 630 ns | −A | −B |
| | 7 | X | VD | −0.5X | 630 ns | Y | 630 ns | A | B |
| | 8 | X | VD | −0.5X | 630 ns | −Y | 630 ns | A | B |
| | 9 | X | VD | 0.5Y | 630 ns | X | 630 ns | B | −A |
| | 10 | X | VD | 0.5Y | 630 ns | −X | 630 ns | B | −A |
| | 11 | X | VD | 0.5Y | 630 ns | Y | 630 ns | −B | A |
| | 12 | X | VD | 0.5Y | 630 ns | −Y | 630 ns | −B | A |
| | 13 | X | VD | −0.5Y | 630 ns | X | 630 ns | −B | A |
| | 14 | X | VD | −0.5Y | 630 ns | −X | 630 ns | −B | A |
| | 15 | X | VD | −0.5Y | 630 ns | Y | 630 ns | B | −A |
| | 16 | X | VD | −0.5Y | 630 ns | −Y | 630 ns | B | −A |

$\pi/2$-$\tau$-$\pi/2$-T-$\pi/2$-$\tau$-echo; 60 ns RF pulses; $\tau = 550$ ns; 32-step phase cycling, 12160 acquisitions per T, including phase cycling; 8 T's denoted as VD in the table below logarithmically spaced between 0.45 µs and 7 µs; repetition time 20 µs; imaging time 10 minutes.

| SE | N | First pulse | First delay | Second pulse | Second delay | Third pulse | Third delay | Detection channel Re | Detection channel Im |
|---|---|---|---|---|---|---|---|---|---|
| | 1 | 0.5X | 630 ns | 0.5X | VD | 0.5X | 630 ns | A | B |
| | 2 | 0.5X | 630 ns | 0.5X | VD | −0.5X | 630 ns | −A | −B |
| | 3 | 0.5X | 630 ns | 0.5X | VD | 0.5Y | 630 ns | −B | A |
| | 4 | 0.5X | 630 ns | 0.5X | VD | −0.5Y | 630 ns | B | −A |
| | 5 | 0.5X | 630 ns | −0.5X | VD | 0.5X | 630 ns | −A | −B |
| | 6 | 0.5X | 630 ns | −0.5X | VD | −0.5X | 630 ns | A | B |
| | 7 | 0.5X | 630 ns | −0.5X | VD | 0.5Y | 630 ns | B | −A |
| | 8 | 0.5X | 630 ns | −0.5X | VD | −0.5Y | 630 ns | −B | A |
| | 9 | −0.5X | 630 ns | 0.5X | VD | 0.5X | 630 ns | −A | −B |
| | 10 | −0.5X | 630 ns | 0.5X | VD | −0.5X | 630 ns | A | B |
| | 11 | −0.5X | 630 ns | 0.5X | VD | 0.5Y | 630 ns | B | −A |
| | 12 | −0.5X | 630 ns | 0.5X | VD | −0.5Y | 630 ns | −B | A |
| | 13 | −0.5X | 630 ns | −0.5X | VD | 0.5X | 630 ns | A | B |
| | 14 | −0.5X | 630 ns | −0.5X | VD | −0.5X | 630 ns | −A | −B |
| | 15 | −0.5X | 630 ns | −0.5X | VD | 0.5Y | 630 ns | −B | A |
| | 16 | −0.5X | 630 ns | −0.5X | VD | −0.5Y | 630 ns | B | −A |
| | 17 | −0.5Y | 630 ns | 0.5X | VD | 0.5X | 630 ns | B | −A |
| | 18 | −0.5Y | 630 ns | 0.5X | VD | −0.5X | 630 ns | −B | A |
| | 19 | −0.5Y | 630 ns | 0.5X | VD | 0.5Y | 630 ns | A | B |
| | 20 | −0.5Y | 630 ns | 0.5X | VD | −0.5X | 630 ns | −A | −B |
| | 21 | −0.5Y | 630 ns | −0.5X | VD | 0.5X | 630 ns | −B | A |
| | 22 | −0.5Y | 630 ns | −0.5X | VD | −0.5X | 630 ns | B | −A |
| | 23 | −0.5Y | 630 ns | −0.5X | VD | 0.5Y | 630 ns | −A | −B |
| | 24 | −0.5Y | 630 ns | −0.5X | VD | −0.5Y | 630 ns | A | B |
| | 25 | 0.5Y | 630 ns | 0.5X | VD | 0.5X | 630 ns | −B | A |
| | 26 | 0.5Y | 630 ns | 0.5X | VD | −0.5X | 630 ns | B | −A |
| | 27 | 0.5Y | 630 ns | 0.5X | VD | 0.5Y | 630 ns | −A | −B |
| | 28 | 0.5Y | 630 ns | 0.5X | VD | −0.5Y | 630 ns | A | B |
| | 29 | 0.5Y | 630 ns | −0.5X | VD | 0.5X | 630 ns | B | −A |
| | 30 | 0.5Y | 630 ns | −0.5X | VD | −0.5X | 630 ns | −B | A |
| | 31 | 0.5Y | 630 ns | −0.5X | VD | 0.5Y | 630 ns | A | B |
| | 32 | 0.5Y | 630 ns | −0.5X | VD | −0.5Y | 630 ns | −A | −B |

$\pi/2$-FID; 70 ns $\pi/2$ RF pulses; 4-step phase cycling 16640 echoes, including phase cycling; 8 images with different repetition times logarithmically spaced between 10 µs and 25 µs; imaging time 10 minutes.

| SFR SPI | N | First pulse | First delay | Detection channel Re | Detection channel Im |
|---|---|---|---|---|---|
| | 1 | 0.5X | 1000 ns | A | B |
| | 2 | −0.5X | 1000 ns | −A | −B |
| | 3 | 0.5Y | 1000 ns | −B | A |
| | 4 | −0.5Y | 1000 ns | B | −A |

TABLE 1-continued

Pulse sequences.

| Protocol | Description |
|---|---|
| | $\pi$-T-$\pi/2$-did; 35 ns $\pi/2$ and $\pi$ RF pulses; 4-step phase cycling applied only for detection sequence, 7520 acquisitions per T, including phase cycling; 8 T's denoted as VD in the table below logarithmically spaced between 0.5 µs and 16 µs; $T^{LF}_R$ = 25 µs; imaging time 10 minutes. |

| IRSPI | N | First pulse | First delay | Second pulse | Second delay | Detection channel Re | Detection channel Im |
|---|---|---|---|---|---|---|---|
| | 1 | X | VD | 0.5X | 1000 ns | A | B |
| | 2 | X | VD | 0.5X | 1000 ns | −A | −B |
| | 3 | X | VD | 0.5X | 1000 ns | −B | A |
| | 4 | X | VD | 0.5X | 1000 ns | B | −A |

TABLE 2

Parameters of pulse sequences

| Pulse Sequence | Pulse length | RF power (W) | Bandwidth (MHz) | Transmitted Average Power (W) |
|---|---|---|---|---|
| 2pESE ($T_{2e}$) | 35 ns, $\pi/2$ and $\pi$ | 39.6($\pi/2$), 158.5($\pi$) | 8.7 | 0.56 |
| SFR ESE ($T_{1e}$) | 35 ns, $\pi/2$ and $\pi$ | 39.6($\pi/2$), 158.5($\pi$) | 8.7 | 0.4 |
| IRESE ($T_{1e}$) | 35 ns, $\pi/2$ and $\pi$ | 39.6($\pi/2$), 158.5($\pi$) | 8.7 | 0.33 |
| SE ($T_{1e}$) | 60 ns, all $\pi/2$ | 12.6 | 9.7 | 0.1 |

TABLE 3

Relaxation times and precision for 0% $O_2$ 1 mM sample

| Pulse Sequence | $T_{2e}$ or $T_{1e}$ (µs) | Standard deviation $T_{2e}$ or $T_{1e}$ (µs) |
|---|---|---|
| 2pESE ($T_{2e}$) | 5.15 | 0.19 |
| SFR ESE ($T_{1e}$) | 6.2 | 1.4 |
| IRESE ($T_{1e}$) | 5.9 | 0.29 |
| SE ($T_{1e}$) | 5.8 | 0.38 |

Non-imaging relaxation times:
$T_{2e}$ = 5.07 µs (2pESE);
$T_{1e}$ = 5.8 µs (IRESE);
$T_{1e}$ = 5.87 µs (SE)

TABLE 4

Relaxation times and precision for 9.3% $O_2$ 1 mM sample.

| Pulse Sequence | $T_{2e}$ or $T_{1e}$ (µs) | Standard deviation $T_{2e}$ or $T_{1e}$ (µs) |
|---|---|---|
| 2pESE ($T_{2e}$) | 1.25 | 0.07 |
| SFR ESE ($T_{1e}$) | N/A* | N/A* |
| IRESE($T_{1e}$) | 1.31 | 0.15 |
| SE($T_{1e}$) | 1.35 | 0.23 |

*the SFR sequence was unable to produce precise measurement due to $T_{1e}$ considerably smaller than the minimum repetition time that can be achieve in our system.
Non-imaging relaxation times:
$T_{2e}$ = 1.24 µs (2pESE);
$T_{1e}$ = 1.33 µs (IRESE);
$T_{1e}$ = 1.31 µs (SE).

REFERENCES FOR THE ABOVE SECTION #1

{110. Matsumoto 2006; cited fully below}
{46. Epel, 2008 #2200; cited fully below}

Additional References for the Above Section #2

{1.} Hall, E. J.; Radiobiology for the Radiologist, Edn. Fifth. (Lippincott Williams & Wilkins, Philadelphia; 2000). (Reference #1012 in the text above.)

{2.} Gatenby, R. A. et al.; Oxygen distribution in squamous cell carcinoma metastases and its relationship to outcome of radiation therapy. *Int. J. Radiat. Oncol. Biol. Phys.* 14, 831-838 (1988). (Reference #21 in the text above.)

{3.} Brizel, D. et al.; Tumor oxygenation predicts for the likelihood of distant metastases in human soft tissue sarcoma. *Cancer Res* 56, 941-943 (1996). (Reference #695 in the text above.)

{4.} Brizel, D. M., Dodge, R. K., Clough, R. W. & Dewhirst, M. W.; Oxygenation of head and neck cancer: changes during radiotherapy and impact on treatment outcome. *Radiother Oncol* 53, 113-117. (1999). (Reference #1121 in the text above.)

{5.} Brizel, D. M. et al.; Tumor oxygenation predicts for the likelihood of distant metastases in human soft tissue sarcoma. *Cancer Res* 56, 941-943. (1996). (Reference #1124 in the text above.)

{6.} Brizel, D. M., Sibley, G. S., Prosnitz, L. R., Scher, R. L. & Dewhirst, M. W.; Tumor hypoxia adversely affects the prognosis of carcinoma of the head and neck. *Int J Radiat Oncol Biol Phys* 38, 285-289. (1997). (Reference #1123 in the text above.)

{7.} Hockel, M. et al.; Association between tumor hypoxia and malignant progression in advanced cancer of the uterine cervix. *Cancer Res* 56, 4509-4515. (1996). (Reference #1111 in the text above.)

{8.} Shibata, T., Giaccia, A. J. & Brown, J. M.; Hypoxia-inducible regulation of a prodrug-activating enzyme for tumor-specific gene therapy. *Neoplasia* 4, 40-48 (2002). (Reference #1657 in the text above.)

{9.} Graeber, T. G. et al.; Hypoxia-mediated selection of cells with diminished apoptotic potential in solid tumours. *Nature* 379, 88-91 (1996). (Reference #942 in the text above.)

{10.} Semenza, G. L.; Hypoxia-inducible factor 1: master regulator of O2 homeostasis. *Curr Opin Genet Dev* 8, 588-594 (1998). (Reference #1693 in the text above.)

{11.} Carmeliet, P. et al.; Role of HIF-1alpha in hypoxia-mediated apoptosis, cell proliferation and tumour angiogenesis. *Nature* 394, 485-490. (1998). (Reference #1132 in the text above.)

{12.} Elas, M. et al.; Electron paramagnetic resonance oxygen images correlate spatially and quantitatively with Oxylite oxygen measurements. *Clin Cancer Res* 12, 4209-4217 (2006). (Reference #1906 in the text above.)

{13.} Elas, M. et al.; Electron paramagnetic resonance oxygen image hypoxic fraction plus radiation dose strongly correlates with tumor cure in FSa fibrosarcomas. *Int J Radiat Oncol Biol Phys* 71, 542-549 (2008). (Reference #2117 in the text above.)

{14.} Alberts, B. et al.; Molecular Biology of the Cell, Edn. 5th. (Garland Science, New York, Milton Park UK; 2008). (Reference #2096 in the text above.)

{15.} Fischbach, C. et al.; Cancer cell angiogenic capability is regulated by 3D culture and integrin engagement. *Proc Natl Acad Sci USA* (2009). (Reference #2089 in the text above.)

{16.} Alam, J. & Cook, J. L.; Reporter genes: application to the study of mammalian gene transcription. *Anal Biochem* 188, 245-254 (1990). (Reference #1662 in the text above.)

{17.} Holt, S. J. & Sadler, P. W.; Studies in enzyme cytochemistry. II. Synthesis of indigogenic substrates for esterases. *Proc R Soc Lond B Biol Sci* 148, 481-494 (1958). (Reference #1663 in the text above.)

{18.} Chalfie, M., Tu, Y., Euskirchen, G., Ward, W. W. & Prasher, D. C.; Green fluorescent protein as a marker for gene expression. *Science* 263, 802-805 (1994). (Reference #1664 in the text above.)

{19.} Weissleder, R. & Ntziachristos, V.; Shedding light onto live molecular targets. *Nat Med* 9, 123-128 (2003). (Reference #1694 in the text above.)

{20.} McCaffrey, A., Kay, M. A. & Contag, C. H.; Advancing molecular therapies through in vivo bioluminescent imaging. *Mol Imaging* 2, 75-86 (2003). (Reference #1692 in the text above.)

{21.} Blasberg, R. G.; In vivo molecular-genetic imaging: multi-modality nuclear and optical combinations. *Nucl Med Biol* 30, 879-888 (2003). (Reference #1681 in the text above.)

{22.} Massoud, T. F. & Gambhir, S. S.; Molecular imaging in living subjects: seeing fundamental biological processes in a new light. *Genes Dev* 17, 545-580 (2003). (Reference #1687 in the text above.)

{23.} Herschman, H. R.; Molecular imaging: looking at problems, seeing solutions. *Science* 302, 605-608 (2003). (Reference #1684 in the text above.)

{24.} Dothager, R. S. & Piwnica-Worms, D.; Molecular imaging of pulmonary disease in vivo. *Proc Am Thorac Soc* 6, 403-410 (2009). (Reference #2227 in the text above.)

{25.} Zhang, W. et al.; Rapid in vivo functional analysis of transgenes in mice using whole body imaging of luciferase expression. *Transgenic Res* 10, 423-434 (2001). (Reference #1695 in the text above.)

{26.} Adams, J. Y. et al.; Visualization of advanced human prostate cancer lesions in living mice by a targeted gene transfer vector and optical imaging. *Nat Med* 8, 891-897 (2002). (Reference #1680 in the text above.)

{27.} Kirkpatrick, J. P., Oleson, J. R. & Dewhirst, M. W.; in Radiation Research St. Louis, MO, USA; 2004). (Reference #1691 in the text above.)

{28.} Dewhirst, M. W. et al.; Microvascular studies on the origins of perfusion-limited hypoxia. *Br J Cancer Suppl* 27, S247-251 (1996). (Reference #1775 in the text above.)

{29.} Schober, O., Rahbar, K. & Riemann, B.; Multimodality molecular imaging—from target description to clinical studies. *Eur J Nucl Med Mol Imaging* (2009). (Reference #2099 in the text above.)

{30.} Sun, X. et al.; Quantitative imaging of gene induction in living animals. *Gene Ther* 8, 1572-1579 (2001). (Reference #1374 in the text above.)

{31.} Blasberg, R. G. & Tjuvajev, J. G.; Molecular-genetic imaging: current and future perspectives. *J Clin Invest* 111, 1620-1629 (2003). (Reference #1665 in the text above.)

{32.} Beekman, F. & van der Have, F.; The pinhole: gateway to ultra-high-resolution three-dimensional radionuclide imaging. *Eur J Nucl Med Mol Imaging* 34, 151-161 (2007). (Reference #2100 in the text above.)

{33.} Raleigh, J. et al.; Development of an ELISA for the detection of 2-nitroimidazole hypoxia markers bound to tumor tissue. *Int J Radiat Oncol Biol Phys* 22, 403-405 (1992). (Reference #765 in the text above.)

{34.} Evans, S. M., Jenkins, W. T., Joiner, B., Lord, E. M. & Koch, C. J.; 2-Nitroimidazole (EFS) binding predicts radiation resistance in individual 9L s.c. tumors. *Cancer Res.* 56, 405-411 (1996). (Reference #931 in the text above.)

{35.} Lewis, J. S., McCarthy, D. W., McCarthy, T. J., Fujibayashi, Y. & Welch, M. J.; Evaluation of 64Cu-ATSM in vitro and in vivo in a hypoxic tumor model. *J Nucl Med* 40, 177-183 (1999). (Reference #1371 in the text above.)

{36.} Melo, T., Ballinger, J. R. & Rauth, A. M.; Role of NADPH:cytochrome P450 reductase in the hypoxic accumulation and metabolism of BRU59-21, a technetium-99m-nitroimidazole for imaging tumor hypoxia. *Biochem Pharmacol* 60, 625-634 (2000). (Reference #2229 in the text above.)

{37.} Louie, A. Y. et al.; In vivo visualization of gene expression using magnetic resonance imaging. *Nat Biotechnol* 18, 321-325 (2000). (Reference #1395 in the text above.)

{38.} Weissleder, R. et al.; In vivo magnetic resonance imaging of transgene expression. *Nat Med* 6, 351-355 (2000). (Reference #1673 in the text above.)

{39.} Vaughan, J. T. et al.; Whole-body imaging at 7T: preliminary results. *Magn Reson Med* 61, 244-248 (2009). (Reference #2230 in the text above.)

{40.} Halpern, H. J. et al.; An imaging radiofrequency electron spin resonance spectrometer with high resolution and sensitivity for in vivo measurements. *Rev. Sci. Instrum.* 60, 1040-1050 (1989). (Reference #89 in the text above.)

{41.} Halpern, H. J. & Bowman, M. K. (eds.); EPR Imaging at MHz frequencies. (CRC Press, Boca Raton, FL; 1991). (Reference #899 in the text above.)

{42.} Halpern, H. J. in In Vivo EPR(ESR): Theory and Applications, Vol. 18. (ed. L. J. Berliner) (Kluwer Academic/Plenum Pub Corp, New York; 2003). (Reference #1798 in the text above.)

{43.} Lauterbur, P. C., Levin, D. N. & Marr, R. B.; Theory and simulation of NMR spectroscopic imaging and field plotting by projection reconstruction involving an intrinsic frequency dimension. *J. Magn. Reson.* 59, 536-541 (1984). (Reference #177 in the text above.)

{44.} Maltempo, M. M.; Differentiation of spectral and spatial components in EPR imaging using 2-D image reconstruction algorithms. *J. Magn. Reson.* 69, 156-161 (1986). (Reference #181 in the text above.)

{45.} Halpern, H. J. et al.; Oxymetry deep in tissues with low-frequency electron paramagnetic resonance. *Proc. Natl. Acad. Sci. USA* 91, 13047-13051 (1994). (Reference #93 in the text above.)

{46.} Epel, B., Sundramoorthy, S. V., Mailer, C. & Halpern, H. J.; A versatile high speed 250-MHz pulse imager for biomedical applications. *Concept Magn Reson B* 33B, 163-176 (2008). (Reference #2200 in the text above.)

{47.} Haney, C. R. et al.; Characterization of response to radiation mediated gene therapy by means of multimodality imaging. *Magn Reson Med* 62, 348-356 (2009). (Reference #2194 in the text above.)

{48.} Colton, T.; Statistics in Medicine. (Little, Brown & Co., Boston; 1974). (Reference #1724 in the text above.)

{49.} Shibata, T., Giaccia, A. J. & Brown, J. M.; Development of a hypoxia-responsive vector for tumor-specific gene therapy. *Gene Ther* 7, 493-498 (2000). (Reference #1659 in the text above.)

{50.} Wilson, S. R., Gallagher, S., Warpeha, K. & Hawthorne, S. J.; Amplification of MMP-2 and MMP-9 production by prostate cancer cell lines via activation of protease-activated receptors. *Prostate* 60, 168-174 (2004). (Reference #2083 in the text above.)

{51.} Mechtcheriakova, D., Wlachos, A., Holzmuller, H., Binder, B. R. & Hofer, E.; Vascular endothelial cell growth factor-induced tissue factor expression in endothelial cells is mediated by EGR-1. *Blood* 93, 3811-3823 (1999). (Reference #2087 in the text above.)

{52.} Castro, B., Dormoy, J. R., Evin, G. & Selve, C.; Reactions of Peptide Bond 0.4. Benzotriazonyl-N-Oxytridimelthylamino Phosphonium Hexafluorophosphate (Bop). *Tetrahedron Lett,* 1219-1222 (1975). (Reference #2093 in the text above.)

{53.} Bremer, C., Bredow, S., Mahmood, U., Weissleder, R. & Tung, C. H.; Optical imaging of matrix metalloproteinase-2 activity in tumors: feasibility study in a mouse model. *Radiology* 221, 523-529 (2001). (Reference #1407 in the text above.)

{54.} Rosen, G. M. et al.; Dendrimeric-containing nitronyl nitroxides as spin traps for nitric oxide: Synthesis, kinetic and stability studies. *Macromolecules* 36, 1021-1027 (2003). (Reference #1548 in the text above.)

{55.} Alberts, B. et al.; Molecular Biology of the Cell, Edn. 3rd. (Garland, New York; 1994). (Reference #40 in the text above.)

{56.} Halpern, H. J. et al.; Selective isotopic labeling of a nitroxide spin label to enhance sensitivity for T2 oxymetry. *J. Magn. Reson.* 90, 40-51 (1990). (Reference #850 in the text above.)

{57.} Halpern, H. J., Peric, M., Yu, C. & Bales, B. L.; Rapid quantitation of parameters from inhomogeneously broadened EPR spectra. *J. Magn. Reson.* A103, 13-22 (1993). (Reference #91 in the text above.)

{58.} Fink, T., Kazlauskas, A., Poellinger, L., Ebbesen, P. & Zachar, V.; Identification of a tightly regulated hypoxia-response element in the promoter of human plasminogen activator inhibitor-1. *Blood* 99, 2077-2083 (2002). (Reference #1676 in the text above.)

{59.} Stephen, R. M. & Gillies, R. J.; Promise and progress for functional and molecular imaging of response to targeted therapies. *Pharm Res* 24, 1172-1185 (2007). (Reference #2084 in the text above.)

{60.} Gillespie, D. L. et al.; Silencing of hypoxia inducible factor-1alpha by RNA interference attenuates human glioma cell growth in vivo. *Clin Cancer Res* 13, 2441-2448 (2007). (Reference #2085 in the text above.)

{61.} Lungu, G. F., Li, M. L., Xie, X., Wang, L. V. & Stoica, G.; In vivo imaging and characterization of hypoxia-induced neovascularization and tumor invasion. *Int J Oncol* 30, 45-54 (2007). (Reference #2086 in the text above.)

{62.} Schabbauer, G. et al.; Nuclear factor of activated T cells and early growth response-1 cooperate to mediate tissue factor gene induction by vascular endothelial growth factor in endothelial cells. *Thromb Haemost* 97, 988-997 (2007). (Reference #2095 in the text above.)

{63.} Timke, C. et al.; Combination of vascular endothelial growth factor receptor/platelet-derived growth factor receptor inhibition markedly improves radiation tumor therapy. *Clin Cancer Res* 14, 2210-2219 (2008). (Reference #2091 in the text above.)

{64.} Pourgholami, M. H. & Morris, D. L.; Inhibitors of vascular endothelial growth factor in cancer. *Cardiovasc Hematol Agents Med Chem* 6, 343-347 (2008). (Reference #2088 in the text above.)

{65.} Burks, S. R. et al.; 2H,15N-Substituted nitroxides for measuring oxygen concentration: Implications for in vivo oxymetry using electron paramagnetic resonance imaging. *Magn Reson Med* Submitted (2009). (Reference #2081 in the text above.)

{66.} Lin, Y. J., Teicher, B. A. & Halpern, H. J.; Synthesis of 4-proto-3-carbamoyl-2,2,5,5-tetraperdeuteromethyl-3-pyrrolin-1-xsloyxy (mHCTPO): A selectively isotopically labeled compound for use in T2 spin label oxymetry. *J. Labelled Comp. Radiopharmaceut.* 28, 621-631 (1990). (Reference #118 in the text above.)

{67.} Burks, S. R. et al.; Optimization of labile esters for esterase-assisted accumulation of nitroxides into cells: a model for in vivo EPR imaging. *Bioconjug Chem* 19, 2068-2071 (2008). (Reference #2101 in the text above.)

{68.} Haney, C. R. et al.; Reduction of image artifacts in mice by bladder flushing with a novel double-lumen urethral catheter. *Mol Imaging* 5, 175-179 (2006). (Reference #1876 in the text above.)

{69.} Wells, W. M., 3rd, Viola, P., Atsumi, H., Nakajima, S. & Kikinis, R.; Multi-modal volume registration by maximization of mutual information. *Med Image Anal* 1, 35-51. (1996). (Reference #1214 in the text above.)

{70.} Studholme, C., Hill, D. L. & Hawkes, D. J.; Automated 3-D registration of MR and CT images of the head. *Med Image Anal* 1, 163-175. (1996). (Reference #1215 in the text above.)

{71.} Studholme, C., Hill, D. L. & Hawkes, D. J.; Automated three-dimensional registration of magnetic resonance and positron emission tomography brain images by multiresolution optimization of voxel similarity measures. *Med Phys* 24, 25-35. (1997). (Reference #1216 in the text above.)

{72.} Thurston, G. & Kitajewski, J.; VEGF and Delta-Notch: interacting signalling pathways in tumour angiogenesis. *Br J Cancer* 99, 1204-1209 (2008). (Reference #2090 in the text above.)

Each of the references cited herein is incorporated herein by reference. (The numbers 73 to 100 are not used herein for references.)

{101.} H. J. Halpern, D. P. Spencer, J. Vanpolen, M. K. Bowman, A. C. Nelson, E. M. Dowey, and B. A. Teicher, Imaging Radio-Frequency Electron-Spin-Resonance Spectrometer with High-Resolution and Sensitivity for In vivo Measurements. Rev. Sci. Instrum. 60 (1989) 1040-1050. {Note—this reference is the same as 40. Halpern 1989 #89}

{102.} P. Kuppusamy, M. Chzhan, K. Vij, M. Shteynbuk, D. J. Lefer, E. Giannella, and J. L. Zweier, 3-Dimensional Spectral Spatial EPR Imaging of Free-Radicals in the Heart—a Technique for Imaging Tissue Metabolism and Oxygenation. Proc. Natl Acad. Sci. USA 91 (1994) 3388-3392.

{103.} M. Elas, B. B. Williams, A. Parasca, C. Mailer, C. A. Pelizzari, M. A. Lewis, J. N. River, G. S. Karczmar, E. D. Barth, and H. J. Halpern, Quantitative tumor oxymetric images from 4D electron paramagnetic resonance imaging (EPRI): Methodology and comparison with blood oxygen level-dependent (BOLD) MRI. Magnet Reson Med 49 (2003) 682-691.

{104.} C. Mailer, S. V. Sundramoorthy, C. A. Pelizzari, and H. J. Halpern, Spin echo spectroscopic electron paramagnetic resonance imaging. Magnet Reson Med 55 (2006) 904-912.

{105.} B. Epel, C. R. Haney, D. Hleihel, C. Wardrip, E. D. Barth, and H. J. Halpern, Electron paramagnetic resonance oxygen imaging of a rabbit tumor using localized spin probe delivery. Medical Physics 37 (2010) 2553-2559.

{106.} S. Subramanian, N. Devasahayam, R. Murugesan, K. Yamada, J. Cook, A. Taube, J. B. Mitchell, J. A. B. Lohman, and M. C. Krishna, Single-point (constant-time) imaging in radiofrequency Fourier transform electron paramagnetic resonance. Magnet Reson Med 48 (2002) 370-379.

{107.} C. P. Slichter, Principles of Magnetic Resonance, Springer-Verlag, New York, 1996.

{108.} J. H. Ardenkjaer-Larsen, I. Laursen, I. Leunbach, G. Ehnholm, L. G. Wistrand, J. S. Petersson, and K. Golman, EPR and DNP properties of certain novel single electron contrast agents intended for oximetric imaging. J. Magn. Reson. 133 (1998) 1-12.

{109.} B. Epel, S. V. Sundramoorthy, C. Mailer, and H. J. Halpern, A versatile high speed 250-MHz pulse imager for biomedical applications. Conc. Magn. Reson. B 33B (2008) 163-176. {Note—this is the same as 46. Epel, 2008 #2200}

{110.} K. Matsumoto, S. Subramanian, N. Devasahayam, T. Aravalluvan, R. Murugesan, J. A. Cook, J. B. Mitchell, and M. C. Krishna, Electron paramagnetic resonance imaging of tumor hypoxia: Enhanced spatial and temporal resolution for in vivo $pO_2$ determination. Magnet Reson Med 55 (2006) 1157-1163.

{111.} N. Devasahayam, S. Subramanian, R. Murugesan, F. Hyodo, K. I. Matsumoto, J. B. Mitchell, and M. C. Krishna, Strategies for improved temporal and spectral resolution in in vivo oximetric imaging using time-domain EPR. Magnet Reson Med 57 (2007) 776-783.

{112.} G. R. Eaton, and S. S. Eaton, EPR Imaging Using $T_1$ Selectivity. J. Magn. Reson. 71 (1987) 271-275.

{113.} A. Schweiger, and G. Jeschke, Principles of Pulse Electron Paramagnetic Resonance, Oxford University Press, 2001.

{114.} L. Kevan, and M. K. Bowman, (Eds.), Modern Pulsed and Continuous Wave Electron Spin Resonance, Wiley & Sons, 1990.

{115.} R. W. Quine, G. R. Eaton, and S. Dillon, Fast-response VHF pulsed 2 KW power amplifiers. Conc. Magn. Reson. B 29B (2006) 185-190.

{116.} S. V. Sundramoorthy, B. Epel, C. Mailer, and H. J. Halpern, A Passive Dual-Circulator Based Transmit/Receive Switch for Use with Reflection Resonators in Pulse Electron Paramagnetic Resonance. Conc. Magn. Reson. B 35B (2009) 133-138.

{117.} R. W. Quine, M. Tseytlin, S. S. Eaton, and G. R. Eaton, A Very Fast Switched-Attenuator Circuit for Microwave and RF Applications. Conc. Magn. Reson. B 37B (2010) 39-44.

{118.} B. Epel, I. Gromov, S. Stoll, A. Schweiger, and D. Goldfarb, Spectrometer manager: A versatile control software for pulse EPR spectrometers. Conc. Magn. Reson. B 26B (2005) 36-45.

{119.} G. R. Eaton, S. S. Eaton, and K. Ohno, EPR Imaging and in vivo EPR, CRC Press, Boca Raton FL, 1991.

{120.} K. H. Ahn, and H. J. Halpern, Spatially uniform sampling in 4-D EPR spectral-spatial imaging. J. Magn. Reson. 185 (2007) 152-158.

{121.} K. H. Ahn, and H. J. Halpern, Comparison of local and global angular interpolation applied to spectral-spatial EPR image reconstruction. Medical Physics 34 (2007) 1047-1052.

{122.} M. Elas, R. Bell, D. Hleihel, E. D. Barth, C. Mcfaul, C. R. Haney, J. Bielanska, K. Pustelny, K. H. Ahn, C. A. Pelizzari, M. Kocherginsky, and H. J. Halpern, Electron paramagnetic resonance oxygen image hypoxic fraction plus radiation dose strongly correlates with tumor cure in FSA fibrosarcomas. International Journal of Radiation Oncology Biology Physics 71 (2008) 542-549.

{123.} S. Matsumoto, M. G. Espey, H. Utsumi, N. Devasahayam, K. I. Matsumoto, A. Matsumoto, H. Hirata, D. A. Wink, P. Kuppusamy, S. Subramanian, J. B. Mitchell, and M. C. Krishna, Dynamic monitoring of localized tumor oxygenation changes using RF pulsed electron paramagnetic resonance in conscious mice. Magnet Reson Med 59 (2008) 619-625.

{124.} Carmeliet, P. and R. K. Jain (2000). "Angiogenesis in cancer and other diseases." Nature 407(6801): 249-257.

{125.} Forsythe, J. A., B. H. Jiang, et al. (1996). "Activation of vascular endothelial growth factor gene transcription by hypoxia-inducible factor 1." Mol Cell Biol 16(9): 4604-4613.

{126.} Li, F., P. Sonveaux, et al. (2007). "Regulation of HIF-1alpha stability through S-nitrosylation." Mol Cell 26(1): 63-74.

{127.} Picchio, M., R. Beck, et al. (2008). "Intratumoral spatial distribution of hypoxia and angiogenesis assessed by 18F-FAZA and 125I-Gluco-RGD autoradiography." J Nucl Med 49(4): 597-605.

{128.} Sandler, A. (2007). "Bevacizumab in non small cell lung cancer." Clin Cancer Res 13(15 Pt 2): s4613-4616.

{129.} Suit, H. D. (1984). "Modification of radiation response." Int J Radiat Oncol Biol Phys 10(1): 101-108.

In some embodiments, a series of measurements are made, each using a set of three excitation pulses. In some embodiments, each set of three pulses includes a pulse sequence, wherein each pulse has a phase relative to X-Y polar coordinates, wherein a unity magnitude pulse with zero phase shift is considered to be an 1.0 X pulse (also called simply an X pulse); a unity magnitude pulse with 0.5 pi radian (90 degrees) phase shift is considered to be an 1.0 Y pulse (also called simply a Y pulse); a unity magnitude pulse with 1.0 pi radian (180 degrees) phase shift is considered to be an −1.0 X pulse (also called simply a −X pulse); a unity magnitude pulse with 1.5 pi radians (270 degrees) phase shift is considered to be an −1.0 Y pulse (also called simply a −Y pulse). In like manner, pulses having half that magnitude and a 0-degree phase shift are called 0.5X pulses, those with a 90-degree phase shift are called 0.5Y pulses, those with a 180-degree phase shift are called −0.5X pulses, and those with a 270-degree phase shift are called −0.5Y pulses. In some embodiments, the durations of each of the first, second and third pulse is about 35 ns (about 9 cycles of 250 MHz RF), with a phase delay denoted (+X, +Y, −X, and −Y) and a magnitude of unity (1) or half (0.5). The variable delay between the first pulse and the second pulse is denoted VD1 (also denoted as "t" in FIG. 1B), and the variable delay between the second pulse and the third pulse is denoted VD2 (also denoted as "r" in FIG. 1B). In some embodiments, a series of sets of pulses are successively generated such that sixteen sets of three pulses are generated for each of one or more first delays VD1 and each of one or more second delays VD2, as follows:

| Set | First pulse | First delay | Second pulse | Second delay | Third pulse |
|---|---|---|---|---|---|
| 1 | −X | VD1 | +.5X | VD2 | +Y |
| 2 | −X | VD1 | −.5X | VD2 | +Y |
| 3 | −X | VD1 | +.5X | VD2 | −Y |
| 4 | −X | VD1 | −.5X | VD2 | −Y |
| 5 | −X | VD1 | +.5Y | VD2 | +X |
| 6 | −X | VD1 | −.5Y | VD2 | +X |
| 7 | −X | VD1 | +.5Y | VD2 | −X |
| 8 | −X | VD1 | −.5Y | VD2 | −X |
| 9 | −X | VD1 | +.5Y | VD2 | +Y |
| 10 | −X | VD1 | −.5Y | VD2 | +Y |
| 11 | −X | VD1 | +.5Y | VD2 | −Y |
| 12 | −X | VD1 | −.5Y | VD2 | −Y |
| 13 | −X | VD1 | +.5X | VD2 | +X |
| 14 | −X | VD1 | −.5X | VD2 | +X |
| 15 | −X | VD1 | +.5X | VD2 | −X |
| 16 | −X | VD1 | −5X | VD2 | −X |

In some embodiments, after the third pulse, a third variable delay (also denoted as "r" in FIG. 1A2) is inserted before a period of the response RF signal is acquired, wherein in some embodiments, the response RF is acquired for a period of about 4 to 6 microseconds. In some embodiments, the magnitude, quadrature (or phase) and/or frequency of the response RF are measured, digitized and stored for later analysis and/or image reconstruction.

In some embodiments, the present invention provides an apparatus for electron paramagnetic resonance imaging (EPRI) of a volume of animal tissue in vivo. This apparatus includes a set of surface transmit coils; and a set of surface receive coils, wherein the set of surface transmit coils generates an excitation magnetic field in the volume of animal tissue in response to an applied electrical signal, and the set of surface receive coils generates a sensed electrical signal in response to a sensed magnetic field in the volume of animal tissue, and wherein the set of transmit coils and the set of receive coils are oriented relative to one another such that the sensed electrical signal has little or no component directly due to the excitation magnetic field, and wherein the set of surface receive coils is configured to detect electron paramagnetic resonance signals in the volume of animal tissue; and a pulsed-RF driver circuit, operatively coupled to the set of transmit coils, that drives a RF pulse set having a plurality of successive RF pulses, including a first pulse having a plurality of cycles of RF, followed by a first delay and thereafter by a second pulse that includes a plurality of cycles of RF that are shifted in phase (by about either zero radians (0 degrees), ½ pi radians (90 degrees), pi radians (180 degrees) or 3/2 pi radians (270 degrees)) relative to the first π-pulse, followed by a second delay and thereafter by a third pulse that includes a plurality of cycles of RF that are shifted in phase (by about either zero radians (0 degrees), ½ pi radians (90 degrees), pi radians (180 degrees) or 3/2 pi radians (270 degrees)) relative to the first pulse. In some embodiments, the animal tissue is human tissue in a living human.

Some embodiments further include a magnetic-field generator configured to generate a substantially static magnetic field in the volume of animal tissue, which is generally orthogonal to the excitation magnetic field and to the sensed magnetic field in the volume of animal tissue, and wherein the excitation magnetic field is generally orthogonal to the sensed magnetic field in the volume of animal tissue; an RF receiver circuit operatively coupled to the set of surface receive coils to receive the sensed electrical signal from the set of surface receive coils and to generate a received electrical signal; a digital-signal processor (DSP) unit operatively coupled to the RF receiver circuit and configured to process the received electrical signal and to generate image data; a storage unit operatively coupled to the DSP unit to receive and store the image data; and a display unit operatively coupled to the storage unit to receive and display the image data.

In some embodiments, the present invention provides a method for electron paramagnetic resonance oxygen imaging (EPROI) of a volume of animal tissue in vivo in an animal. This method includes placing (e.g., by injecting, ingesting, inhaling, swabbing or the like) a reporter molecule in the animal; applying an RF pulse sequence that elicits a $T_1$ spin-lattice relaxation response from the volume of tissue; and generating an EPRI image of in the animal using the $T_1$ response.

In some embodiments, the present invention provides a method for electron paramagnetic resonance imaging (EPRI) of a volume of animal tissue in vivo in an animal. This method includes generating a substantially static magnetic field in the volume of animal tissue; generating a excitation set that includes a plurality of RF-excitation magnetic-field pulses including a first pulse that includes a plurality of cycles of RF, followed by a first delay and then a second pulse that includes a plurality of cycles of RF that are shifted in phase (by about either zero radians (0 degrees), ½ pi radians (90 degrees), pi radians (180 degrees) or 3/2 pi radians (270 degrees)) relative to the cycles of the first pulse, followed by a second delay and thereafter a third pulse that includes a plurality of cycles of RF that are shifted in phase (by about either zero radians (0 degrees), ½ pi radians (90 degrees), pi radians (180 degrees) or 3/2 pi radians (270 degrees)) relative to the first pulse in the direction generally orthogonal to the substantially static magnetic field in the volume of animal tissue from a surface of the animal next to the volume of animal tissue. The method further includes sensing an RF magnetic field in a direction generally orthogonal to the substantially static magnetic field in the volume of animal tissue from a surface of the animal next to the volume of animal tissue, wherein the sensed RF magnetic field is in a direction generally orthogonal to the pulsed excitation magnetic field; generating a received electrical signal based on the sensed RF magnetic field; digitally signal processing the received electrical signal to generate image data; storing the image data; and displaying the image data.

In some embodiments, the present invention provides an apparatus and a corresponding method for improved signal-to-noise (S/N) measurements useful for electron paramagnetic resonance imaging (EPRI), in situ and in vivo, using high-isolation transmit/receive surface coils and temporally spaced pulses of RF energy (e.g., in some embodiments, a first pulse of about 9 cycles of an about-250-MHz signal) having an amplitude sufficient to invert or rotate the magnetization prepared in the temporally static magnetic fields by 180 degrees (a so called pi-pulse (π pulse)) followed closely, but at varied times, by a second radio-frequency pulse of about 9 cycles of substantially the same frequency but having an amplitude half that of the initial pulse to rotate the magnetization by, e.g., 90 degrees (a so called pi-over-two pulse (π/2 pulse)), to the horizontal plane where it evolves for a very short fixed time after which time a third radio-frequency pulse sufficient to rotate the magnetization by, e.g., 180 degrees, that allows the formation of an echo (in some embodiments, the cycles of the second pulse and third pulse are obtained from the same signal source as those of the first pulse but are phase shifted by respect to each other by 0, 90, 180, or 270 degrees to reduce signal artifact), which, in some embodiments, provide improved microenvironmental images that are representative of particular internal structures in the human body and spatially resolved images of tissue/cell protein signals responding to conditions (such as hypoxia) that show the temporal sequence of certain biological processes, and, in some embodiments, that distinguish malignant tissue from healthy tissue.

Embodiments within the scope of the present invention include a computer-readable medium for carrying or having computer-executable instructions or data structures stored thereon. Such computer-readable medium may be any available medium, which is accessible by a general-purpose or special-purpose computer system. By way of example, and not limitation, such computer-readable medium can comprise physical storage medium such as RAM, ROM, EPROM, CD-ROM or other optical-disk storage, magnetic-disk storage or other magnetic-storage devices, EEPROM or FLASH storage devices, or any other medium which can be used to carry or store desired program code means in the form of computer-executable instructions, computer-readable instructions, or data structures and which may be accessed by a general-purpose or special-purpose computer system. This physical storage medium may be fixed to the computer system as in the case of a magnetic drive or removable as in the case of an EEPROM device (e.g., FLASH storage device). In some embodiments, this physical storage medium may be accessible and/or downloadable over the internet.

In some embodiments, the present invention provides an apparatus for electron paramagnetic resonance oxygen imaging (EPROI) of a volume of animal tissue in vivo. This apparatus includes: a set of surface transmit coils; and a set of surface receive coils, wherein the set of surface transmit coils generates an excitation magnetic field in the volume of animal tissue in response to an applied electrical signal, and the set of surface receive coils generates a sensed electrical signal in response to a sensed magnetic field in the volume of animal tissue, and wherein the set of transmit coils and the set of receive coils are oriented relative to one another such that the sensed electrical signal has little or no component directly due to the excitation magnetic field, and wherein the set of surface receive coils is configured to detect electron paramagnetic resonance signals in the volume of animal tissue; a pulsed-RF driver circuit, operatively coupled to the set of transmit coils, that drives a plurality of pulse sets, each pulse set having a plurality of successive transmitted pulses, including a first pulse having a plurality of cycles of RF, followed by a first delay and thereafter by a second pulse that includes a plurality of cycles of RF, followed by a second delay and thereafter by a third pulse that includes a plurality of cycles of RF; and an RF receiver circuit operatively coupled to the set of surface receive coils to receive the sensed electrical signal from the set of surface receive coils and to generate a received electrical signal, wherein the transmitted pulses are of magnitudes and durations configured to measure $T_1$ spin-lattice relaxation in the volume of tissue.

In some embodiments of the apparatus, for different ones of the plurality of pulse sets, the second transmit pulses have RF cycles that are shifted in phase by a selected different amount (by about either 0 degrees, 90 degrees, 180 degrees or 270 degrees) relative to the first pulse, and the third pulses have RF cycles that are shifted in phase by a selected different amount (by about either 0 degrees, 90 degrees, 180 degrees or 270 degrees) relative to the first pulse.

In some embodiments of the apparatus, for each of the plurality of pulse sets:
the—first transmit pulse is a pi pulse having a magnitude and duration selected to rotate an electron paramagnetic resonance spin by pi radians;
the second transmit pulse is a pi/2 pulse having a magnitude and duration selected to rotate an electron paramagnetic resonance spin ½ pi radians; and
the third transmit pulse is a pi pulse having a magnitude and duration selected to rotate an electron paramagnetic resonance spin pi radians.

In some embodiments of the apparatus, for each of the plurality of pulse sets, the first, second and third transmit pulses form an inversion recovery with electron-spin echo detection (IRESE) sequence.

In some embodiments of the apparatus, for each of the plurality of pulse sets, the first, second and third transmit pulses form an inversion recovery with electron-spin echo detection (IRESE) sequence having a π-pulse as the first pulse, a T delay as the first delay, a π/2-pulse as the second pulse, a τ delay as the second delay, a π-pulse as the third pulse, a τ delay as the third delay, wherein the first, second and third pulses are each about 35 ns in duration, wherein the π/2 pulse rotates a magnetization π/2 radians and the π-pulses rotate a magnetization π radians, wherein τ=630 ns, wherein T has a value in a range of about 500 ns to about 16,000 ns, and wherein the cycles of RF have a frequency of about 250 MHz.

In some embodiments of the apparatus, for each of the plurality of pulse sets, the first, second and third transmit pulses form an inversion recovery with electron-spin echo detection (IRESE) sequence having a π-pulse as the first pulse, a T delay as the first delay, a π/2-pulse as the second pulse, a τ delay as the second delay, a π-pulse as the third pulse, a τ delay as the third delay, wherein the first, second and third pulses are each about 35 ns in duration, wherein the π/2 pulse rotates a magnetization π/2 radians and the π-pulses rotate a magnetization π radians, wherein τ=630 ns, wherein T has a value in a range of about 500 ns to about 16,000 ns, wherein the cycles of RF have a frequency of about 250 MHz, wherein the plurality of pulse sets apply a sixteen-step phase cycling, wherein about 7520 acquisitions are acquired per value of T and include phase cycling, wherein eight T values that are approximately logarithmically spaced between one-half microseconds (0.5 μs) and sixteen microseconds (16 μs) are used, wherein $T^{LF}_R$=25 μs, and wherein the phase cycling includes values selected from rows of the following table:

| First pulse | First delay | Second pulse | Second delay | Third pulse | Third delay | Detection channel Re (real) | Detection channel Im (imaginary) |
|---|---|---|---|---|---|---|---|
| X | T | 0.5X | 630 ns | X | 630 ns | A | B |
| X | T | 0.5X | 630 ns | -X | 630 ns | A | B |
| X | T | 0.5X | 630 ns | Y | 630 ns | -A | -B |
| X | T | 0.5X | 630 ns | -Y | 630 ns | -A | -B |
| X | T | -0.5X | 630 ns | X | 630 ns | -A | -B |
| X | T | -0.5X | 630 ns | -X | 630 ns | -A | -B |
| X | T | -0.5X | 630 ns | Y | 630 ns | A | B |
| X | T | -0.5X | 630 ns | -Y | 630 ns | A | B |
| X | T | 0.5Y | 630 ns | X | 630 ns | B | -A |
| X | T | 0.5Y | 630 ns | -X | 630 ns | B | -A |
| X | T | 0.5Y | 630 ns | Y | 630 ns | -B | A |
| X | T | 0.5Y | 630 ns | -Y | 630 ns | -B | A |
| X | T | -0.5Y | 630 ns | X | 630 ns | -B | A |
| X | T | -0.5Y | 630 ns | -X | 630 ns | -B | A |
| X | T | -0.5Y | 630 ns | Y | 630 ns | B | -A |
| X | T | -0.5Y | 630 ns | -Y | 630 ns | B | -A. |

Some embodiments of the apparatus further include a magnetic-field generator configured to generate a substantially static magnetic field in the volume of animal tissue, which is generally orthogonal to the excitation magnetic field and to the sensed magnetic field in the volume of animal tissue, and wherein the excitation magnetic field is generally orthogonal to the sensed magnetic field in the volume of animal tissue; a digital-signal processor (DSP) unit operatively coupled to the RF receiver circuit and configured to process the received electrical signal and to generate image data; a storage unit operatively coupled to the DSP unit to receive and store the image data; and a display unit operatively coupled to the storage unit to receive and display the image data.

In some embodiments, the present invention provides a method for electron paramagnetic resonance imaging (EPRI) of a volume of animal tissue in vivo in an animal. This method includes generating a substantially static magnetic field in the volume of animal tissue; and generating a plurality of pulse sets, wherein the generating of each one of the plurality of pulse sets includes: generating a first RF excitation magnetic field pulse having a plurality of RF cycles in a first direction generally orthogonal to the substantially static magnetic field in the volume of animal tissue from a surface of the animal next to the volume of animal tissue; delaying for a first delay time; generating a second RF excitation magnetic field pulse having a plurality of RF in the first direction generally orthogonal to the substantially static magnetic field; delaying for a second delay time; generating a third RF excitation magnetic field pulse having a plurality of RF in the first direction generally orthogonal to the substantially static magnetic field; delaying for a third delay time; sensing an RF spin-relaxation signal; and generating a received electrical signal based on the sensed RF signal; wherein the first, second and third RF excitation magnetic field pulses are of magnitudes and durations configured to measure $T_1$ spin-lattice relaxation in the volume of tissue. In some embodiments, the animal tissue is human tissue in a living human.

In some embodiments of the method, for different ones of the plurality of pulse sets, the second transmit pulses have RF cycles that are shifted in phase by a selected different amount (by about either 0 degrees, 90 degrees, 180 degrees or 270 degrees) relative to the first pulse, and the third pulses have RF cycles that are shifted in phase by a selected different amount (by about either 0 degrees, 90 degrees, 180 degrees or 270 degrees) relative to the first pulse.

In some embodiments of the method, for each of the plurality of pulse sets: the first transmit pulse is a pi pulse having a magnitude and duration selected to rotate an electron paramagnetic resonance spin by pi radians; the second transmit pulse is a pi/2 pulse having a magnitude and duration selected to rotate an electron paramagnetic resonance spin ½ pi radians; and the third transmit pulse is a pi pulse having a magnitude and duration selected to rotate an electron paramagnetic resonance spin pi radians.

In some embodiments of the method, for each of the plurality of pulse sets, the first, second and third transmit pulses form an inversion recovery with electron-spin echo detection (IRESE) sequence.

In some embodiments of the method, for each of the plurality of pulse sets, the first, second and third transmit pulses form an inversion recovery with electron-spin echo detection (IRESE) sequence having a π-pulse as the first pulse, a T delay as the first delay, a π/2-pulse as the second pulse, a τ delay as the second delay, a π-pulse as the third pulse, a τ delay as the third delay, wherein the first, second and third pulses are each about 35 ns in duration, wherein the π/2 pulse rotates a magnetization π/2 radians and the π-pulses rotate a magnetization π radians, wherein τ=630 ns, wherein T has a value in a range of about 500 ns to about 16,000 ns, and wherein the cycles of RF have a frequency of about 250 MHz.

In some embodiments of the method, for each of the plurality of pulse sets, the first, second and third transmit pulses form an inversion recovery with electron-spin echo detection (IRESE) sequence having a π-pulse as the first pulse, a T delay as the first delay, a π/2-pulse as the second pulse, a τ delay as the second delay, a π-pulse as the third pulse, a τ delay as the third delay, wherein the first, second and third pulses are each about 35 ns in duration, wherein the π/2 pulse rotates a magnetization π/2 radians and the π-pulses rotate a magnetization π radians, wherein τ=630 ns, wherein T has a value in a range of about 500 ns to about 16,000 ns, wherein the cycles of RF have a frequency of about 250 MHz, wherein the plurality of pulse sets apply a sixteen-step phase cycling, wherein about 7520 acquisitions are acquired per value of T and include phase cycling, wherein eight T values that are approximately logarithmically spaced between one-half microseconds (0.5 μs) and sixteen microseconds (16 μs) are used, wherein $T^{LF}_R$=25 μs, and wherein the phase cycling uses values selected according to the following table:

| N | First pulse | First delay | Second pulse | Second delay | Third pulse | Third delay | Detection channel Re (real) | Detection channel Im (imaginary) |
|---|---|---|---|---|---|---|---|---|
| 1 | X | T | 0.5X | 630 ns | X | 630 ns | A | B |
| 2 | X | T | 0.5X | 630 ns | −X | 630 ns | A | B |
| 3 | X | T | 0.5X | 630 ns | Y | 630 ns | −A | −B |
| 4 | X | T | 0.5X | 630 ns | −Y | 630 ns | −A | −B |
| 5 | X | T | −0.5X | 630 ns | X | 630 ns | −A | −B |
| 6 | X | T | −0.5X | 630 ns | −X | 630 ns | −A | −B |
| 7 | X | T | −0.5X | 630 ns | Y | 630 ns | A | B |
| 8 | X | T | −0.5X | 630 ns | −Y | 630 ns | A | B |
| 9 | X | T | 0.5Y | 630 ns | X | 630 ns | B | −A |
| 10 | X | T | 0.5Y | 630 ns | −X | 630 ns | B | −A |
| 11 | X | T | 0.5Y | 630 ns | Y | 630 ns | −B | A |
| 12 | X | T | 0.5Y | 630 ns | −Y | 630 ns | −B | A |
| 13 | X | T | −0.5Y | 630 ns | X | 630 ns | −B | A |
| 14 | X | T | −0.5Y | 630 ns | −X | 630 ns | −B | A |
| 15 | X | T | −0.5Y | 630 ns | Y | 630 ns | B | −A |
| 16 | X | T | −0.5Y | 630 ns | −Y | 630 ns | B | −A. |

Some embodiments of the method further include digitally signal processing the received electrical signal to generate image data; storing the image data; and displaying the image data.

In some embodiments, the present invention provides an apparatus for electron paramagnetic resonance imaging (EPRI) of a volume of animal tissue in vivo in an animal. This apparatus includes means (as described herein and equivalents thereto) for generating a substantially static magnetic field in the volume of animal tissue; and means for generating a plurality of pulse sets, wherein the means for generating each one of the plurality of pulse sets includes: means for generating a first RF excitation magnetic field pulse having a plurality of RF cycles in a first direction generally orthogonal to the substantially static magnetic field in the volume of animal tissue from a surface of the animal next to the volume of animal tissue; means for delaying for a first delay time; means for generating a second RF excitation magnetic field pulse having a plurality of RF in the first direction generally orthogonal to the substantially static magnetic field; means for sensing an RF spin-relaxation signal; and means for generating a received electrical signal based on the sensed RF signal; wherein the first, second and third RF excitation magnetic field pulses are of magnitudes and durations configured to measure $T_1$ spin-lattice relaxation in the volume of tissue.

In some embodiments of this apparatus, for different ones of the plurality of pulse sets, the second transmit pulses have RF cycles that are shifted in phase by a selected different amount (by about either 0 degrees, 90 degrees, 180 degrees or 270 degrees) relative to the first pulse, and the third pulses have RF cycles that are shifted in phase by a selected different amount (by about either 0 degrees, 90 degrees, 180 degrees or 270 degrees) relative to the first pulse. In some embodiments of this apparatus, for each of the plurality of pulse sets: the first transmit pulse is a pi pulse having a magnitude and duration selected to rotate an electron paramagnetic resonance spin by pi radians; the second transmit pulse is a pi/2 pulse having a magnitude and duration selected to rotate an electron paramagnetic resonance spin ½ pi radians; and the third transmit pulse is a pi pulse having a magnitude and duration selected to rotate an electron paramagnetic resonance spin pi radians. In some embodiments of the apparatus, for each of the plurality of pulse sets, the first, second and third transmit pulses form an inversion recovery with electron-spin echo detection (IRESE) sequence.

In some embodiments of the apparatus, for each of the plurality of pulse sets: the first, second and third transmit pulses form an inversion recovery with electron-spin echo detection (IRESE) sequence having a π-pulse as the first pulse, a T delay as the first delay, a π/2-pulse as the second pulse, a τ delay as the second delay, a π-pulse as the third pulse, a τ delay as the third delay, wherein the first, second and third pulses are each about 35 ns in duration, wherein the π/2 pulse rotates a magnetization π/2 radians and the π-pulses rotate a magnetization π radians, wherein τ=630 ns, wherein the cycles of RF have a frequency of about 250 MHz, wherein the plurality of pulse sets apply a sixteen-step phase cycling, wherein about 7520 acquisitions are acquired per value of T and include phase cycling, wherein eight T values are approximately logarithmically spaced between one-half microseconds (0.5 μs) and sixteen microseconds (16 μs) are used, wherein $T^{LF}_R$=25 μs, and wherein the phase cycling uses values selected from rows of the following table:

| First pulse | First delay | Second pulse | Second delay | Third pulse | Third delay | Detection channel Re (real) | Detection channel Im (imaginary) |
|---|---|---|---|---|---|---|---|
| X | T | 0.5X | 630 ns | X | 630 ns | A | B |
| X | T | 0.5X | 630 ns | −X | 630 ns | A | B |
| X | T | 0.5X | 630 ns | Y | 630 ns | −A | −B |
| X | T | 0.5X | 630 ns | −Y | 630 ns | −A | −B |
| X | T | −0.5X | 630 ns | X | 630 ns | −A | −B |
| X | T | −0.5X | 630 ns | −X | 630 ns | −A | −B |
| X | T | −0.5X | 630 ns | Y | 630 ns | A | B |
| X | T | −0.5X | 630 ns | −Y | 630 ns | A | B |
| X | T | 0.5Y | 630 ns | X | 630 ns | B | −A |

-continued

| First pulse | First delay | Second pulse | Second delay | Third pulse | Third delay | Detection channel Re (real) | Detection channel Im (imaginary) |
|---|---|---|---|---|---|---|---|
| X | T | 0.5Y | 630 ns | −X | 630 ns | B | −A |
| X | T | 0.5Y | 630 ns | Y | 630 ns | −B | A |
| X | T | 0.5Y | 630 ns | −Y | 630 ns | −B | A |
| X | T | −0.5Y | 630 ns | X | 630 ns | −B | A |
| X | T | −0.5Y | 630 ns | −X | 630 ns | −B | A |
| X | T | −0.5Y | 630 ns | Y | 630 ns | B | −A |
| X | T | −0.5Y | 630 ns | −Y | 630 ns | B | −A |

Some embodiments of the apparatus further include a magnetic-field generator configured to generate a substantially static magnetic field in the volume of animal tissue, which is generally orthogonal to the excitation magnetic field and to the sensed magnetic field in the volume of animal tissue, and wherein the excitation magnetic field is generally orthogonal to the sensed magnetic field in the volume of animal tissue; a digital-signal processor (DSP) unit operatively coupled to the RF receiver circuit and configured to process the received electrical signal and to generate image data; a storage unit operatively coupled to the DSP unit to receive and store the image data; and a display unit operatively coupled to the storage unit to receive and display the image data.

It is to be understood that the above description is intended to be illustrative, and not restrictive. Although numerous characteristics and advantages of various embodiments as described herein have been set forth in the foregoing description, together with details of the structure and function of various embodiments, many other embodiments and changes to details will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein," respectively. Moreover, the terms "first, " "second," and "third," etc., are used merely as labels, and are not intended to impose numerical requirements on their objects.

What is claimed is:

1. An apparatus for electron paramagnetic resonance oxygen imaging (EPROI) of a volume of animal tissue in vivo, the apparatus comprising:
    a magnetic-field generator configured to generate a substantially static magnetic field in the volume of animal tissue;
    a set of transmit coils, wherein the set of transmit coils transmit RF pulses that generate an excitation magnetic field in the volume of animal tissue in response to an applied electrical signal; and
    a set of receive coils, wherein the set of receive coils generates a sensed electrical signal in response to a sensed magnetic field in the volume of animal tissue, wherein the set of receive coils is configured to detect electron paramagnetic resonance signals in the volume of animal tissue and wherein the set of transmit coils and the set of receive coils are high-isolation coils configured to reduce the reception of the transmitted RF pulses by the receive coils;
    a pulsed-RF driver circuit, operatively coupled to the set of transmit coils, that drives a plurality of pulse sets, wherein each pulse set has a plurality of successive transmitted pulses, including a first pulse having a plurality of cycles of RF, followed by a first delay and thereafter by a second pulse that includes a plurality of cycles of RF; and
    an RF receiver circuit operatively coupled to the set of receive coils to receive the sensed electrical signal from the set of receive coils and to generate a received electrical signal, wherein the transmitted pulses are of magnitudes and durations configured to measure an electron $T_{1e}$ spin-lattice relaxation in the volume of tissue in order to measure oxygen in the volume of tissue.

2. The apparatus of claim 1, wherein for different ones of the plurality of pulse sets:
    the second transmit pulses have RF cycles that are shifted in phase by a selected different amount (by about either 0 degrees, 90 degrees, 180 degrees or 270 degrees for different ones of the plurality of pulse sets) relative to the first pulse.

3. The apparatus of claim 1, wherein each pulse set includes the first pulse, followed by the first delay and thereafter by the second pulse, wherein the second pulse is followed by a second delay and thereafter by a third pulse that includes a plurality of cycles of RF.

4. The apparatus of claim 3, wherein for different ones of the plurality of pulse sets, the second transmit pulses have RF cycles that are shifted in phase by a selected different amount (by about either 0 degrees, 90 degrees, 180 degrees or 270 degrees) relative to the first pulse, and the third pulses have RF cycles that are shifted in phase by a selected different amount (by about either 0 degrees, 90 degrees, 180 degrees or 270 degrees) relative to the first pulse.

5. The apparatus of claim 3, wherein for each of the plurality of pulse sets, the first, second and third transmit pulses form an inversion recovery with electron-spin echo detection (IRESE) sequence.

6. The apparatus of claim 3, wherein for each of the plurality of pulse sets,
    the first, second and third transmit pulses form an inversion recovery with electron-spin echo detection (IRESE) sequence having a π-pulse as the first pulse, a T delay as the first delay, a π/2-pulse as the second pulse, a τ delay as the second delay, a π-pulse as the third pulse, wherein the first, second and third pulses are each about 35 ns in duration,
    wherein the π/2 pulse rotates a magnetization π/2 radians and the π-pulses rotate a magnetization π radians,
    wherein τ=630 ns,
    wherein T has a value in a range of about 500 ns to about 16,000 ns, and
    wherein the cycles of RF have a frequency of about 250 MHz.

7. The apparatus of claim 3, wherein for each of the plurality of pulse sets, the first, second and third transmit pulses form an inversion recovery with electron-spin echo detection (IRESE) sequence having a π-pulse as the first pulse, a T delay as the first delay, a π/2-pulse as the second pulse, a τ delay as the second delay, a π-pulse as the third pulse, a τ delay as a third delay, wherein the first, second and third pulses are each about 35 ns in duration, wherein the π/2 pulse rotates a magnetization π/2 radians and the π-pulses rotate a magnetization π radians, wherein τ=630 ns, wherein T has a value in a range of about 500 ns to about 16,000 ns, wherein the cycles of RF have a frequency of about 250 MHz, wherein the plurality of pulse sets about 7520 acquisitions wherein about 7520 acquisitions are acquired per value of T and include phase cycling, wherein eight T values that are approximately logarithmically spaced between one-half microseconds (0.5 μs) and sixteen microseconds (16 μs) are used, wherein $T^{LF}_R$=25 μs, and wherein the phase cycling includes values selected from rows of the following table:

| First pulse | First delay | Second pulse | Second delay | Third pulse | Third delay | Detection channel Re (real) | Detection channel Im (imaginary) |
|---|---|---|---|---|---|---|---|
| X | T | 0.5X | 630 ns | X | 630 ns | A | B |
| X | T | 0.5X | 630 ns | −X | 630 ns | A | B |
| X | T | 0.5X | 630 ns | Y | 630 ns | −A | −B |
| X | T | 0.5X | 630 ns | −Y | 630 ns | −A | −B |
| X | T | −0.5X | 630 ns | X | 630 ns | −A | −B |
| X | T | −0.5X | 630 ns | −X | 630 ns | −A | −B |
| X | T | −0.5X | 630 ns | Y | 630 ns | A | B |
| X | T | −0.5X | 630 ns | −Y | 630 ns | A | B |
| X | T | 0.5Y | 630 ns | X | 630 ns | B | −A |
| X | T | 0.5Y | 630 ns | −X | 630 ns | B | −A |
| X | T | 0.5Y | 630 ns | Y | 630 ns | −B | A |
| X | T | 0.5Y | 630 ns | −Y | 630 ns | −B | A |
| X | T | −0.5Y | 630 ns | X | 630 ns | −B | A |
| X | T | −0.5Y | 630 ns | −X | 630 ns | −B | A |
| X | T | −0.5Y | 630 ns | Y | 630 ns | B | −A |
| X | T | −0.5Y | 630 ns | −Y | 630 ns | B | −A. |

8. The apparatus of claim 3, wherein the substantially static magnetic field in the volume of animal tissue is generally orthogonal to both the excitation magnetic field and to the sensed magnetic field in the volume of animal tissue; and wherein the apparatus further comprises:

a digital-signal processor (DSP) unit operatively coupled to the RF receiver circuit and configured to process the received electrical signal and to generate image data;

a storage unit operatively coupled to the DSP unit to receive and store the image data; and a display unit operatively coupled to the storage unit to receive and display the image data.

9. The apparatus of claim 2, further comprising:

a digital-signal processor (DSP) unit operatively coupled to the RF receiver circuit and configured to process the received electrical signal and to generate image data; and a display unit operatively coupled to receive and display the image data.

10. An apparatus for electron paramagnetic resonance oxygen imaging (EPROI) of a volume of animal tissue in vivo in an animal, the apparatus comprising:

means for generating a substantially static magnetic field in the volume of animal tissue;

means for generating a plurality of pulse sets, wherein the means for generating each one of the plurality of pulse sets includes:

means for generating a first RF excitation magnetic field pulse having a plurality of RF cycles in a first direction generally orthogonal to the substantially static magnetic field in the volume of animal tissue from a surface of the animal next to the volume of animal tissue, means for delaying for a first delay time after the first RF excitation magnetic field pulse, means for generating a second RF excitation magnetic field pulse having a plurality of RF in the first direction generally orthogonal to the substantially static magnetic field, means for sensing an RF spin-relaxation signal, and means for generating a received electrical signal based on the sensed RF signal;

wherein the first and second RF excitation magnetic field pulses are of magnitudes and durations configured to measure $T_{1e}$ spin-lattice relaxation response in the volume of tissue in order to measure oxygen in the volume of tissue; and means for generating an EPROI image of the in vivo animal tissue using the $T_{1e}$ response.

11. The apparatus of claim 10, wherein for different ones of the plurality of pulse sets:

the second transmit pulses have RF cycles that are shifted in phase by a selected different amount (by about either 0 degrees, 90 degrees, 180 degrees or 270 degrees for different ones of the plurality of pulse sets) relative to the first pulse.

12. The apparatus of claim 10, further comprising:

means for delaying for a second delay time after the second RF excitation magnetic field pulse;

means for generating a third RF excitation magnetic field pulse having a plurality of RF in the first direction generally orthogonal to the substantially static magnetic field.

13. The apparatus of claim 12, wherein for different ones of the plurality of pulse sets:

the second transmit pulses have RF cycles that are shifted in phase by a selected different amount (by about either 0 degrees, 90 degrees, 180 degrees or 270 degrees for different ones of the plurality of pulse sets) relative to the first pulse, and wherein $T^{LF}_R = 25$ μs, and wherein the phase cycling uses values selected from rows of the following table:

| First pulse | First delay | Second pulse | Second delay | Third pulse | Third delay | Detection channel Re (real) | Detection channel Im (imaginary) |
|---|---|---|---|---|---|---|---|
| X | T | 0.5X | 630 ns | X | 630 ns | A | B |
| X | T | 0.5X | 630 ns | −X | 630 ns | A | B |
| X | T | 0.5X | 630 ns | Y | 630 ns | −A | −B |
| X | T | 0.5X | 630 ns | −Y | 630 ns | −A | −B |
| X | T | −0.5X | 630 ns | X | 630 ns | −A | −B |
| X | T | −0.5X | 630 ns | −X | 630 ns | −A | −B |
| X | T | −0.5X | 630 ns | Y | 630 ns | A | B |
| X | T | −0.5X | 630 ns | −Y | 630 ns | A | B |
| X | T | 0.5Y | 630 ns | X | 630 ns | B | −A |
| X | T | 0.5Y | 630 ns | −X | 630 ns | B | −A |
| X | T | 0.5Y | 630 ns | Y | 630 ns | −B | A |
| X | T | 0.5Y | 630 ns | −Y | 630 ns | −B | A |
| X | T | −0.5Y | 630 ns | X | 630 ns | −B | A |
| X | T | −0.5Y | 630 ns | −X | 630 ns | −B | A |
| X | T | −0.5Y | 630 ns | Y | 630 ns | B | −A |
| X | T | −0.5Y | 630 ns | −Y | 630 ns | B | −A. | the third transmit pulses have RF cycles that are shifted in phase by a selected different amount (by about either 0 degrees, 90 degrees, 180 degrees or 270 degrees) relative to the first pulse.

14. The apparatus of claim 12, wherein for each of the plurality of pulse sets:
the first transmit pulse is a pi pulse having a magnitude and duration selected to rotate an electron paramagnetic resonance spin by pi radians;
the second transmit pulse is a pi/2 pulse having a magnitude and duration selected to rotate an electron paramagnetic resonance spin 1/2 pi radians; and
the third transmit pulse is a pi pulse having a magnitude and duration selected to rotate an electron paramagnetic resonance spin pi radians.

15. The apparatus of claim 12, wherein for each of the plurality of pulse sets, the first, second and third transmit pulses form an inversion recovery with electron-spin echo detection (IRESE) sequence.

16. The apparatus of claim 12, wherein for each of the plurality of pulse sets,
the first, second and third transmit pulses form an inversion recovery with electron-spin echo detection (IRESE) sequence having a π-pulse as the first pulse, a T delay as the first delay, a π/2-pulse as the second pulse, a τ delay as the second delay, a π-pulse as the third pulse, a τ delay as a third delay, wherein the first, second and third pulses are each about 35 ns in duration,
wherein the π/2 pulse rotates a magnetization π/2 radians and the π-pulses rotate a magnetization π radians,
wherein τ=630 ns,
wherein T has a value in a range of about 500 ns to about 16,000 ns,
wherein the cycles of RF have a frequency of about 250 MHz,
wherein the plurality of pulse sets apply a sixteen-step phase cycling,
wherein about 7520 acquisitions are acquired per value of T and include phase cycling,
wherein eight T values are approximately logarithmically spaced between one-half microseconds (0.5 μs) and sixteen microseconds (16 μs) are used, 17. The apparatus of claim 10, wherein the means for generating an EPROI image includes:
digital-signal-processing means operatively coupled to process the received electrical signal and to generate image data;
storage means operatively coupled to receive and store the image data; and
display means operatively coupled to the storage means to receive and display the image data.

18. The apparatus of claim 2, further comprising:
a digital-signal processor (DSP) unit operatively coupled to the RF receiver circuit and configured to process the received electrical signal and to generate image data; and
a storage unit operatively coupled to the DSP unit to receive and store the image data.

19. The apparatus of claim 2, wherein each of the plurality of pulse sets further includes a third transmit pulse, and wherein for each of the plurality of pulse sets:
the first transmit pulse is a pi pulse having a magnitude and duration selected to rotate an electron paramagnetic resonance spin by pi radians;
the second transmit pulse is a pi/2 pulse having a magnitude and duration selected to rotate an electron paramagnetic resonance spin 1/2 pi radians; and
the third transmit pulse is a pi pulse having a magnitude and duration selected to rotate an electron paramagnetic resonance spin pi radians.

20. The apparatus of claim 1, wherein the transmitted RF pulses are of magnitudes and durations configured to measure an electron $T_{1e}$ spin-lattice relaxation using a reporter molecule in the volume of tissue.

21. The apparatus of claim 10, wherein the transmitted RF pulse sets are of magnitudes and durations configured to measure an electron $T_{1e}$ spin-lattice relaxation using a reporter molecule in the volume of tissue.

* * * * *